(12) United States Patent
Bradbury et al.

(10) Patent No.: US 7,820,683 B2
(45) Date of Patent: Oct. 26, 2010

(54) 4-(1H-INDAZOL-5-YL-AMINO)-QUINAZOLINE COMPOUNDS AS ERBB RECEPTOR TYROSINE KINASE INHIBITORS FOR THE TREATMENT OF CANCER

(75) Inventors: Robert Hugh Bradbury, Macclesfield (GB); Bernard Christophe Barlaam, Reims (FR); Richard Ducray, Reims (FR)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/067,416

(22) PCT Filed: Sep. 14, 2006

(86) PCT No.: PCT/GB2006/003407

§ 371 (c)(1),
(2), (4) Date: Aug. 12, 2008

(87) PCT Pub. No.: WO2007/034144

PCT Pub. Date: Mar. 29, 2007

(65) Prior Publication Data

US 2009/0048251 A1 Feb. 19, 2009

(30) Foreign Application Priority Data

Sep. 20, 2005 (EP) .................. 05291948
Dec. 2, 2005 (EP) .................. 05292547
Apr. 7, 2006 (EP) .................. 06300343

(51) Int. Cl.
A61K 31/517 (2006.01)

(52) U.S. Cl. .................. 514/266.4; 544/293; 548/362.5

(58) Field of Classification Search .................. 544/293
See application file for complete search history.

(56) References Cited

U.S. PATENT DOCUMENTS

| | | | |
|---|---|---|---|
| 4,322,420 A | 3/1982 | Kobayashi et al. |
| 4,335,127 A | 6/1982 | Vandenberk et al. |
| 4,640,920 A | 2/1987 | Boyle et al. |
| 4,921,863 A | 5/1990 | Sugimoto et al. |
| 5,405,843 A | 4/1995 | Fukazawa et al. |
| 5,721,237 A | 2/1998 | Myers et al. |
| 5,747,498 A | 5/1998 | Schnur et al. |
| 5,929,080 A | 7/1999 | Frost |
| 5,962,458 A | 10/1999 | Lohmann et al. |
| 6,004,967 A | 12/1999 | McMahon et al. |
| 6,046,206 A | 4/2000 | Pamukcu et al. |
| 6,117,433 A | 9/2000 | Edens et al. |
| 6,297,258 B1 | 10/2001 | Wissner et al. |
| 6,313,130 B1 | 11/2001 | Uckun et al. |
| 6,326,373 B1 | 12/2001 | Uckun et al. |
| 6,384,223 B1 | 5/2002 | Gletsos |
| 6,562,319 B2 | 5/2003 | Mishani et al. |
| 6,972,288 B1 | 12/2005 | Himmelsbach et al. |
| 7,148,230 B2 | 12/2006 | Bradbury et al. |
| 2002/0082270 A1 | 6/2002 | Himmelsbach et al. |
| 2002/0128553 A1 | 9/2002 | Mishani et al. |
| 2003/0186995 A1 | 10/2003 | Kath et al. |
| 2004/0048880 A1 | 3/2004 | Himmelsbach et al. |
| 2004/0176361 A1 | 9/2004 | Fujio et al. |
| 2005/0043336 A1 | 2/2005 | Hennequin et al. |
| 2005/0054662 A1 | 3/2005 | Hennequin et al. |
| 2005/0215574 A1 | 9/2005 | Bradbury et al. |
| 2006/0211714 A1 | 9/2006 | Hennequin et al. |
| 2006/0287295 A1 | 12/2006 | Barlaam et al. |
| 2007/0015743 A1 | 1/2007 | Bradbury et al. |
| 2007/0032508 A1 | 2/2007 | Bradbury et al. |
| 2007/0032513 A1 | 2/2007 | Hennequin et al. |
| 2007/0037837 A1 | 2/2007 | Hennequin et al. |
| 2007/0043009 A1 | 2/2007 | Hennequin et al. |
| 2007/0043010 A1 | 2/2007 | Bradbury et al. |
| 2007/0082921 A1 | 4/2007 | Hennequin et al. |
| 2007/0088044 A1 | 4/2007 | Hennequin et al. |
| 2007/0099943 A1 | 5/2007 | Bradbury et al. |
| 2007/0149546 A1 | 6/2007 | Bradbury et al. |
| 2007/0232607 A1 | 10/2007 | Bradbury et al. |
| 2007/0244136 A1 | 10/2007 | Hennequin et al. |
| 2007/0293490 A1 | 12/2007 | Delouvrie et al. |

FOREIGN PATENT DOCUMENTS

| | | |
|---|---|---|
| CA | 2476008 | 10/2003 |
| CA | 2543649 | 5/2005 |
| EP | 0288563 | 11/1988 |
| EP | 0566226 | 11/1995 |
| EP | 0602851 | 10/1996 |

(Continued)

OTHER PUBLICATIONS

Ballard et al. "Developing a small molecule erbB2 inhibitor:challenges with optimising DMPK properties" Poster—Presented at DMDG Cambridge (Feb. 6, 2008).

(Continued)

*Primary Examiner*—James O Wilson
*Assistant Examiner*—Brian McDowell

(57) ABSTRACT

A quinazoline derivative of the Formula I:

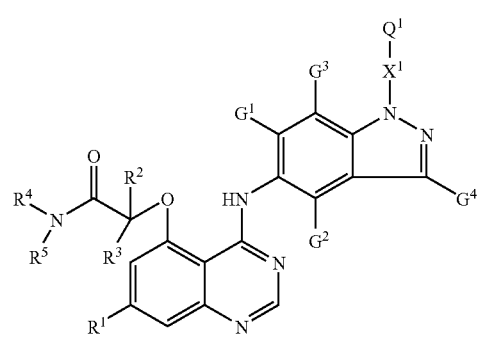

wherein the substituents are as defined in the text for use in the production of an anti-proliferative effect which effect is produced alone or in part by inhibiting erbB2 receptor tyrosine kinase in a warm-blooded animal such as man.

20 Claims, No Drawings

FOREIGN PATENT DOCUMENTS

| | | |
|---|---|---|
| EP | 0520722 | 12/1996 |
| EP | 0787722 | 8/1997 |
| EP | 0837063 | 4/1998 |
| EP | 0326330 | 7/2002 |
| EP | 1230919 | 8/2002 |
| EP | 1369418 | 12/2003 |
| GB | 2295387 | 5/1996 |
| JP | 08-003144 | 1/1996 |
| JP | 11-189586 | 7/1999 |
| WO | WO 88/02365 | 4/1988 |
| WO | WO 92/20642 | 11/1992 |
| WO | WO 93/08170 | 4/1993 |
| WO | WO 93/17682 | 9/1993 |
| WO | WO 95/15758 | 6/1995 |
| WO | WO 96/09294 | 3/1996 |
| WO | WO 96/15118 | 5/1996 |
| WO | WO 96/16960 | 6/1996 |
| WO | WO 96/30347 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 97/03069 | 1/1997 |
| WO | WO 97/11692 | 4/1997 |
| WO | WO 97/13771 | 4/1997 |
| WO | WO 97/22596 | 6/1997 |
| WO | WO 97/30034 | 8/1997 |
| WO | WO 97/30035 | 8/1997 |
| WO | WO 97/30044 | 8/1997 |
| WO | WO 97/38983 | 10/1997 |
| WO | WO 97/38994 | 10/1997 |
| WO | WO 98/02434 | 1/1998 |
| WO | WO 98/02437 | 1/1998 |
| WO | WO 98/02438 | 1/1998 |
| WO | WO 98/13354 | 4/1998 |
| WO | WO 98/38984 | 9/1998 |
| WO | WO 98/50038 | 11/1998 |
| WO | WO 98/50370 | 11/1998 |
| WO | WO 99/06378 | 2/1999 |
| WO | WO 99/09016 | 2/1999 |
| WO | WO 99/24037 | 5/1999 |
| WO | WO 99/35132 | 7/1999 |
| WO | WO 99/35146 | 7/1999 |
| WO | WO 99/61428 | 12/1999 |
| WO | WO 00/00202 | 1/2000 |
| WO | WO 00/06555 | 2/2000 |
| WO | WO 00/09481 | 2/2000 |
| WO | WO 00/10981 | 3/2000 |
| WO | WO 00/18740 | 4/2000 |
| WO | WO 00/20402 | 4/2000 |
| WO | WO 00/24718 | 5/2000 |
| WO | WO 00/44728 | 8/2000 |
| WO | WO 00/47212 | 8/2000 |
| WO | WO 00/51587 | 9/2000 |
| WO | WO 00/51991 | 9/2000 |
| WO | WO 00/55141 | 9/2000 |
| WO | WO 00/73260 | 12/2000 |
| WO | WO 01/07432 | 2/2001 |
| WO | WO 01/12227 | 2/2001 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | WO 01/32632 | 5/2001 |
| WO | WO 01/45641 | 6/2001 |
| WO | WO 01/77085 | 10/2001 |
| WO | WO 01/94341 | 12/2001 |
| WO | WO 01/98277 | 12/2001 |
| WO | WO 02/18372 | 3/2002 |
| WO | WO 02/24684 | 3/2002 |
| WO | WO 02/30924 | 4/2002 |
| WO | WO 02/34744 | 5/2002 |
| WO | WO 02/41882 | 5/2002 |
| WO | WO 02/44166 | 6/2002 |
| WO | WO 02/48117 | 6/2002 |
| WO | WO 02/056882 | 7/2002 |
| WO | WO 02/062767 | 8/2002 |
| WO | WO 02/066445 | 8/2002 |
| WO | WO 02/068409 | 9/2002 |
| WO | WO 02/073235 | 9/2002 |
| WO | WO 02/076976 | 10/2002 |
| WO | WO 02/092577 | 11/2002 |
| WO | WO 02/092578 | 11/2002 |
| WO | WO 02/094790 | 11/2002 |
| WO | WO 03/040108 | 5/2003 |
| WO | WO 03/040109 | 5/2003 |
| WO | WO 03/049740 | 6/2003 |
| WO | WO 03/082290 | 10/2003 |
| WO | WO 03/082831 | 10/2003 |
| WO | WO 2004/006846 | 1/2004 |
| WO | WO 2004/046101 | 6/2004 |
| WO | WO 2004/064718 | 8/2004 |
| WO | WO 2004/093880 | 11/2004 |
| WO | WO 2004/096226 | 11/2004 |
| WO | WO 2005/012290 | 2/2005 |
| WO | WO 2005/013998 | 2/2005 |
| WO | WO 2005/026150 | 3/2005 |
| WO | WO 2005/026151 | 3/2005 |
| WO | WO 2005/026152 | 3/2005 |
| WO | WO 2005/026156 | 3/2005 |
| WO | WO 2005/026157 | 3/2005 |
| WO | WO 2005/028469 | 3/2005 |
| WO | WO 2005/028470 | 3/2005 |
| WO | WO 2005/030757 | 3/2005 |
| WO | WO 2005/030765 | 4/2005 |
| WO | WO 2005/051923 | 5/2005 |
| WO | WO 2005/051923 | 6/2005 |
| WO | WO 2005/075439 | 8/2005 |
| WO | WO 2005/097134 | 10/2005 |
| WO | WO 2005/118572 | 12/2005 |
| WO | WO 2006/008526 | 1/2006 |
| WO | WO 2006/064196 | 6/2006 |
| WO | WO 2006/090163 | 8/2006 |
| WO | WO 2006/092573 | 9/2006 |
| WO | WO 2006/092574 | 9/2006 |
| WO | WO 2006/117521 | 11/2006 |
| WO | WO 2006/117523 | 11/2006 |
| WO | WO 2007/034143 | 3/2007 |
| WO | WO 2007/063291 | 6/2007 |
| WO | WO 2007/063293 | 6/2007 |

OTHER PUBLICATIONS

Barlaam et al. "Indazolylamino/Anilinoquinazolines Bearing a C-5 Substitution as erbB2 Kinase Inhibitors: Structure-Activity Relationships and Identification of a Candidate Drug" Poster No. P044, presented at XXth International Symposium on Medicinal Chemistry (EFMC-ISMC 2008), Vienna, Austria, Aug. 31-Sep. 4, 2008.

Barlaam et al. "Indazolylamino/Anilinoquinazolines Bearing a C-5 substitution as erbB2 kinase inhibitors: Structure-activity relationships and identification of a candidate drug" at AACR in 2007.

Grunwald et al. "Developing inhibitors of the epidermal growth factor receptor for cancer treatment" Review, Journal of the National Cancer Institute 95(12):851-867 (2003).

Harris et al. "Systematic variation of a key quinazoline core" Presented at the XXII European Colloquium on Heterocyclic Chemistry (XXII ECHC-2006) Bari, Italy, Sep. 2-6, 2006.

Cockerill et al. "Indazolylamino quinazolines and pyridopyrimidines as inhibitors of the EGFr and c-erbB-2" Bioorganic & Medicinal Chemistry Letters 11(11):1401-1405 (2001).

Gaul et al. "Discovery and Biological Evaluation of Potent Dual ErbB-2/EGFR Tyrosine Kinase Inhibitors: 6-Thiazolylquinazolines" Bioorganic & Medicinal Chemistry Letters 13(4):637-640 (2003).

Ballard et al. "5-Substituted 4-anilinoquinazolines as potent, selective and orally active inhibitors of erbB2 receptor tyrosine kinase" Bioorg Med Chem Lett. 15(19):4226-4229 (2005).

Ballard et al. "Inhibitors of epidermal growth factor receptor tyrosine kinase: Novel C-5 substituted anilinoquinazolines designed to target the ribose pocket" Bioorg Med Chem Lett. 16(6):1633-1637 (2006).

Ballard et al. "Inhibitors of epidermal growth factor receptor tyrosine kinase: optimisation of potency and in vivo pharmacokinetics" Bioorg Med Chem Lett. 16(18):4908-4912 (2006).

Ballard et al. "Neutral 5-substituted 4-anilinoquinazolines as potent, orally active inhibitors of erbB2 receptor tyrosine kinase" Bioorg Med Chem Lett. 17(22):6326-6329 (2007).

Barker et al. "Studies leading to the identification of ZD1839 (Iressa™): an orally active, selective epidermal growth factor receptor tyrosine kinase inhibitor targeted to the treatment of cancer" Bioorganic and Medicinal Chemistry Letters 11(14):1911-1914 (2001).

Barlaam et al. "A new series of neutral 5-substituted 4-anilinoquinazolines as potent, orally active inhibitors of erbB2 receptor tyrosine kinase" Bioorganic & Medicinal Chemistry Letters 18(2):674-678 (2008).

Barlaam et al. "Neutral 5-substituted 4-indazolylaminoquinazolines as potent, orally active inhibitors of erbB2 receptor tyrosine kinase" Bioorganic & Medicinal Chemistry Letters 18(6):1799-1803 (2008).

Bridges et al. "Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor" J. Med. Chem. 39(1):267-276 (1996).

Denny et al. "Structure-activity relationships for 4-anilinoquinazolines as potent inhibitors at the ATP binding site for the epidermal growth factor receptor in vitro" Clinical and Experimental Pharmacology and Physiology 23:424-427 (1996).

Ducray et al. "Novel 3-alkoxy-1H-pyrazolo[3,4-d]pyrimidines as EGFR and erbB2 receptor tyrosine kinase inhibitors" Bioorganic & Medicinal Chemistry Letters 18(3):959-962 (2008).

Harris et al. "Facile synthesis of 7-amino anilinoquinazolines via direct amination of the quinazoline core" Tetrahedron letters 46(43): 7381-7384 (2005).

Harris et al. "Selective alkylation of a 6,7-dihydroxyquinazoline" Tetrahedron letters 46(45):7715-7719 (2005).

Hennequin et al. "N-(5-chloro-1,3-benzodioxol-4-yl)-7-[2-(4-methylpiperazin-1-yl)ethoxy]-5-(tetrahydro-2H-pyran-4-yloxy)quinazolin-4-amine, a novel, highly selective, orally available, dual-specific c-Src/Abl kinase inhibitor" J Med Chem. 49(22):6465-6488 (2006).

Hennequin et al. "Novel 4-anilinoquinazolines with C-6 carbon-linked side chains: synthesis and structure-activity relationship of a series of potent, orally active, EGF receptor tyrosine kinase inhibitors" Bioorg Med Chem Lett. 16(10):2672-2676 (2006).

Hennequin et al. "Novel 4-Anilinoquinazolines with C-7 Basic Side Chains: Design and Structure Activity Relationship of a Series of Potent, Orally Active, VEGF Receptor Tyrosine Kinase Inhibitors" J. Med. Chem. 45 (6):1300-1312 (2002).

Jani et al. "Discovery and pharmacologic characterization of CP-724,714, a selective ErbB2 tyrosine kinase inhibitor" Cancer Research 67(20):9887-9893 (2007).

Klutchko et al. "Tyrosine kinase inhibitors. 19. 6-Alkynamides of 4-anilinoquinazolines and 4-anilinopyrido[3,4-d]pyrimidines as irreversible inhibitors of the erbB family of tyrosine kinase receptors" J Med Chem. 49(4):1475-1485 (2006).

Petrov et al. "Optimization and SAR for dual ErbB-1/ErbB-2 tyrosine kinase inhibition in the 6-furanylquinazoline series" Bioorg Med Chem Lett. 16(17):4686-4691 (2006).

Rewcastle et al. "Tyrosine kinase inhibitors. 5. Synthesis and structure-activity relationships for 4-[(phenylmethyl)amino]- and 4-(phenylamino)quinazolines as potent adenoisine 5'-triphosphate binding site inhibitors of the tyrosine kinase domain of the epidermal growth factor receptor" Med. Chem. 38:3482-3487 (1995).

Stamos et al. "Structure of the Epidermal Growth Factor Receptor Kinase Domain Alone and in Complex with a 4-Anilinoquinazoline Inhibitor" J. Biol. Chem. 277(48):46265-46272 (2002).

Traxler et al. "Protein tyrosine kinase inhibitors in cancer treatment" Exp. Opin. Ther. Patents 7(6):571-588 (1997).

Traxler et al. "Tyrosine kinase inhibitors in cancer treatment (Part II)" Exp. Opin. Ther. Patents 8(12):1599-1625 (1998).

Tsou et al. "6-Substituted-4-(3-bromophenylamino)quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity" J. Med. Chem. 44:2719-2734 (2001).

Vema et al. "Design of EGFR kinase inhibitors: a ligand-based approach and its confirmation with structure-based studies" Bioorg Med Chem. 11(21):4643-4653 (2003).

4-(1H-INDAZOL-5-YL-AMINO)-QUINAZOLINE COMPOUNDS AS ERBB RECEPTOR TYROSINE KINASE INHIBITORS FOR THE TREATMENT OF CANCER

RELATED APPLICATIONS

The present application is a U.S. National Phase Application of International Application No. PCT/GB2006/003407 (filed Sep. 14, 2006) which claims the benefit of European Patent Application No. 05291948.7 (filed Sep. 20, 2005), European Patent Application No. 05292547.6 (filed Dec. 2, 2005) and European Patent Application No. 06300343.8 (filed Apr. 7, 2006), all of which are hereby incorporated by reference in their entirety.

The invention concerns certain novel quinazoline derivatives, or pharmaceutically acceptable salts thereof, which possess anti-tumour activity and are accordingly useful in methods of treatment of the human or animal body. The invention also concerns processes for the manufacture of said quinazoline derivatives, pharmaceutical compositions containing them and their use in therapeutic methods, for example in the manufacture of medicaments for use in the prevention or treatment of solid tumour disease in a warm-blooded animal such as man.

Many of the current treatment regimes for diseases resulting from the abnormal regulation of cellular proliferation such as psoriasis and cancer, utilise compounds that inhibit DNA synthesis and cellular proliferation. To date, compounds used in such treatments are generally toxic to cells however their enhanced effects on rapidly dividing cells such as tumour cells can be beneficial. Alternative approaches to these cytotoxic anti-tumour agents are currently being developed, for example as selective inhibitors of cell signalling pathways. These types of inhibitors are likely to have the potential to display an enhanced selectivity of action against tumour cells and so are likely to reduce the probability of the therapy possessing unwanted side effects.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors and other autocrine, paracrine and endocrine factors. By binding to specific transmembrane receptors, these ligands integrate the extracellular signal to the intracellular signalling pathways, therefore transducing the signal across the plasma membrane and allowing the individual cell to respond to its extracellular signals. Many of these signal transduction processes utilise the reversible process of the phosphorylation of proteins that are involved in the promotion of these diverse cellular responses. The phosphorylation status of target proteins is regulated by specific kinases and phosphatases that are responsible for the regulation of about one third of all proteins encoded by the mammalian genome. As phosphorylation is such an important regulatory mechanism in the signal transduction process, it is therefore not surprising that aberrations in these intracellular pathways result in abnormal cell growth and differentiation and so promote cellular transformation (reviewed in Cohen et al, *Curr Opin Chem Biol*, 1999, 3, 459-465).

It has been widely shown that a number of these tyrosine kinases are mutated to constitutively active forms and/or when over-expressed result in the transformation of a variety of human cells. These mutated and over-expressed forms of the kinase are present in a large proportion of human tumours (reviewed in Kolibaba et al, Biochimica et Biophysica Acta, 1997, 133, F217-F248). As tyrosine kinases play fundamental roles in the proliferation and differentiation of a variety of tissues, much focus has centred on these enzymes in the development of novel anti-cancer therapies. This family of enzymes is divided into two groups—receptor and non-receptor tyrosine kinases, for example EGF Receptors and the SRC family respectively. From the results of a large number of studies including the Human Genome Project, about 90 tyrosine kinase have been identified in the human genome, of this 58 are of the receptor type and 32 are of the non-receptor type. These can be compartmentalised into 20 receptor tyrosine kinase and 10 non-receptor tyrosine kinase sub-families (Robinson et al, *Oncogene*, 2000, 19, 5548-5557).

The receptor tyrosine kinases are of particular importance in the transmission of mitogenic signals that initiate cellular replication. These large glycoproteins, which span the plasma membrane of the cell possess an extracellular binding domain for their specific ligands (such as Epidermal Growth Factor (EGF) for the EGF Receptor). Binding of ligand results in the activation of the receptor's kinase enzymatic activity that resides in the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., *EMBO J.*, 2000, 19, 3159). One mechanism in which this can be accomplished is by overexpression of the receptor at the protein level, generally as a result of gene amplification. This has been observed in many common human cancers (reviewed in Klapper et al., *Adv. Cancer Res.*, 2000, 77, 25) such as breast cancer (Sainsbury et al., *Brit. J. Cancer,* 1988, 58, 458; Guerin et al., *Oncogene Res.*, 1988, 3, 21; Slamon et al., *Science,* 1989, 244, 707; Klijn et al., *Breast Cancer Res. Treat.*, 1994, 29, 73 and reviewed in Salomon et al., *Crit. Rev. Oncol. Hematol.*, 1995, 19, 183), non-small cell lung cancers (NSCLCs) including adenocarcinomas (Cerny et al., *Brit. J. Cancer,* 1986, 54, 265; Reubi et al., *Int. J. Cancer,* 1990, 45, 269; Rusch et al., *Cancer Research*, 1993, 53, 2379; Brabender et al, *Clin. Cancer Res.*, 2001, 7, 1850) as well as other cancers of the lung (Hendler et al., *Cancer Cells*, 1989, 7, 347; Ohsaki et al., *Oncol. Rep.*, 2000, 7, 603), bladder cancer (Neal et al., *Lancet*, 1985, 366; Chow et al., *Clin. Cancer Res.*, 2001, 7, 1957, Zhau et al., *Mol. Carcinog.*, 3, 254), oesophageal cancer (Mukaida et al., *Cancer,* 1991, 68, 142), gastrointestinal cancer such as colon, rectal or stomach cancer (Bolen et al., *Oncogene Res.*, 1987, 1, 149; Kapitanovic et al., *Gastroenterology*, 2000, 112, 1103; Ross et al., *Cancer Invest.*, 2001, 19, 554), cancer of the prostate (Visakorpi et al., *Histochem. J.*, 1992, 24, 481; Kumar et al., 2000, 32, 73; Scher et al., *J. Natl. Cancer Inst.*, 2000, 92, 1866), leukaemia (Konaka et al., *Cell,* 1984, 37, 1035, Martin-Subero et al., *Cancer Genet Cvtogenet.*, 2001, 127, 174), ovarian (Hellstrom et al., *Cancer Res.*, 2001, 61, 2420), head and neck (Shiga et al., *Head Neck,* 2000, 22, 599) or pancreatic cancer (Ovotny et al., *Neoplasma*, 2001, 48, 188). As more human tumour tissues are tested for expression of the erbB family of receptor tyrosine kinases it is expected that their widespread prevalence and importance will be further enhanced in the future.

As a consequence of the mis-regulation of one or more of these receptors (in particular erbB2), it is widely believed that many tumours become clinically more aggressive and so correlate with a poorer prognosis for the patient (Brabender et al, *Clin. Cancer Res.,* 2001, 7, 1850; Ross et al, *Cancer Investigation,* 2001, 19, 554, Yu et al., *Bioessays,* 2000, 22.7, 673).

In addition to these clinical findings, a wealth of pre-clinical information suggests that the erbB family of receptor tyrosine kinases are involved in cellular transformation. This includes the observations that many tumour cell lines overexpress one or more of the erbB receptors and that EGFR or erbB2 when transfected into non-tumour cells have the ability to transform these cells. This tumourigenic potential has been further verified as transgenic mice that overexpress erbB2 spontaneously develop tumours in the mammary gland. In addition to this, a number of pre-clinical studies have demonstrated that anti-proliferative effects can be induced by knocking out one or more erbB activities by small molecule inhibitors, dominant negatives or inhibitory antibodies (reviewed in Mendelsohn et al., *Oncogene,* 2000, 19, 6550). Thus it has been recognised that inhibitors of these receptor tyrosine kinases should be of value as a selective inhibitor of the proliferation of mammalian cancer cells (Yaish et al. *Science,* 1988, 242, 933, Kolibaba et al, Biochimica et Biophysica Acta, 1997, 133, F217-F248; Al-Obeidi et al, 2000, *Oncogene,* 19, 5690-5701; Mendelsohn et al, 2000, *Oncogene,* 19, 6550-6565).

In addition to this pre-clinical data, the small molecule EGFR tyrosine kinase inhibitors Iressa® (also known as gefitinib and ZD1839) and Tarceva® (also known as erlotinib and CP-358,774) have been approved for use in the treatment of advanced non-small cell lung cancer. Furthermore, inhibitory antibodies against EGFR and erbB2 (Erbitux® (c-225/cetuximab) and Herceptin® (trastuzumab) respectively) have proven to be beneficial in the clinic for the treatment of selected solid tumours (reviewed in Mendelsohn et al, 2000, *Oncogene,* 19, 6550-6565).

Recently mutations in the ATP binding pocket of the intracellular catalytic domain of the EGF receptor have been discovered in certain sub-sets of non-small cell lung cancers (NSCLCs). The presence of mutations in the receptor appear to correlate with response to EGFR tyrosine kinase inhibitors such as gefitinib (Lynch et al, N Engl J Med 2004; 350: 2129-2139; Paez et al, Science 2004; 304: 1497-1500), although it is becoming evident that the clinical benefits of compounds such as gefitinib and erlotinib are not likely to be mediated by EGFR mutations alone. It has been demonstrated that ligand stimulation results in a different phosphorylation pattern in mutated receptors compared with that seen in wild-type receptors and it is thought that mutant EGF receptors selectively transduce survival signals on which NSCLCs become dependent. Inhibition of those signals by compounds such as gefitinib may contribute to the efficacy of such drugs (Sordella et al., Science 2004; 305: 1163-1167). Similarly, mutations within the erbB2 kinase domain have recently been discovered in certain primary tumours, such as NSCLC, glioblastoma and gastric and ovarian tumours (Stephens et al., Nature 2004; 431; 525-526). Accordingly the inhibition of the EGF and/or erbB2 receptor tyrosine kinase in both wild-type and mutated receptors is an important target that would be expected to provide an anti-cancer effect.

Amplification and/or activity of members of the erbB type receptor tyrosine kinases have been detected and so have been implicated to play a role in a number of non-malignant proliferative disorders such as psoriasis (Ben-Bassat, *Curr. Pharm. Des.,* 2000, 6, 933; Elder et al., Science, 1989, 243, 811), benign prostatic hyperplasia (BPH) (Kumar et al., *Int. Urol. Nephrol.,* 2000, 32, 73), atherosclerosis and restenosis (Bokemeyer et al., *Kidney Int.,* 2000, 58, 549). It is therefore expected that inhibitors of erbB type receptor tyrosine kinases will be useful in the treatment of these and other non-malignant disorders of excessive cellular proliferation.

WO 96/09294, WO 96/15118, WO 96/16960, WO 96/30347, WO 96/33977, WO 96/33978, WO 96/33979, WO 96/33980, WO 96/33981, WO 97/03069, WO 97/13771, WO 97/30034, WO 97/30035, WO 97/38983, WO 98/02437, WO 98/02434, WO 98/02438, WO 98/13354, WO 99/35132, WO 99/35146, WO 01/21596, WO 00/55141 and WO 02/18372 each disclose that certain quinazoline derivatives which bear an anilino substituent at the 4-position possess receptor tyrosine kinase inhibitory activity. WO 97/03069 also discloses several 4-(indazol-5-ylamino)quinazoline derivatives, but none of these derivatives includes a substituent at the 5-position on the quinazoline ring.

Cockerill et al., Bioorg. & Med. Chem. Lett., 11 (2001), 1401-1405 discloses the quinazoline derivatives 4-([1-benzyl)indazol-5-yl]amino)quinazoline and 5,6-dimethoxy-4-([1-benzyl)indazol-5-yl]amino)quinazoline and their use as inhibitors of the EGF and erbB2 receptor tyrosine kinases. This document does not disclose a quinazoline derivative that includes a substituent at the 5-position on the quinazoline ring.

Lackey et al., Bioorg. & Med. Chem. Lett., 14 (2004), 111-114 discloses a 4-([1-{3-fluorobenzyl)indazol-5-yl]amino)quinazoline derivative that contains a substituent at the 6-position on the quinazoline ring and its use as an inhibitor of the EGF and erbB2 receptor tyrosine kinases. This document does not disclose a quinazoline derivative that includes a substituent at the 5-position on the quinazoline ring.

WO 01/94341 discloses that certain quinazoline derivatives which carry a 5-substituent are inhibitors of the Src family of non-receptor tyrosine kinases, such as c-Src, c-Yes and c-Fyn. There is no disclosure in WO 01/94341 of 4-(indazol-5-ylamino)quinazoline derivatives wherein the nitrogen atom of the indazolyl group is substituted by a substituent containing an aryl or a heteroaryl group.

WO 02/34744 also discloses certain quinazoline derivatives and their use as inhibitors of the Src family of non-receptor tyrosine kinases. The quinazoline derivatives contain a 7-indolylamino group at the 4-position on the quinazoline ring and a hydrogen atom at the 5-position on the quinazoline ring. There is no disclosure in this PCT application of a 4-(indazol-5-ylamino)quinazoline derivative, let alone of a 4-(indazol-5-ylamino)quinazoline derivative that contains a methoxy linked amide group at the 5-position on the quinazoline ring.

WO 03/040108 and WO 03/040109 each disclose that certain quinazoline derivatives which carry a 5-substituent are inhibitors of the erbB family of tyrosine kinase inhibitors, particularly EGF and erbB2 receptor tyrosine kinases. WO 03/040108 and WO 03/040109 each disclose certain 4-(indazol-5-ylamino)quinazoline derivatives. None of the quinazoline derivatives disclosed contain a methoxy linked amide group at the 5-position on the quinazoline ring.

WO 2004/093880 also discloses that certain quinazoline derivatives which carry a 5-position substituent are inhibitors of the erbB family of tyrosine kinase inhibitors, particularly EGF and erbB2 receptor tyrosine kinases. This PCT patent application discloses certain 4-anilino-quinazoline derivatives which carry an ethoxy linked amine substituent at the 5-position on the quinazoline ring. There is no disclosure in this application of a 4-(indazol-5-ylamino)quinazoline derivative.

WO 2005/118572 (co-pending PCT patent application number PCT/GB2005/002215) also discloses that certain quinazoline derivatives which carry a 5-substituent are inhibitors of the erbB family of tyrosine kinase inhibitors, particularly EGF and erbB2 receptor tyrosine kinases. This PCT patent application discloses certain 4-anilino-quinazoline derivatives which carry a methoxy linked amide substituent at the 5-position on the quinazoline ring. There is no disclosure in this application of a 4-(indazol-5-ylamino)quinazoline derivative.

WO 2005/097137 discloses hydroxy containing quinazoline derivatives and their use as inhibitors of protein kinases. This PCT application does not disclose a 4-(indazol-5-ylamino)quinazoline derivative, let alone a 4-(indazol-5-ylamino)quinazoline derivative that contains a methoxy linked amide group at the 5-position on the quinazoline ring.

None of the prior art discloses 4-(indazol-5-ylamino) quinazoline derivatives that are substituted at the 5-position by a methoxy linked amide group and which carry an aryl or heteroaryl containing substituent at the 1-position on the indazole ring.

There remains a need to find further compounds with good in-vivo activity together with improved pharmacological characteristics compared with known erbB tyrosine kinase inhibitors, particularly compounds that are selective erbB2 tyrosine kinase inhibitors. For example, there is a need for novel compounds with advantageous and/or improved characteristics in, but not limited to, for example, (i) physical properties; (ii) favourable DMPK properties, such as low clearance, high bioavailability and/or advantageous half life and/or advantageous volume of distribution and/or high absorption; (iii) factors that decrease the liability for clinical drug-drug interactions (for example cytochrome P450 enzyme inhibition or induction); and (iv) compounds with a reduced liability for QT interval prolongation in patients, for example compounds which are inactive or weakly active in a HERG assay.

Surprisingly, we have now found that a select group of 4-(indazol-5-ylamino)quinazoline derivatives substituted at the 5-position with a substituent containing certain methoxy-linked amide groups possess potent anti-tumour activity. Without wishing to imply that the quinazoline derivatives disclosed in the present invention possess pharmacological activity only by virtue of an effect on a single biological process, it is believed that the quinazoline derivatives provide an anti-tumour effect by way of inhibition of one or more of the erbB family of receptor tyrosine kinases that are involved in the signal transduction steps which lead to the proliferation of tumour cells. In particular, it is believed that the quinazoline derivatives of the present invention provide an anti-tumour effect by way of inhibition of EGF and/or erbB2 receptor tyrosine kinases. More particularly, it is believed that the quinazoline derivatives of the present invention provide an anti-tumour effect by way of the selective inhibition of erbB2 receptor tyrosine kinase, compared to EGF receptor tyrosine kinase. It is also believed that the quinazoline derivatives of the present invention exhibit a combination of favourable properties, such as those described hereinbefore.

References to erbB receptors, particularly erbB2, used herein are intended to include both wild-type and mutated receptors unless specifically stated otherwise. The term "mutation" includes, but is not limited to, gene amplification, nucleotide in-frame deletions or substitutions in one or more of the exons that encode receptors such as erbB2.

Generally the quinazoline derivatives of the present invention possess potent inhibitory activity against the erbB receptor tyrosine kinase family, for example by inhibition of EGF and/or erbB2 and/or erbB4 receptor tyrosine kinases, whilst possessing less potent inhibitory activity against other kinases. Furthermore, generally the quinazoline derivatives of the present invention possess substantially better potency against the erbB2 receptor tyrosine kinase over that of the EGFR tyrosine kinase, thus potentially providing effective treatment for erbB2 driven tumours. Accordingly, it may be possible to administer a quinazoline derivative according to the present invention at a dose that is sufficient to inhibit erbB2 tyrosine kinase whilst having no significant effect upon EGFR or other tyrosine kinases. The selective inhibition provided by the quinazoline derivatives according to the present invention may provide treatments for conditions mediated by erbB2 tyrosine kinase, whilst reducing undesirable side effects that may be associated with the inhibition of other tyrosine kinases.

According to a first aspect of the invention there is provided a quinazoline derivative of the Formula I:

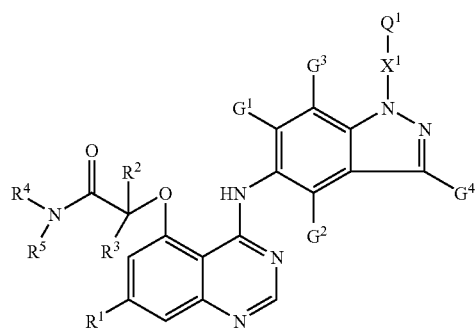

wherein:
$R^1$ is selected from hydrogen, hydroxy, (1-4C)alkoxy and (1-4C)alkoxy(1-4C)alkoxy;

$G^1$, $G^2$, $G^3$ and $G^4$ are each, independently, selected from hydrogen and halogeno;

$X^1$ is selected from $SO_2$, CO, $SO_2N(R^6)$ and $C(R^6)_2$, wherein each $R^6$ is, independently, selected from hydrogen and (1-4C)alkyl;

$Q^1$ is aryl or heteroaryl, which aryl or heteroaryl group optionally bears one or more substituents independently selected from halogeno, cyano, (1-4C)alkoxy and (1-4C)alkyl;

$R^2$ and $R^3$, which may be the same or different, are selected from hydrogen, (2-4C)alkenyl, (2-4C)alkynyl and (1-4C)alkyl, which (1-4C)alkyl optionally bears one or more hydroxy substituents, or $R^2$ and $R^3$ together with the carbon atom to which they are attached form a cyclopropyl ring;

$R^4$ and $R^5$, which may be the same or different, are selected from hydrogen, (3-4C)alkenyl, (3-4C)alkynyl and (1-4C)alkyl, which (1-4C)alkyl optionally bears one or more substituents independently selected from halogeno, cyano, hydroxy, amino, (1-4C)alkylamino, di-[(1-4C)alkyl]amino and (1-4C)alkoxy, or $R^4$ and $R^5$ together with the nitrogen atom to which they are attached form a saturated 4, 5, 6 or 7 membered heterocyclic ring which optionally contains one or more additional heteroatoms independently selected from oxygen, S, SO, $SO_2$ and $N(R^7)$, wherein $R^7$ is selected from hydrogen and (1-4C) alkyl, and wherein any heterocyclic ring formed by $R^4$, $R^5$ and the nitrogen atom to which they are attached optionally bears one or more substituents independently selected from halogeno, cyano, hydroxy, (1-4C)alkyl and (1-4C)alkoxy, and wherein any heterocyclic ring formed by $R^4$, $R^5$ and the nitrogen atom to which they are attached optionally bears 1 or 2 oxo or thioxo substituents;

or a pharmaceutically acceptable salt thereof.

According to a second aspect of the invention there is provided a quinazoline derivative of the Formula I wherein:

$R^1$ is selected from hydrogen, hydroxy, (1-4C)alkoxy and (1-4C)alkoxy(1-4C)alkoxy;

$G^1$, $G^2$, $G^3$ and $G^4$ are each, independently, selected from hydrogen and halogeno;

$X^1$ is selected from $SO_2$, CO, $SO_2N(R^6)$ and $C(R^6)_2$, wherein each $R^6$ is, independently, selected from hydrogen and (1-4C)alkyl;

$Q^1$ is aryl or heteroaryl, which aryl or heteroaryl group optionally bears one or more substituents independently selected from halogeno, cyano, (1-4C)alkoxy and (1-4C)alkyl;

$R^2$ and $R^3$, which may be the same or different, are selected from hydrogen and (1-4C)alkyl, which (1-4C)alkyl optionally bears one or more hydroxy substituents, or $R^2$ and $R^3$ together with the carbon atom to which they are attached form a cyclopropyl ring;

$R^4$ and $R^5$, which may be the same or different, are selected from hydrogen and (1-4C)alkyl, which (1-4C)alkyl optionally bears one or more substituents independently selected from hydroxy, amino, (1-4C)alkylamino, di-[(1-4C)alkyl]amino and (1-4C)alkoxy, or $R^4$ and $R^5$ together with the nitrogen atom to which they are attached form a saturated 4, 5, 6 or 7 membered heterocyclic ring which optionally contains one or more additional heteroatoms independently selected from oxygen, S, SO, $SO_2$ and $N(R^7)$, wherein $R^7$ is selected from hydrogen and (1-4C)alkyl, and wherein any heterocyclic ring formed by $R^4$, $R^5$ and the nitrogen atom to which they are attached optionally bears one or more substituents independently selected from halogeno, cyano, hydroxy, (1-4C)alkyl and (1-4C)alkoxy, and wherein any heterocyclic ring formed by $R^4$, $R^5$ and the nitrogen atom to which they are attached optionally bears 1 or 2 oxo or thioxo substituents;

or a pharmaceutically acceptable salt thereof.

According to a third aspect of the invention there is provided a quinazoline derivative of the Formula I wherein:

$R^1$ is selected from hydrogen, hydroxy, (1-4C)alkoxy and (1-4C)alkoxy(1-4C)alkoxy;

$G^1$, $G^2$, $G^3$ and $G^4$ are each, independently, selected from hydrogen and halogeno;

$X^1$ is $CH_2$;

$Q^1$ is aryl or heteroaryl, which aryl or heteroaryl group optionally bears one or more substituents independently selected from halogeno, cyano, (1-4C)alkoxy and (1-4C)alkyl;

$R^2$ and $R^3$, which may be the same or different, are selected from hydrogen, (2-4C)alkenyl, (2-4C)alkynyl and (1-4C)alkyl, which (1-4C)alkyl optionally bears one or more hydroxy substituents, or $R^2$ and $R^3$ together with the carbon atom to which they are attached form a cyclopropyl ring;

$R^4$ and $R^5$, which may be the same or different, are selected from hydrogen, (3-3C)alkenyl, (3-4C)alkynyl and (1-4C)alkyl, which (1-4C)alkyl optionally bears one or more substituents independently selected from halogeno, cyano, hydroxy, amino, (1-4C)alkylamino, di-[(1-4C)alkyl]amino and (1-4C)alkoxy, or $R^4$ and $R^5$ together with the nitrogen atom to which they are attached form a saturated 4, 5, 6 or 7 membered heterocyclic ring which optionally contains one or more additional heteroatoms independently selected from oxygen, S, SO, $SO_2$ and $N(R^7)$, wherein $R^7$ is selected from hydrogen and (1-4C)alkyl, and wherein any heterocyclic ring formed by $R^4$, $R^5$ and the nitrogen atom to which they are attached optionally bears one or more substituents independently selected from halogeno, cyano, hydroxy, (1-4C)alkyl and (1-4C)alkoxy, and wherein any heterocyclic ring formed by $R^4$, $R^5$ and the nitrogen atom to which they are attached optionally bears 1 or 2 oxo or thioxo substituents;

or a pharmaceutically acceptable salt thereof.

According to a fourth aspect of the invention there is provided a quinazoline derivative of the Formula I wherein:

$R^1$ is selected from hydrogen, hydroxy, (1-4C)alkoxy and (1-4C)alkoxy(1-4C)alkoxy;

$G^1$, $G^2$, $G^3$ and $G^4$ are each, independently, selected from hydrogen and halogeno;

$X^1$ is $CH_2$;

$Q^1$ is aryl or heteroaryl, which aryl or heteroaryl group optionally bears one or more substituents independently selected from halogeno, cyano, (1-4C)alkoxy and (1-4C)alkyl;

$R^2$ and $R^3$, which may be the same or different, are selected from hydrogen and (1-4C)alkyl, which (1-4C)alkyl optionally bears one or more hydroxy substituents, or $R^2$ and $R^3$ together with the carbon atom to which they are attached form a cyclopropyl ring;

$R^4$ and $R^5$, which may be the same or different, are selected from hydrogen and (1-4C)alkyl, which (1-4C)alkyl optionally bears one or more substituents independently selected from hydroxy, amino, (1-4C)alkylamino, di-[(1-4C)alkyl]amino and (1-4C)alkoxy, or $R^4$ and $R^5$ together with the nitrogen atom to which they are attached form a saturated 4, 5, 6 or 7 membered heterocyclic ring which optionally contains one or more additional heteroatoms independently selected from oxygen, S, SO, $SO_2$ and $N(R^7)$, wherein $R^7$ is selected from hydrogen and (1-4C)alkyl, and wherein any heterocyclic ring formed by $R^4$, $R^5$ and the nitrogen atom to which they are attached optionally bears one or more substituents independently selected from halogeno, cyano, hydroxy, (1-4C)alkyl and (1-4C)alkoxy, and wherein any heterocyclic ring formed by $R^4$, $R^5$ and the nitrogen atom to which they are attached optionally bears 1 or 2 oxo or thioxo substituents;

or a pharmaceutically acceptable salt thereof.

According to a fifth aspect of the invention there is provided a quinazoline derivative of the Formula I wherein:

$R^1$ is selected from hydrogen, hydroxy, (1-4C)alkoxy and (1-4C)alkoxy(1-4C)alkoxy;

$G^1$, $G^2$, $G^3$ and $G^4$ are each, independently, selected from hydrogen and halogeno;

$X^1$ is selected from $SO_2$, CO, $SO_2N(R^6)$ and $C(R^6)_2$, wherein each $R^6$ is, independently, selected from hydrogen and (1-4C)alkyl;

$Q^1$ is aryl or heteroaryl, which aryl or heteroaryl group optionally bears one or more substituents independently selected from halogeno, cyano, (1-4C)alkoxy and (1-4C)alkyl;

$R^2$ is hydrogen;

$R^3$ is methyl;

$R^4$ and $R^5$, which may be the same or different, are selected from hydrogen, (3-4C)alkenyl, (3-4)alkynyl and (1-4C)alkyl, which (1-4C)alkyl optionally bears one or more substituents independently selected from halogeno, cyano, hydroxy, amino, (1-4C)alkylamino, di-[(1-4C)alkyl]amino and (1-4C)alkoxy, or $R^4$ and $R^5$ together with the nitrogen atom to which they are attached form a saturated 4, 5, 6 or 7 membered heterocyclic ring which optionally contains one or more additional heteroatoms independently selected from oxygen, S, SO, $SO_2$ and $N(R^7)$, wherein $R^7$ is selected from hydrogen and (1-4C)alkyl, and wherein any heterocyclic ring formed by $R^4$, $R^5$ and the nitrogen atom to which they are attached optionally bears one or more substituents independently selected from halogeno, cyano, hydroxy, (1-4C)alkyl and (1-4C)alkoxy, and wherein any heterocyclic ring formed by $R^4$, $R^5$ and the nitrogen atom to which they are attached optionally bears 1 or 2 oxo or thioxo substituents;

or a pharmaceutically acceptable salt thereof.

According to a sixth aspect of the invention there is provided a quinazoline derivative of the Formula I wherein:

$R^1$ is selected from hydrogen, hydroxy, (1-4C)alkoxy and (1-4C)alkoxy(1-4C)alkoxy;

$G^1$, $G^2$, $G^3$ and $G^4$ are each, independently, selected from hydrogen and halogeno;

$X^1$ is selected from $SO_2$, CO, $SO_2N(R^6)$ and $C(R^6)_2$, wherein each $R^6$ is, independently, selected from hydrogen and (1-4C)alkyl;

$Q^1$ is aryl or heteroaryl, which aryl or heteroaryl group optionally bears one or more substituents independently selected from halogeno, cyano, (1-4C)alkoxy and (1-4C)alkyl;

$R^2$ is hydrogen;

$R^3$ is methyl;

$R^4$ and $R^5$, which may be the same or different, are selected from hydrogen and (1-4C)alkyl, which (1-4C)alkyl optionally bears one or more substituents independently selected from hydroxy, amino, (1-4C)alkylamino, di-[(1-4C)alkyl]amino and (1-4C)alkoxy, or $R^4$ and $R^5$ together with the nitrogen atom to which they are attached form a saturated 4, 5, 6 or 7 membered heterocyclic ring which optionally contains one or more additional heteroatoms independently selected from oxygen, S, SO, $SO_2$ and $N(R^7)$, wherein $R^7$ is selected from hydrogen and (1-4C)alkyl, and wherein any heterocyclic ring formed by $R^4$, $R^5$ and the nitrogen atom to which they are attached optionally bears one or more substituents independently selected from halogeno, cyano, hydroxy, (1-4C)alkyl and (1-4C)alkoxy, and wherein any heterocyclic ring formed by $R^4$, $R^5$ and the nitrogen atom to which they are attached optionally bears 1 or 2 oxo or thioxo substituents;

or a pharmaceutically acceptable salt thereof.

In this specification the generic term "alkyl" includes both straight-chain and branched-chain alkyl groups such as propyl, isopropyl and tert-butyl. However references to individual alkyl groups such as "propyl" are specific for the straight-chain version only, references to individual branched-chain alkyl groups such as "isopropyl" are specific for the branched-chain version only. An analogous convention applies to other generic terms, for example (1-4C)alkoxy includes methoxy and ethoxy, (1-4C)alkylamino includes methylamino, ethylamino and isopropylamino and di-[(1-4C)alkyl]amino includes dimethylamino, diethylamino and N-isopropyl-N-methylamino.

It is to be understood that, insofar as certain of the quinazoline derivatives of the Formula I defined above may exist in optically active or racemic forms by virtue of one or more asymmetric carbon atoms, the invention includes in its definition any such optically active or racemic form which possesses the above-mentioned activity. In particular, the quinazoline derivatives of the Formula I may have a chiral centre on the carbon atom attached to the groups $R^2$ and $R^3$, if the groups $R^2$ and $R^3$ are not identical. The present invention encompasses all such stereoisomers having activity as herein defined, for example the (2R) and (2S) isomers (particularly the (2R) isomers). It is further to be understood that in the names of chiral compounds (R,S) denotes any scalemic or racemic mixture while (R) and (S) denote the enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ratio 50:50. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for $Q^1$ when it is aryl is, for example, phenyl or naphthyl, particularly phenyl.

A suitable value for $Q^1$ when it is heteroaryl is, for example, an aromatic 5 or 6 membered monocyclic ring with up to 4 ring heteroatoms independently selected from oxygen, nitrogen and sulfur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridinyl, pyridazinyl, pyrimidinyl, pyrazinyl or 1,3,5-triazinyl. A particular value for $Q^1$ when it is heteroaryl is, for example, an aromatic 5 or 6 membered monocyclic ring containing nitrogen and, optionally, 1 or 2 (for example 1) additional ring heteroatoms independently selected from oxygen, nitrogen and sulfur, for example pyrrolyl, oxazolyl, isoxazolyl, imidazolyl, pyrazolyl, thiazolyl, isothiazolyl, oxadiazolyl, thiadiazolyl, triazolyl, pyridinyl, pyridazinyl, pyrimidinyl, pyrazinyl or 1,3,5-triazinyl (especially oxazolyl, isoxazolyl, imidazolyl, thiazolyl or pyridinyl, more especially oxazolyl, thiazolyl or pyridinyl).

Where reference is made herein to $R^4$ and $R^5$ together with the nitrogen atom to which they are attached forming a saturated 4, 5, 6 or 7 membered heterocyclic ring which optionally contains one or more additional heteroatoms independently selected from oxygen, S, SO, $SO_2$ or $N(R^7)$ (wherein $R^7$ is as hereinbefore defined), the ring so formed suitably contains one or two additional heteroatoms and, more suitably contains one additional heteroatom. For example, the ring so formed may be selected from azetidin-1-yl, pyrrolidin-1-yl, pyrazolidin-1-yl, piperidin-1-yl, morpholin-4-yl and piperazin-1-yl (particularly azetidin-1-yl, pyrrolidin-1-yl, piperidin-1-yl, morpholin-4-yl and piperazin-1-yl). Any of the heterocyclic rings formed by $R^4$ and $R^5$ together with the nitrogen atom to which they are attached optionally bears one or more substituents, which may be the same or different, as defined herein and/or optionally bears 1 or 2 oxo or thioxo substituents.

It is to be understood that the quinazoline group in the Formula I is unsubstituted at each of the 2-, 6- and 8-positions on the quinazoline ring.

Suitable values for any of the 'R' groups ($R^1$ to $R^7$), for any of the 'G' groups ($G^1$ to $G^4$) or for various groups within a $Q^1$ or $X^1$ group include:—

| | |
|---|---|
| for halogeno | fluoro, chloro, bromo and iodo; |
| for (1-4C)alkyl: | methyl, ethyl, propyl, isopropyl and tert-butyl; |
| for (2-4C)alkenyl: | vinyl, isopropenyl, allyl and but-2-enyl; |
| for (2-4C)alkynyl: | ethynyl, 2-propynyl and but-2-ynyl; |
| for (1-4C)alkoxy: | methoxy, ethoxy, propoxy, isopropoxy and butoxy; |
| for (1-4C)alkoxy(1-4C)alkoxy | ethoxymethoxy, propoxymethoxy, methoxyethoxy, ethoxyethoxy, methoxypropoxy, ethoxypropoxy, methoxyisopropoxy and methoxybutoxy; |
| for (1-4C)alkylamino: | methylamino, ethylamino, propylamino, isopropylamino and butylamino; and |
| for di-[(1-4C)alkyl]amino: | dimethylamino, diethylamino, N-ethyl-N-methylamino and di-isopropylamino. |

When in this specification reference is made to a (1-4C) alkyl group it is to be understood that such groups refer to alkyl groups containing up to 4 carbon atoms. Similarly, reference to a (1-2C)alkyl group refers to alkyl groups containing up to 2 carbon atoms such as methyl and ethyl. A similar convention is adopted for the other groups listed above.

When, as defined hereinbefore, in the group of the formula —$X^1$-$Q^1$, $X^1$ is, for example, a $SO_2N(R^6)$ linking group, it is the $SO_2$ group of the $SO_2N(R^6)$ linking group which is attached to the indazole group in the Formula I and the nitrogen atom of the $SO_2N(R^6)$ linking group which is attached to the $Q^1$ group.

It is to be understood that certain quinazoline derivatives of the Formula I may exist in solvated as well as unsolvated forms such as, for example, hydrated forms. It is to be understood that the invention encompasses all such solvated forms which exhibit an inhibitory effect on an erbB receptor tyrosine kinase, such as anti-proliferative activity.

It is also to be understood that certain quinazoline derivatives of the Formula I may exhibit polymorphism, and that the invention encompasses all such forms which exhibit an inhibitory effect on an erbB receptor tyrosine kinase, such as anti-proliferative activity.

It is also to be understood that the invention relates to all tautomeric forms of the quinazoline derivatives of the Formula I which exhibit an inhibitory effect on an erbB receptor tyrosine kinase, such as anti-proliferative activity.

A suitable pharmaceutically acceptable salt of a quinazoline derivative of the Formula I is, for example, an acid-addition salt of a quinazoline derivative of the Formula I, for example an acid-addition salt with an inorganic or organic acid. Suitable inorganic acids include, for example, hydrochloric, hydrobromic or sulfuric acid. Suitable organic acids include, for example, trifluoroacetic, citric or maleic acid. Another suitable pharmaceutically acceptable salt of a quinazoline derivative of the Formula I is for example, a salt of a quinazoline derivative of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel quinazoline derivatives of the invention include, for example, quinazoline derivatives of the Formula I, or pharmaceutically acceptable salts thereof, wherein, unless otherwise stated, each of $R^1$, $R^2$, $R^3$, $R^4$, $R^5$, $G^1$, $G^2$, $G^3$, $G^4$, $Q^1$ and $X^1$ has any of the meanings defined hereinbefore or in paragraphs (a) to (eeee) hereinafter:—

(a) $R^1$ is selected from hydrogen, hydroxy, methoxy, ethoxy and methoxyethoxy;

(b) $R^1$ is selected from hydrogen and methoxy;

(c) $R^1$ is hydrogen;

(d) $G^1$, $G^2$, $G^3$ and $G^4$ are each, independently, selected from hydrogen, chloro and fluoro (particularly hydrogen and fluoro);

(e) $G^1$, $G^2$, $G^3$ and $G^4$ are all hydrogen;

(f) $X^1$ is $C(R^6)_2$, wherein each $R^6$ is, independently, hydrogen or (1-4C)alkyl (such as (1-2C)alkyl);

(g) $X^1$ is $CH_2$;

(h) $Q^1$ is selected from phenyl and a 5 or 6 membered monocyclic heteroaryl ring, which ring contains 1, 2 or 3 heteroatoms independently selected from oxygen, nitrogen and sulfur, which phenyl or heteroaryl group optionally bears 1, 2 or 3 substituents (for example 1 or 2) independently selected from halogeno, cyano, (1-4C)alkyl and (1-4C)alkoxy;

(i) $Q^1$ is selected from phenyl and a 5 or 6 membered monocyclic heteroaryl ring, which ring contains 1, 2 or 3 heteroatoms independently selected from oxygen, nitrogen and sulfur, which phenyl or heteroaryl group optionally bears 1, 2 or 3 substituents (for example 1 or 2) independently selected from chloro, fluoro, cyano, (1-2C)alkyl and (1-2C)alkoxy (especially fluoro and methyl);

(j) $Q^1$ is selected from phenyl and a 5 or 6 membered monocyclic heteroaryl ring, which ring contains 1, 2 or 3 heteroatoms independently selected from oxygen, nitrogen and sulfur, which phenyl or heteroaryl group optionally bears 1, 2 or 3 substituents (for example 1 or 2) independently selected from fluoro, cyano, methyl and methoxy;

(k) $Q^1$ is phenyl, which phenyl group optionally bears 1, 2 or 3 substituents (for example 1 or 2) as hereinbefore defined in (h), (i) or (j);

(l) $Q^1$ is phenyl, which phenyl group optionally bears 1 or 2 substituents independently selected from chloro and fluoro;

(m) $Q^1$ is phenyl, which phenyl group bears 1 or 2 substituents independently selected from chloro and fluoro;

(n) $Q^1$ is phenyl, which phenyl group optionally bears 1 or 2 substituents independently selected from fluoro, cyano, methyl and methoxy (especially fluoro, cyano and methoxy);

(o) $Q^1$ is phenyl, which phenyl group bears 1 or 2 (particularly 1) fluoro substituents;

(p) $Q^1$ is 3-fluorophenyl;

(q) $Q^1$ is 3-methoxyphenyl;

(r) $Q^1$ is 2-cyanophenyl;

(s) $Q^1$ is a 5 or 6 membered monocyclic heteroaryl ring, which ring contains 1 nitrogen heteroatom and optionally 1 additional heteroatom selected from oxygen, nitrogen and sulfur, which heteroaryl group optionally bears 1, 2 or 3 substituents (for example 1 or 2) as hereinbefore defined in (h), (i) or (j);

(t) $Q^1$ is selected from phenyl, pyridinyl, pyrazinyl, 1,3-thiazolyl, 1H-imidazolyl, 1H-pyrazolyl, 1,3-oxazolyl and isoxazolyl, which optionally bears 1, 2 or 3 substituents (for example 1 or 2) as hereinbefore defined in (h), (i) or (j);

(u) $Q^1$ is selected from phenyl, pyridinyl, pyrazinyl, 1,3-thiazolyl and isoxazolyl (particularly phenyl, pyridinyl and 1,3-thiazolyl), which optionally bears 1, 2 or 3 substituents (for example 1 or 2) as hereinbefore defined in (h), (i) or (j);

(v) $Q^1$ is selected from phenyl, pyridinyl, 1,3-thiazolyl, 1H-imidazolyl, 1,3-oxazolyl and isoxazolyl (particularly phenyl, pyridinyl and 1,3-thiazolyl), which optionally bears 1, 2 or 3 substituents (for example 1 or 2) as hereinbefore defined in (h), (i) or (j);

(w) $Q^1$ is selected from phenyl, pyridinyl, 1,3-thiazolyl and 1,3-oxazolyl, which optionally bears 1, 2 or 3 substituents (for example 1 or 2) as hereinbefore defined in (h), (i) or (j);

(x) $Q^1$ is selected from 2-, 3- or 4-pyridinyl, 2-pyrazinyl, 1,3-thiazol-2-yl, 1,3-thiazol-4-yl, 1,3-thiazol-5-yl, 3-isoxazolyl, 4-isoxazolyl and 5-isoxazolyl, which optionally bears 1, 2 or 3 substituents (for example 1 or 2) as hereinbefore defined in (h), (i) or (j);

(y) $Q^1$ is selected from 2-, 3- or 4-pyridinyl, 1,3-thiazol-2-yl, 1,3-thiazol-4-yl, 1,3-thiazol-5-yl, 1H-imidazol-2-yl, 1,3-oxazol-2-yl, 3-isoxazolyl, 4-isoxazolyl and 5-isoxazolyl, which optionally bears 1, 2 or 3 substituents (for example 1 or 2) as hereinbefore defined in (h), (i) or (j);

(z) $Q^1$ is selected from phenyl, 2- or 3-pyridinyl, 1,3-thiazol-2-yl, 1,3-thiazol-4-yl, 1,3-thiazol-5-yl and 1,3-oxazol-2-yl, which optionally bears 1, 2 or 3 substituents (for example 1 or 2) as hereinbefore defined in (h), (i) or (j);

(aa) $Q^1$ is selected from phenyl, 2-pyridinyl, 1,3-thiazol-2-yl and 1,3-thiazol-4-yl (particularly phenyl, 2-pyridinyl and 1,3-thiazol-4-yl), which optionally bears 1, 2 or 3 substituents (for example 1 or 2) as hereinbefore defined in (h), (i) or (j);

(bb) $Q^1$ is pyridinyl (particularly 2-pyridinyl or 3-pyridinyl), which optionally bears 1, 2 or 3 substituents (for example 1 or 2) as hereinbefore defined in (h), (i) or (j);

(cc) $Q^1$ is 2-pyridinyl, which optionally bears 1 or 2 substituents independently selected from fluoro, chloro and (1-2C)alkoxy (particularly fluoro);

(dd) $Q^1$ is 3-pyridinyl, which optionally bears 1 or 2 substituents independently selected from fluoro, chloro and (1-2C)alkoxy (particularly fluoro);

(ee) $Q^1$ is 2-pyridinyl;

(ff) $Q^1$ is 6-fluoro-pyridin-3-yl;

(gg) $Q^1$ is 1,3-thiazolyl (particularly 1,3-thiazol-2-yl, 1,3-thiazol-4-yl or 1,3-thiazolyl-5-yl), which optionally bears 1 or 2 substituents (for example 1) as hereinbefore defined in (h), (i) or (j);

(hh) $Q^1$ is 1,3-thiazol-4-yl, which optionally bears 1 or 2 substituents independently selected from fluoro, chloro, (1-2C)alkyl and (1-2C)alkoxy (particularly methyl);

(ii) $Q^1$ is 1,3-thiazol-2-yl, which optionally bears 1 or 2 substituents independently selected from fluoro, chloro, (1-2C)alkyl and (1-2C)alkoxy (particularly methyl);

(jj) $Q^1$ is 1,3-thiazol-5-yl, which optionally bears 1 or 2 substituents independently selected from fluoro, chloro, (1-2C)alkyl and (1-2C)alkoxy (particularly methyl);

(kk) $Q^1$ is 1,3-thiazol-4-yl;

(ll) $Q^1$ is 1,3-thiazol-2-yl;

(mm) $Q^1$ is 1,3-thiazol-5-yl;

(nn) $Q^1$ is 2-methyl-1,3-thiazol-5-yl;

(oo) $Q^1$ is 1,3-oxazolyl (particularly 1,3-oxazol-2-yl), which optionally bears 1 or 2 substituents (for example 1) as hereinbefore defined in (h), (i) or (j);

(pp) $Q^1$ is 1,3-oxazol-2-yl;

(qq) $Q^1$ is isoxazolyl (particularly isoxazol-3-yl), which optionally bears 1 or 2 substituents (for example 1) as hereinbefore defined in (h), (i) or (j);

(rr) $Q^1$ is 5-methyl-isoxazol-3-yl;

(ss) $Q^1$ is 3,5-dimethyl-isoxazol-4-yl;

(tt) $Q^1$ is 1H-imidazolyl (particularly 1H-imidazol-2-yl), which optionally bears 1 or 2 substituents (for example 1) as hereinbefore defined in (h), (i) or (j);

(uu) $Q^1$ is 1-methyl-imidazol-2-yl;

(vv) $Q^1$ is selected from 3-fluorophenyl, 2-pyridinyl, 6-fluoro-pyridin-3-yl, 1,3-thiazol-5-yl, 1,3-thiazol-4-yl, 1,3-thiazol-2-yl, 2-methyl-1,3-thiazol-5-yl, 1,3-oxazol-2-yl, 5-methyl-isoxazol-3-yl, 3,5-dimethylisoxazol-4-yl and 1-methyl-imidazol-2-yl;

(ww) $Q^1$ is selected from 3-fluorophenyl, 3-methoxyphenyl, 2-cyanophenyl, 2-pyridinyl, 6-fluoro-pyridin-3-yl, 1,3-thiazol-4-yl, 1,3-thiazol-2-yl, 2-methyl-1,3-thiazol-5-yl and 1,3-oxazol-2-yl;

(xx) $Q^1$ is selected from phenyl, pyridinyl, 1,3-thiazolyl, 1H-imidazolyl, 1,3-oxazolyl and isoxazolyl (particularly phenyl, pyridinyl and 1,3-thiazolyl), which optionally bears 1, 2 or 3 substituents (for example 1 or 2) as hereinbefore defined in (h), (i) or (j); and
  $X^1$ is $C(R^6)_2$, wherein each $R^6$ is, independently, hydrogen or (1-2C)alkyl (particularly each $R^6$ is hydrogen);

(yy) $Q^1$ is selected from phenyl, pyridinyl, 1,3-thiazolyl and 1,3-oxazolyl, which optionally bears 1, 2 or 3 substituents (for example 1 or 2) as hereinbefore defined in (h), (i) or (j); and
  $X^1$ is $C(R^6)_2$, wherein each $R^6$ is, independently, hydrogen or (1-2C)alkyl (particularly each $R^6$ is hydrogen);

(zz) $Q^1$ is selected from phenyl, pyridinyl, 1,3-thiazolyl, 1H-imidazolyl, 1,3-oxazolyl and isoxazolyl (particularly phenyl, pyridinyl and 1,3-thiazolyl), which optionally bears 1, 2 or 3 substituents (for example 1 or 2) as hereinbefore defined in (h), (i) or (j);
  $X^1$ is $C(R^6)_2$, wherein each $R^6$ is, independently, hydrogen or (1-2C)alkyl (particularly each $R^6$ is hydrogen); and
  $G^1$, $G^2$, $G^3$ and $G^4$ are all hydrogen;

(aaa) $Q^1$ is selected from phenyl, pyridinyl, 1,3-thiazolyl and 1,3-oxazolyl, which optionally bears 1, 2 or 3 substituents (for example 1 or 2) as hereinbefore defined in (h), (i) or (j);
  $X^1$ is $C(R^6)_2$, wherein each $R^6$ is, independently, hydrogen or (1-2C)alkyl (particularly each $R^6$ is hydrogen); and
  $G^1$, $G^2$, $G^3$ and $G^4$ are all hydrogen;

(bbb) the group —$X^1$-$Q^1$ is selected from pyridin-2-ylmethyl, 1,3-thiazol-2-ylmethyl, 1,3-thiazol-4-ylmethyl and 3-fluorobenzyl (particularly pyridin-2-ylmethyl, 1,3-thiazol-4-ylmethyl and 3-fluorobenzyl);

(ccc) the group —$X^1$-$Q^1$ is selected from 3-fluorobenzyl, 3-methoxybenzyl, 2-cyanobenzyl, pyridin-2-ylmethyl, (6-fluoro-pyridin-3-yl)methyl, 1,3-thiazol-4-ylmethyl, 1,3-thiazol-2-ylmethyl, (2-methyl-1,3-thiazol-5-yl)methyl and 1,3-oxazol-2-ylmethyl;

(ddd) the group —$X^1$-$Q^1$ is 3-methoxybenzyl;

(eee) the group —$X^1$-$Q^1$ is 2-cyanobenzyl;

(fff) the group —$X^1$-$Q^1$ is (6-fluoro-pyridin-3-yl)methyl;

(ggg) the group —X¹-Q¹ is 1,3-thiazol-2-ylmethyl;

(hhh) the group —X¹-Q¹ is (2-methyl-1,3-thiazol-5-yl)methyl;

(iii) the group —X¹-Q¹ is 1,3-oxazol-2-ylmethyl;

(jjj) the group —X¹-Q¹ is pyridin-2-ylmethyl;

(kkk) the group —X¹-Q¹ is 1,3-thiazol-4-ylmethyl;

(lll) the group —X¹-Q¹ is 3-fluorobenzyl;

(mmm) $R^2$ and $R^3$ are each, independently, selected from hydrogen and (1-2C)alkyl (such as methyl);

(nnn) $R^2$ and $R^3$ are each, independently, selected from hydrogen and (1-2C)alkyl, wherein at least one of $R^2$ and $R^3$ is (1-2C)alkyl (such as methyl);

(ooo) $R^2$ is hydrogen and $R^3$ is (1-2C)alkyl (such as methyl);

(ppp) $R^2$ and $R^3$ are both hydrogen;

(qqq) $R^4$ and $R^5$, which may be the same or different, are selected from hydrogen and (1-4C)alkyl, which (1-4C)alkyl optionally bears one or more hydroxy substituents, or $R^4$ and $R^5$ together with the nitrogen atom to which they are attached form a saturated 4, 5, 6 or 7 (particularly 5 or 6) membered heterocyclic ring which optionally contains one or more additional heteroatoms independently selected from oxygen, S, SO, $SO_2$ and $N(R^7)$, wherein $R^7$ is selected from hydrogen and (1-2C)alkyl, and wherein any heterocyclic ring formed by $R^4$, $R^5$ and the nitrogen atom to which they are attached optionally bears one or more substituents independently selected from halogeno, cyano, hydroxy, (1-4C)alkyl and (1-4C)alkoxy, and wherein any heterocyclic ring formed by $R^4$, $R^5$ and the nitrogen atom to which they are attached optionally bears 1 or 2 oxo or thioxo substituents;

(rrr) $R^4$ and $R^5$, which may be the same or different, are selected from hydrogen and (1-4C)alkyl, which (1-4C)alkyl optionally bears one or more hydroxy substituents, or $R^4$ and $R^5$ together with the nitrogen atom to which they are attached form a heterocyclic ring selected from azetidin-1-yl, pyrrolidin-1-yl, pyrazolidin-1-yl, piperidin-1-yl, morpholin-4-yl and piperazin-1-yl, wherein any heterocyclic ring optionally bears one or more substituents independently selected from halogeno, cyano, hydroxy, (1-4C)alkyl and (1-4C)alkoxy, and wherein any heterocyclic ring optionally bears 1 or 2 oxo or thioxo substituents;

(sss) $R^4$ and $R^5$, which may be the same or different, are selected from hydrogen and (1-4C)alkyl, which (1-4C)alkyl optionally bears one or more hydroxy substituents, or $R^4$ and $R^5$ together with the nitrogen atom to which they are attached form a heterocyclic ring selected from pyrrolidin-1-yl and morpholin-4-yl, wherein any heterocyclic ring optionally bears one or more substituents independently selected from halogeno, cyano, hydroxy, (1-4C)alkyl and (1-4C)alkoxy, and wherein any heterocyclic ring optionally bears 1 or 2 oxo or thioxo substituents;

(ttt) $R^4$ is hydrogen and $R^5$ is (1-4C)alkyl, which (1-4C)alkyl optionally bears one or more hydroxy substituents;

(uuu) $R^4$ and $R^5$ are independently selected from hydrogen, methyl, ethyl and 2-hydroxyethyl;

(vvv) $R^4$ is hydrogen and $R^5$ is selected from hydrogen, methyl, ethyl and 2-hydroxyethyl;

(www) $R^4$ is hydrogen and $R^5$ is selected from methyl, ethyl and 2-hydroxyethyl;

(xxx) $R^4$ and $R^5$ are both (1-4C)alkyl, which (1-4C)alkyl optionally bears one or more hydroxy substituents;

(yyy) $R^4$ is methyl and $R^5$ is (1-4C)alkyl, which (1-4C)alkyl optionally bears one or more hydroxy substituents;

(zzz) $R^4$ is methyl and $R^5$ is selected from methyl, ethyl and 2-hydroxyethyl;

(aaaa) $R^4$ and $R^5$ are both methyl;

(bbbb) $R^4$ and $R^5$ together with the nitrogen atom to which they are attached form a heterocyclic ring selected from pyrrolidin-1-yl and morpholin-4-yl, which heterocyclic ring optionally bears one or more substituents independently selected from halogeno, cyano, hydroxy, (1-4C)alkyl and (1-4C)alkoxy, and which heterocyclic ring optionally bears 1 or 2 oxo or thioxo substituents;

(cccc) $R^4$ and $R^5$ together with the nitrogen atom to which they are attached form a heterocyclic ring selected from pyrrolidin-1-yl and morpholin-4-yl;

(dddd) $Q^1$ is selected from phenyl, 2-pyridinyl and 1,3-thiazol-2-yl, which optionally bears 1, 2 or 3 substituents (for example 1 or 2) as hereinbefore defined in (h), (i) or (j); and (eeee) the group —X¹-Q¹ is selected from pyridin-2-ylmethyl, 1,3-thiazol-2-ylmethyl and 3-fluorobenzyl.

An embodiment of the present invention is a quinazoline derivative of the Formula I wherein:

$R^1$ is selected from hydrogen and (1-2C)alkoxy (for example $R^1$ is hydrogen or methoxy, particularly hydrogen);

$X^1$ is $CH_2$;

$Q^1$ is aryl or heteroaryl, which aryl or heteroaryl group optionally bears one or more substituents (for example 1 or 2) independently selected from chloro, fluoro, cyano, (1-2C)alkyl and (1-2C)alkoxy (especially fluoro, cyano, methyl and methoxy);

and wherein $G^1$, $G^2$, $G^3$, $G^4$, $R^2$, $R^3$, $R^4$ and $R^5$ have any of the values defined hereinbefore;

or a pharmaceutically acceptable salt thereof.

In this embodiment, a particular value for $Q^1$ is phenyl or a 5 or 6 membered heteroaryl ring containing 1 nitrogen heteroatom and optionally 1 additional heteroatom independently selected from oxygen, nitrogen and sulfur, which phenyl or heteroaryl group optionally bears 1, 2 or 3 substituents as hereinbefore defined.

Another embodiment of the present invention is a quinazoline derivative of the Formula I wherein:

$R^1$ is selected from hydrogen and (1-2C)alkoxy (for example $R^1$ is hydrogen or methoxy, particularly hydrogen);

$X^1$ is $CH_2$;

$Q^1$ is heteroaryl, which heteroaryl group optionally bears one or more substituents (for example 1 or 2) independently selected from chloro, fluoro, cyano, (1-2C)alkyl and (1-2C)alkoxy (especially fluoro, cyano, methyl and methoxy, more especially fluoro and methyl);

and wherein $G^1$, $G^2$, $G^3$, $G^4$, $R^2$, $R^3$, $R^4$ and $R^5$ have any of the values defined hereinbefore;

or a pharmaceutically acceptable salt thereof.

In this embodiment, a particular value for $Q^1$ is a 5 or 6 membered heteroaryl ring containing 1 nitrogen heteroatom and optionally 1 additional heteroatom independently selected from oxygen, nitrogen and sulfur, which heteroaryl group optionally bears 1, 2 or 3 substituents as hereinbefore defined.

Another embodiment of the present invention is a quinazoline derivative of the Formula I wherein:

R$^1$ is selected from hydrogen and (1-2C)alkoxy (for example R$^1$ is hydrogen or methoxy, particularly hydrogen);

X$^1$ is CH$_2$;

Q$^1$ is phenyl or a 5 or 6 membered heteroaryl ring containing 1 nitrogen heteroatom and optionally 1 additional heteroatom independently selected from oxygen, nitrogen and sulfur, which phenyl or heteroaryl ring optionally bears one or more substituents independently selected from halogeno, cyano, (1-4C)alkoxy and (1-4C)alkyl;

R$^4$ and R$^5$, which may be the same or different, are selected from hydrogen and (1-2C)alkyl, which (1-2C)alkyl optionally bears one or more hydroxy substituents, or R$^4$ and R$^5$ together with the nitrogen atom to which they are attached form a heterocyclic ring selected from azetidin-1-yl, pyrrolidin-1-yl, pyrazolidin-1-yl, piperidin-1-yl, morpholin-4-yl and piperazin-1-yl, wherein any heterocyclic ring optionally bears one or more substituents independently selected from halogeno, cyano, hydroxy, (1-4C)alkyl and (1-4C)alkoxy, and wherein any heterocyclic ring optionally bears 1 or 2 oxo or thioxo substituents;

and wherein G$^1$, G$^2$, G$^3$, G$^4$, R$^2$ and R$^3$ have any of the values defined hereinbefore;

or a pharmaceutically acceptable salt thereof.

In this embodiment, a particular value for Q$^1$ is phenyl, pyridinyl, 1,3-thiazolyl, 1H-imidazolyl, 1,3-oxazolyl or isoxazolyl, wherein Q$^1$ optionally bears 1, 2 or 3 substituents as hereinbefore defined.

Another embodiment of the present invention is a quinazoline derivative of the Formula I wherein:

R$^1$ is selected from hydrogen and methoxy (particularly R$^1$ is hydrogen);

X$^1$ is CH$_2$;

Q$^1$ is phenyl or a 5 or 6 membered heteroaryl ring containing 1 nitrogen heteroatom and optionally 1 additional heteroatom independently selected from oxygen, nitrogen and sulfur (particularly nitrogen and sulfur), which phenyl or heteroaryl ring optionally bears one or more substituents independently selected from halogeno, cyano, (1-4C)alkoxy and (1-4C)alkyl;

R$^4$ and R$^5$, which may be the same or different, are selected from hydrogen and (1-2C)alkyl, which (1-2C)alkyl optionally bears one or more hydroxy substituents, or R$^4$ and R$^5$ together with the nitrogen atom to which they are attached form a morpholin-4-yl ring;

and wherein G$^1$, G$^2$, G$^1$, G$^4$, R$^2$ and R$^3$ have any of the values defined hereinbefore;

or a pharmaceutically acceptable salt thereof.

In this embodiment, a particular value for Q$^1$ is phenyl, pyridinyl, 1,3-thiazolyl or 1,3-oxazolyl (particularly phenyl, pyridinyl or 1,3-thiazolyl, for example phenyl, pyridin-2-yl or 1,3-thiazol-2-yl), wherein Q$^1$ optionally bears 1, 2 or 3 substituents as hereinbefore defined. Particular substituents for Q$^1$ include fluoro, methyl, methoxy and cyano (especially fluoro).

In this embodiment, R$^2$ and R$^3$, which may be the same or different, may in particular be selected from hydrogen and (1-2C)alkyl.

In this embodiment G$^1$, G$^2$, G$^3$, G$^4$ may in particular be hydrogen.

Another embodiment of the present invention is a quinazoline derivative of the Formula I wherein:

R$^1$ is selected from hydrogen and methoxy (particularly R$^1$ is hydrogen);

X$^1$ is CH$_2$;

Q$^1$ is selected from phenyl, pyridinyl and 1,3-thiazolyl (for example phenyl, pyridin-2-yl or 1,3-thiazol-2-yl), wherein Q$^1$ optionally bears a substituent selected from fluoro, methyl, methoxy and cyano (for example fluoro);

R$^4$ and R$^5$ are independently (1-2C)alkyl (for example R$^4$ and R$^5$ are both methyl), or R$^4$ and R$^5$ together with the nitrogen atom to which they are attached form a morpholin-4-yl ring;

G$^1$, G$^2$, G$^3$, G$^4$ are hydrogen;

R$^2$ is (1-2C)alkyl (for example methyl);

and R$^3$ is hydrogen;

or a pharmaceutically acceptable salt thereof.

Particular quinazoline derivatives of the invention are, for example, one or more quinazoline derivatives of the Formula I selected from:

(2R)—N-(2-hydroxyethyl)-N-methyl-2-[(4-{[1-(pyridin-2-ylmethyl)-1H-indazol-5-yl]amino}quinazolin-5-yl)oxy] propanamide;

5-[(1R)-1-methyl-2-morpholin-4-yl-2-oxoethoxy]-N-[1-(pyridin-2-ylmethyl)-1H-indazol-5-yl]quinazolin-4-amine;

(2R)—N,N-dimethyl-2-[(4-{[1-(pyridin-2-ylmethyl)-1H-indazol-5-yl]amino}quinazolin-5-yl)oxy]propanamide;

(2S)—N,N-dimethyl-2-[(4-{[1-(pyridin-2-ylmethyl)-1H-indazol-5-yl]amino}quinazolin-5-yl)oxy]propanamide;

(2R)-2-[(4-{[1-(pyridin-2-ylmethyl)-1H-indazol-5-yl] amino}quinazolin-5-yl)oxy]propanamide;

(2R)—N-methyl-2-[(4-{[1-(pyridin-2-ylmethyl)-1H-indazol-5-yl]amino}quinazolin-5-yl)oxy]propanamide;

(2R)—N-ethyl-2-[(4-{[1-(pyridin-2-ylmethyl)-1H-indazol-5-yl]amino}quinazolin-5-yl)oxy]propanamide;

5-[(1R)-1-methyl-2-oxo-2-pyrrolidin-1-ylethoxy]-N-[1-(pyridin-2-ylmethyl)-1H-indazol-5-yl]quinazolin-4-amine;

(2R)—N-(2-hydroxyethyl)-2-[(4-{[1-(pyridin-2-ylmethyl)-1H-indazol-5-yl]amino}quinazolin-5-yl)oxy]propanamide;

N,N-dimethyl-2-[(4-{[1-(pyridin-2-ylmethyl)-1H-indazol-5-yl]amino}quinazolin-5-yl)oxy]acetamide;

2-[(4-{[1-(pyridin-2-ylmethyl)-1H-indazol-5-yl] amino}quinazolin-5-yl)oxy]acetamide;

N-ethyl-2-[(4-{[1-(pyridin-2-ylmethyl)-1H-indazol-5-yl] amino}quinazolin-5-yl)oxy]acetamide;

N-(2-hydroxyethyl)-2-[(4-{[1-(pyridin-2-ylmethyl)-1H-indazol-5-yl]amino}quinazolin-5-yl)oxy]acetamide;

N-methyl-2-[(4-{[1-(pyridin-2-ylmethyl)-1H-indazol-5-yl] amino}quinazolin-5-yl)oxy]acetamide;

N-(2-hydroxyethyl)-N-methyl-2-[(4-{[1-(pyridin-2-ylmethyl)-1H-indazol-5-yl]amino}quinazolin-5-yl)oxy]acetamide;

5-(2-oxo-2-pyrrolidin-1-ylethoxy)-N-[1-(pyridin-2-ylmethyl)-1H-indazol-5-yl]quinazolin-4-amine;

5-(2-morpholin-4-yl-2-oxoethoxy)-N-[1-(pyridin-2-ylmethyl)-1H-indazol-5-yl]quinazolin-4-amine;

(2R)—N,N-dimethyl-2-[(4-{[1-(1,3-thiazol-4-ylmethyl)-1H-indazol-5-yl]amino}quinazolin-5-yl)oxy]propanamide;

(2R)-2-[(4-{[1-(3-fluorobenzyl)-1H-indazol-5-yl] amino}quinazolin-5-yl)oxy]-N,N-dimethylpropanamide;

(2R)—N,N-dimethyl-2-[(4-{[1-(1,3-thiazol-2-ylmethyl)-1H-indazol-5-yl]amino}quinazolin-5-yl)oxy]propanamide;

(2R)—N,N-dimethyl-2-{[4-({1-[(2-methyl-1,3-thiazol-5-yl)methyl]-1H-indazol-5-yl}amino)quinazolin-5-yl] oxy}propanamide;

(2R)-2-{[4-({1-[(6-fluoropyridin-3-yl)methyl]-1H-indazol-5-yl}amino)quinazolin-5-yl]oxy}-N,N-dimethylpropanamide;

(2R)-2-[(4-{[1-(3-methoxybenzyl)-1H-indazol-5-yl] amino}quinazolin-5-yl)oxy]-N,N-dimethylpropanamide;

(2R)-2-[(4-{[1-(2-cyanobenzyl)-1H-indazol-5-yl]amino}quinazolin-5-yl)oxy]-N,N-dimethylpropanamide;
(2R)—N,N-dimethyl-2-[(4-{[1-(1,3-oxazol-2-ylmethyl)-1H-indazol-5-yl]amino}quinazolin-5-yl)oxy]propanamide;
(2S)-2-[(4-{[1-(3-fluorobenzyl)-1H-indazol-5-yl]amino}quinazolin-5-yl)oxy]-N,N-dimethylpropanamide;
N-[1-(3-fluorobenzyl)-1H-indazol-5-yl]-5-[(1S)-1-methyl-2-oxo-2-pyrrolidin-1-ylethoxy]-quinazolin-4-amine;
(2S)-2-[(4-{[1-(3-fluorobenzyl)-1H-indazol-5-yl]amino}quinazolin-5-yl)oxy]propanamide;
N-[1-(3-fluorobenzyl)-1H-indazol-5-yl]-5-[(1R)-1-methyl-2-oxo-2-pyrrolidin-1-ylethoxy]-quinazolin-4-amine;
(2R)-2-[(4-{[1-(3-fluorobenzyl)-1H-indazol-5-yl]amino}quinazolin-5-yl)oxy]propanamide;
5-[(1S)-1-methyl-2-oxo-2-pyrrolidin-1-ylethoxy]-N-[1-(pyridin-2-ylmethyl)-1H-indazol-5-yl]quinazolin-4-amine;
(2S)-2-[(4-{[1-(pyridin-2-ylmethyl)-1H-indazol-5-yl]amino}quinazolin-5-yl)oxy]propanamide;
5-[(1S)-1-methyl-2-oxo-2-pyrrolidin-1-ylethoxy]-N-[1-(1,3-thiazol-2-ylmethyl)-1H-indazol-5-yl]quinazolin-4-amine;
(2S)—N,N-dimethyl-2-[(4-{[1-(1,3-thiazol-2-ylmethyl)-1H-indazol-5-yl]amino}quinazolin-5-yl)oxy]propanamide;
(2S)-2-[(4-{[1-(1,3-thiazol-2-ylmethyl)-1H-indazol-5-yl]amino}quinazolin-5-yl)oxy]propanamide;
5-[(1R)-1-methyl-2-oxo-2-pyrrolidin-1-ylethoxy]-N-[1-(1,3-thiazol-2-ylmethyl)-1H-indazol-5-yl]quinazolin-4-amine;
(2R)-2-[(4-{[1-(1,3-thiazol-2-ylmethyl)-1H-indazol-5-yl]amino}quinazolin-5-yl)oxy]propanamide;
(2R)-2-[(4-{[1-(1,3-thiazol-4-ylmethyl)-1H-indazol-5-yl]amino}quinazolin-5-yl)oxy]propanamide;
(2R)—N-methyl-2-[(4-{[1-(1,3-thiazol-4-ylmethyl)-1H-indazol-5-yl]amino}quinazolin-5-yl)oxy]propanamide;
(2R)—N-ethyl-2-[(4-{[1-(1,3-thiazol-4-ylmethyl)-1H-indazol-5-yl]amino}quinazolin-5-yl)oxy]propanamide;
5-[(1R)-1-methyl-2-oxo-2-pyrrolidin-1-ylethoxy]-N-[1-(1,3-thiazol-4-ylmethyl)-1H-indazol-5-yl]quinazolin-4-amine;
(2R)—N-(2-hydroxyethyl)-N-methyl-2-[(4-{[1-(1,3-thiazol-4-ylmethyl)-1H-indazol-5-yl]amino}quinazolin-5-yl)oxy]propanamide;
(2R)—N-(2-hydroxyethyl)-2-[(4-{[1-(1,3-thiazol-4-ylmethyl)-1H-indazol-5-yl]amino}quinazolin-5-yl)oxy]propanamide;
5-[(1R)-1-methyl-2-morpholin-4-yl-2-oxoethoxy]-N-[1-(1,3-thiazol-4-ylmethyl)-1H-indazol-5-yl]quinazolin-4-amine;
(2S)—N,N-dimethyl-2-[(4-{[1-(1,3-thiazol-4-ylmethyl)-1H-indazol-5-yl]amino}quinazolin-5-yl)oxy]propanamide;
(2S)—N-methyl-2-[(4-{[1-(1,3-thiazol-4-ylmethyl)-1H-indazol-5-yl]amino}quinazolin-5-yl)oxy]propanamide;
5-[(1S)-1-methyl-2-oxo-2-pyrrolidin-1-ylethoxy]-N-[1-(1,3-thiazol-4-ylmethyl)-1H-indazol-5-yl]quinazolin-4-amine;
5-[(1S)-1-methyl-2-morpholin-4-yl-2-oxoethoxy]-N-[1-(1,3-thiazol-4-ylmethyl)-1H-indazol-5-yl]quinazolin-4-amine;
(2S)—N-methyl-2-[(4-{[1-(pyridin-2-ylmethyl)-1H-indazol-5-yl]amino}quinazolin-5-yl)oxy]propanamide;
5-[(1S)-1-methyl-2-morpholin-4-yl-2-oxoethoxy]-N-[1-(pyridin-2-ylmethyl)-1H-indazol-5-yl]quinazolin-4-amine;
(2R)-2-[(4-{[1-(3-fluorobenzyl)-1H-indazol-5-yl]amino}quinazolin-5-yl)oxy]-N-methylpropanamide;
(2R)-2-[(4-{[1-(3-fluorobenzyl)-1H-indazol-5-yl]amino}quinazolin-5-yl)oxy]-N-ethylpropanamide;
(2R)-2-[(4-{[1-(3-fluorobenzyl)-1H-indazol-5-yl]amino}quinazolin-5-yl)oxy]-N-(2-hydroxyethyl)propanamide;
(2R)-2-[(4-{[1-(3-fluorobenzyl)-1H-indazol-5-yl]amino}quinazolin-5-yl)oxy]-N-(2-hydroxyethyl)-N-methylpropanamide;
N-[1-(3-fluorobenzyl)-1H-indazol-5-yl]-5-[(1R)-1-methyl-2-morpholin-4-yl-2-oxoethoxy]quinazolin-4-amine;
(2S)-2-[(4-{[1-(3-fluorobenzyl)-1H-indazol-5-yl]amino}quinazolin-5-yl)oxy]-N-methylpropanamide;
N-[1-(3-fluorobenzyl)-1H-indazol-5-yl]-5-[(1S)-1-methyl-2-morpholin-4-yl-2-oxoethoxy]quinazolin-4-amine;
(2R)—N-(2-hydroxyethyl)-2-[(4-{[1-(1,3-thiazol-2-ylmethyl)-1H-indazol-5-yl]amino}quinazolin-5-yl)oxy]propanamide;
(2R)—N-(2-hydroxyethyl)-N-methyl-2-[(4-{[1-(1,3-thiazol-2-ylmethyl)-1H-indazol-5-yl]amino}quinazolin-5-yl)oxy]propanamide;
(2R)—N-ethyl-2-[(4-{[1-(1,3-thiazol-2-ylmethyl)-1H-indazol-5-yl]amino}quinazolin-5-yl)oxy]propanamide;
(2R)—N-methyl-2-[(4-{[1-(1,3-thiazol-2-ylmethyl)-1H-indazol-5-yl]amino}quinazolin-5-yl)oxy]propanamide;
5-[(1R)-1-methyl-2-morpholin-4-yl-2-oxoethoxy]-N-[1-(1,3-thiazol-2-ylmethyl)-1H-indazol-5-yl]quinazolin-4-amine;
(2S)—N-methyl-2-[(4-{[1-(1,3-thiazol-2-ylmethyl)-1H-indazol-5-yl]amino}quinazolin-5-yl)oxy]propanamide; and
5-[(1S)-1-methyl-2-morpholin-4-yl-2-oxoethoxy]-N-[1-(1,3-thiazol-2-ylmethyl)-1H-indazol-5-yl]quinazolin-4-amine;

or a pharmaceutically acceptable salt thereof.

A quinazoline derivative of the Formula I, or a pharmaceutically acceptable salt thereof, may be prepared by any process known to be applicable to the preparation of chemically-related compounds. Suitable processes include, for example, those illustrated in WO 96/15118, WO 01/94341, WO 03/040108 and WO 03/040109. Such processes, when used to prepare a quinazoline derivative of the Formula I are provided as a further feature of the invention and are illustrated by the following representative process variants in which, unless otherwise stated, $R^1$, $R^2$, $R^3$, $R^4$, $R^5$, $X^1$, $Q^1$, $G^1$, $G^2$, $G^3$ and $G^4$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated, which are within the ordinary skill of an organic chemist.

Process (a) The reaction of a quinazoline of the Formula II:

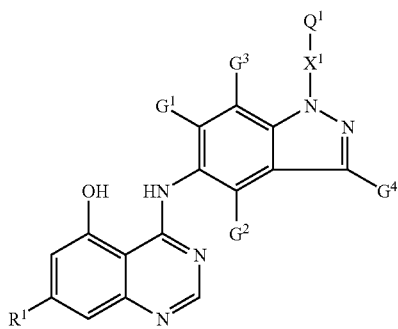

wherein $R^1$, $G^1$, $G^2$, $G^3$, $G^4$, $X^1$ and $Q^1$ have any of the meanings defined hereinbefore except that any functional group is protected if necessary, with an amide of the Formula III:

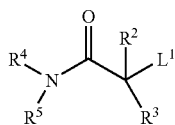

wherein $R^2$, $R^3$, $R^4$ and $R^5$ have any of the meanings defined hereinbefore except that any functional group is protected if necessary and $L^1$ is a suitable displaceable group, such as halogeno (for example chloro or bromo), a sulfonyloxy group (for example a methylsulfonyloxy or a toluene-4-sulfonyloxy group) or $L^1$ is a hydroxy group;

or

Process (b) The coupling, conveniently in the presence of a suitable base, of a quinazoline of the Formula IV (or a suitable salt thereof, for example an alkali earth metal salt or an alkali metal salt, such as a sodium or a potassium salt, thereof):

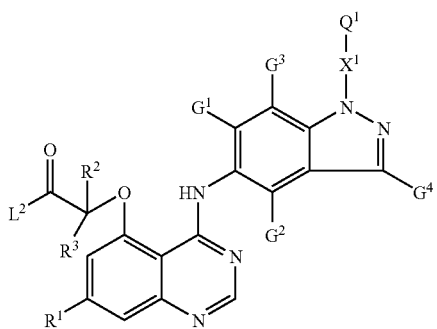

wherein $R^1$, $R^2$, $R^3$, $G^1$, $G^2$, $G^3$, $G^4$, $X^1$ and $Q^1$ have any of the meanings defined hereinbefore except that any functional group is protected if necessary, and $L^2$ is a suitable displaceable group, for example (1-3C)alkoxy (such as methoxy or ethoxy) or $L^2$ is hydroxy, which hydroxy group is conveniently combined with a suitable coupling agent to produce a displaceable group, with an amine of the Formula V:

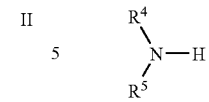

wherein $R^4$ and $R^5$ have any of the meanings defined hereinbefore except that any functional group is protected if necessary;

or

Process (c) For quinazoline derivatives of the Formula I wherein $R^2$ is 2-hydroxyethyl, the reaction of a quinazoline of the Formula VI:

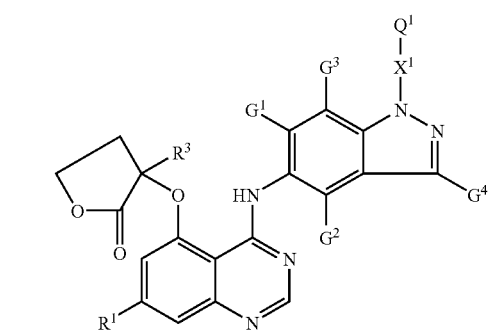

wherein $R^1$, $R^3$, $G^1$, $G^2$, $G^3$, $G^4$, $X^1$ and $Q^1$ have any of the meanings defined hereinbefore except that any functional group is protected if necessary, with an amine of the Formula V as defined above;

or

Process (d) The reaction of a quinazoline of the Formula VII:

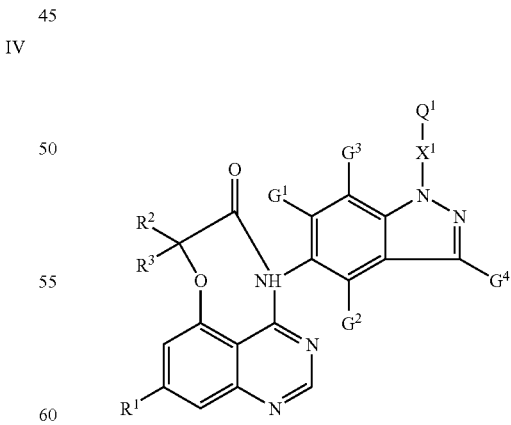

wherein $R^1$, $R^2$, $R^3$, $G^1$, $G^2$, $G^3$, $G^4$, $X^1$ and $Q^1$ have any of the meanings defined hereinbefore except that any functional group is protected if necessary, with an amine of the Formula V as defined above;

or

Process (e) The reaction of a quinazolin-4(3H)-one of the Formula VIII:

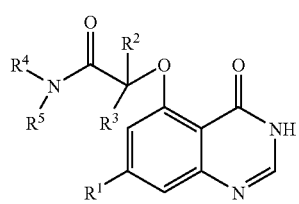

VIII wherein $R^1$, $R^2$, $R^3$, $R^4$ and $R^5$ have any of the meanings defined hereinbefore except that any functional group is protected if necessary, with a suitable activating group and an amine of the Formula IX:

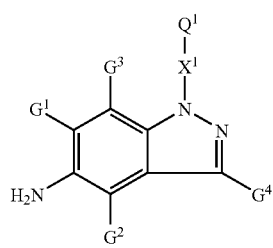

IX wherein $G^1$, $G^2$, $G^3$, $G^4$, $X^1$ and $Q^1$ have any of the meanings defined hereinbefore except that any functional group is protected if necessary;

or

Process (f) The reaction of a quinazoline of the Formula X:

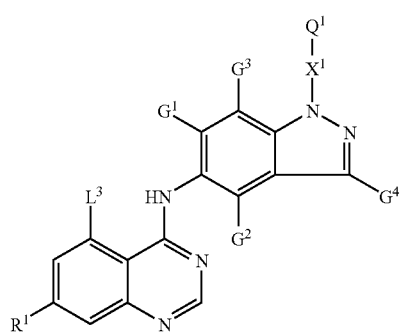

X wherein $R^1$, $G^1$, $G^2$, $G^3$, $G^4$, $X^1$ and $Q^1$ have any of the meanings defined hereinbefore except that any functional group is protected if necessary and $L^3$ is a suitable displaceable group such as halogeno (for example fluoro) with a compound of the Formula XI:

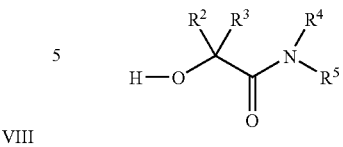

XI wherein $R^2$, $R^3$, $R^4$ and $R^5$ have any of the meanings defined hereinbefore except that any functional group is protected if necessary;

or

Process (g) The coupling, conveniently in the presence of a suitable base, of a quinazoline of the Formula XII:

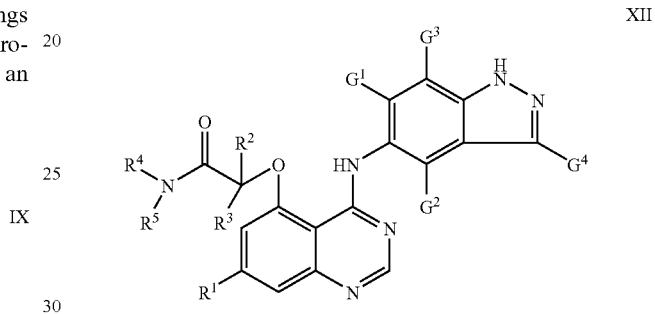

XII wherein $R^1$, $R^2$, $R^3$, $R^4$, $R^5$, $G^1$, $G^2$, $G^3$ and $G^4$ have any of the meanings defined hereinbefore except that any functional group is protected if necessary, with a compound of the Formula XIII:

$$Q^1\text{-}X^1\text{-}L^4 \qquad \text{XIII}$$

wherein $Q^1$ and $X^1$ have any of the meanings defined hereinbefore except that any functional group is protected if necessary and $L^4$ is a suitable displaceable group, such as halogeno (for example fluoro, chloro, bromo or iodo) or a sulfonyloxy group (for example a methylsulfonyloxy or toluene-4-sulfonyloxy group);

or

Process (h) For quinazoline derivatives of the Formula I wherein $R^1$ is hydrogen, the hydrogenation of a quinazoline of the Formula XIV:

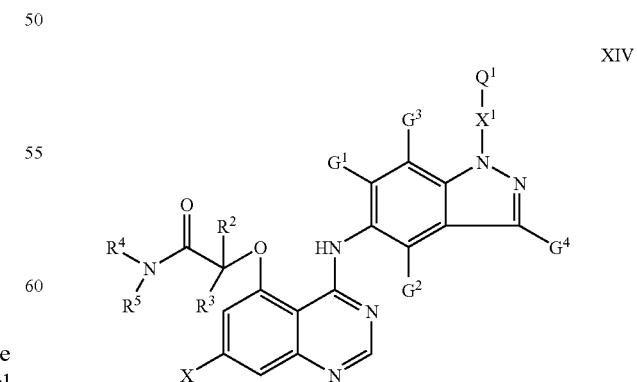

XIV wherein X is halogeno (such as iodo, bromo or chloro) and $R^2$, $R^3$, $R^4$, $R^5$, $G^1$, $G^2$, $G^3$, $G^4$, $X^1$ and $Q^1$ have any of the meanings defined hereinbefore except that any functional group is protected if necessary;

and thereafter, if necessary:

(i) converting a quinazoline derivative of the Formula I into another quinazoline derivative of the Formula I;

(ii) removing any protecting group that is present (by conventional means);

(iii) forming a pharmaceutically acceptable salt.

Specific conditions for the above reactions are as follows:

Process (a)

When $L^1$ is, for example, halogeno or a sulfonyloxy group, the reaction of process (a) is conveniently carried out in the presence of a suitable base. A suitable base is, for example, an alkali or alkaline earth metal carbonate, such as sodium carbonate, potassium carbonate, caesium carbonate or calcium carbonate. The reaction is, optionally, carried out in the presence of a source of iodide such as sodium iodide or potassium iodide or in the presence of a suitable alkali metal hydride such as sodium hydride or potassium hydride.

The reaction is conveniently carried out in the presence of a suitable inert solvent or diluent, for example an ester such as ethyl acetate, a halogenated solvent such as methylene chloride, chloroform or carbon tetrachloride, an ether such as tetrahydrofuran or 1,4-dioxan, an aromatic solvent such as toluene, an alcohol such as methanol or ethanol, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, from 0 to 120° C., conveniently at or near ambient temperature and/or at about 50° C.

When $L^1$ is hydroxy, the reaction of process (a) is conveniently carried out under suitable Mitsunobu conditions. Suitable Mitsunobu conditions include, for example, reaction in the presence of a suitable tertiary phosphine and a di-alkylazodicarboxylate in an organic solvent such as THF, or suitably dichloromethane and in the temperature range 0° C. to 60° C., but conveniently at ambient temperature. A suitable tertiary phosphine includes for example tri-n-butylphosphine or suitably tri-phenylphosphine. A suitable di-alkylazodicarboxylate includes for example diethyl azodicarboxylate (DEAD) or suitably di-tert-butyl azodicarboxylate (DTAD). Details of Mitsunobu reactions are contained in Tet. Letts., 31, 699, (1990); The Mitsunobu Reaction, D. L. Hughes, Organic Reactions, 1992, Vol. 42, 335-656 and Progress in the Mitsunobu Reaction, D. L. Hughes, Organic Preparations and Procedures International, 1996, Vol. 28, 127-164.

Process (b)

When $L^2$ is hydroxy, the reaction of process (b) is conveniently carried out in the presence of a suitable coupling agent and, optionally, in the presence of a suitable catalyst and/or a suitable base. A suitable coupling agent is, for example, a suitable peptide coupling agent, such as O-(7-azabenzotriazol-1-yl)-N,N,N',N'-tetramethyluronium hexafluoro-phosphate (HATU) or a carbodiimide such as dicyclohexylcarbodiimide or 1-(3-dimethylaminopropyl)-3-ethylcarbodiimide hydrochloride (EDCI). A suitable catalyst is, for example, dimethylaminopyridine, 4-pyrrolidinopyridine, 2-hydroxypyridine N-oxide (HOPO) or 1-hydroxybenzotriazole (HOBT). A suitable base is, for example, an organic amine base such as pyridine, 2,6-lutidine, collidine, 4-dimethylaminopyridine, triethylamine, di-isopropylethylanine, N-methylmorpholine or diazabicyclo[5.4.0]undec-7-ene, or an alkali or alkaline earth metal carbonate, such as sodium carbonate, potassium carbonate, caesium carbonate or calcium carbonate.

When $L^2$ is (1-3C)alkoxy, no base, coupling agent or catalyst is required.

The reaction of process (b) is conveniently carried out in the presence of a suitable inert solvent or diluent, for example an ether such as tetrahydrofuran or 1,4-dioxan, an aromatic solvent such as toluene, an alcohol such as methanol or ethanol, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, from 0 to 120° C. When $L^2$ is hydroxy, the reaction may conveniently be carried out at or near ambient temperature.

Conveniently, this reaction may also be performed by heating the reactants in a sealed vessel using a suitable heating apparatus such as a microwave heater.

Process (c)

The reaction of process (c) is conveniently carried out in the presence of a suitable inert solvent or diluent, for example an ester such as ethyl acetate, a halogenated solvent such as methylene chloride, chloroform or carbon tetrachloride, an ether such as tetrahydrofuran or 1,4-dioxan, an aromatic solvent such as toluene, an alcohol such as ethanol, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, from 0 to 120° C., conveniently at or near ambient temperature.

Process (d)

The reaction of process (d) is conveniently carried out in the presence of a suitable inert solvent or diluent, for example an ester such as ethyl acetate, a halogenated solvent such as methylene chloride, chloroform or carbon tetrachloride, an ether such as tetrahydrofuran or 1,4-dioxan, an aromatic solvent such as toluene, an alcohol such as methanol or ethanol, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, from 0 to 120° C., conveniently at or near ambient temperature.

Process (e)

In process (e), the quinazolin-4(3H)-one of the Formula VIII is conveniently reacted with a suitable activating agent, so as to replace the oxo group at the 4-position on the quinazolin-4(3H)-one ring by a suitable displaceable group, for example halogeno (for such as chloro) and to form a quinazoline (hereinafter referred to as the "activated quinazoline") for reaction with the amine of the Formula IX. The activated quinazoline so formed may conveniently be used in situ without further purification.

The reaction of the quinazolin-4(3H)-one of the Formula VIII with a suitable activating agent is conveniently carried out using conventional methods. For example, the quinazolin-4(3H)-one of the Formula VIII may be reacted with a suitable halogenating agent such as thionyl chloride, phosphoryl chloride or a mixture of carbon tetrachloride and triphenylphosphine.

The reaction of the activated quinazoline with the amine of the Formula IX is conveniently carried out in the presence of an acid, for example in the presence of a catalytic amount of an acid. Suitable acids include, for example hydrogen chloride gas (conveniently dissolved in a suitable inert solvent such as diethyl ether or dioxane) or hydrochloric acid.

Alternatively, when the activated quinazoline contains a halogeno group (for example chloro) at the 4-position on the quinazoline ring, the reaction with the amine of the Formula IX may be carried out in the absence of an acid or a base. In this reaction displacement of the halogeno leaving group results in the formation of the acid (H-halogeno) in-situ and the autocatalysis of the reaction.

Alternatively, the reaction of the activated quinazoline with the amine of the Formula IX may be carried out in the presence of a suitable base. A suitable base is, for example, lithium hexamethyldisilazide (LiHMDS) or sodium hexamethyldisilazide (NaHMDS).

The above reactions are conveniently carried out in the presence of a suitable inert solvent or diluent, for example an alcohol or ester such as methanol, ethanol, isopropanol or ethyl acetate, a halogenated solvent such as dichloroethane, methylene chloride, chloroform or carbon tetrachloride, an ether such as tetrahydrofuran, diethyl ether or 1,4-dioxan, an aromatic solvent such as toluene, or a dipolar aprotic solvent such as N,N-dimethylformamide, N,N-dimethylacetamide, N-methylpyrrolidin-2-one or dimethylsulfoxide.

When conducted in the presence or absence of an acid, the above reactions are conveniently carried out at a temperature in the range, for example, 0 to 250° C., conveniently in the range 40 to 80° C. or, preferably, at or near the reflux temperature of the solvent when used. When conducted in the presence of a base, the above reactions are conveniently carried out at a temperature in the range, for example, −78 to 30° C.

Process (f)

Process (f) may conveniently be carried out in the presence of a suitable base. A suitable base is, for example, an alkali metal hydride, such as sodium hydride.

The reaction is conveniently carried out in the presence of a suitable inert solvent or diluent, for example an ether such as tetrahydrofuran or 1,4-dioxan, an aromatic solvent such as toluene, or a dipolar aprotic solvent such as N N-dimethylformamide, N,N-dimethylacetamide, N-methylpyrrolidin-2-one or dimethylsulfoxide. The reaction is conveniently carried out at a temperature in the range, for example, from 0 to 120° C.

Process (g)

A particular displaceable group $L^4$ is bromo, chloro or methylsulfonyloxy.

The reaction of a quinazoline of the Formula XII with a compound of the Formula XIII is conveniently carried out in the presence of a suitable base. A suitable base is, for example, an organic amine base such as pyridine, 2,6-lutidine, collidine, 4-dimethylaminopyridine, triethylamine, di-isopropylethylamine, N-methylmorpholine or diazabicyclo [5.4.0]undec-7-ene, or, for example, an alkali or alkaline earth metal carbonate, such as sodium carbonate, potassium carbonate, cesium carbonate, calcium carbonate, or, for example, an alkali metal hydride, such as sodium hydride.

The reaction of a quinazoline of the Formula XII with a compound of the Formula XIII is conveniently carried out in the presence of a suitable inert solvent or diluent, for example a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one or dimethylsulfoxide. Alternatively, the reaction may be conducted in the absence of an inert solvent or diluent. The reaction is conveniently carried out at a temperature in the range of, for example, from 25 to 100° C., conveniently at or near ambient temperature.

Process (h)

As the skilled person would appreciate, the hydrogenation in process (h) may be conducted using conventional methods. For example, suitable methods include catalytic hydrogenation over a suitable catalyst (such as a platinum or palladium catalyst).

Starting Materials

Starting Materials for Process (a)

The quinazoline of the Formula II may be obtained by conventional procedures, for example as illustrated in Reaction Scheme 1:

Reaction Scheme 1

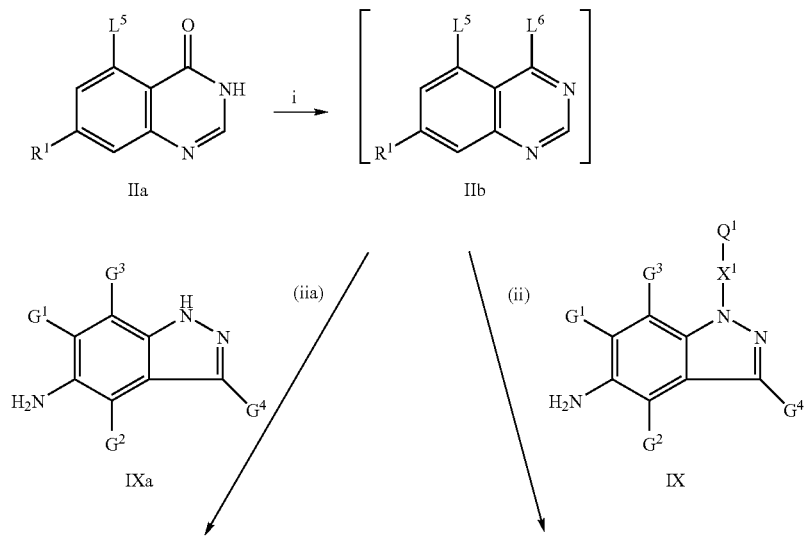

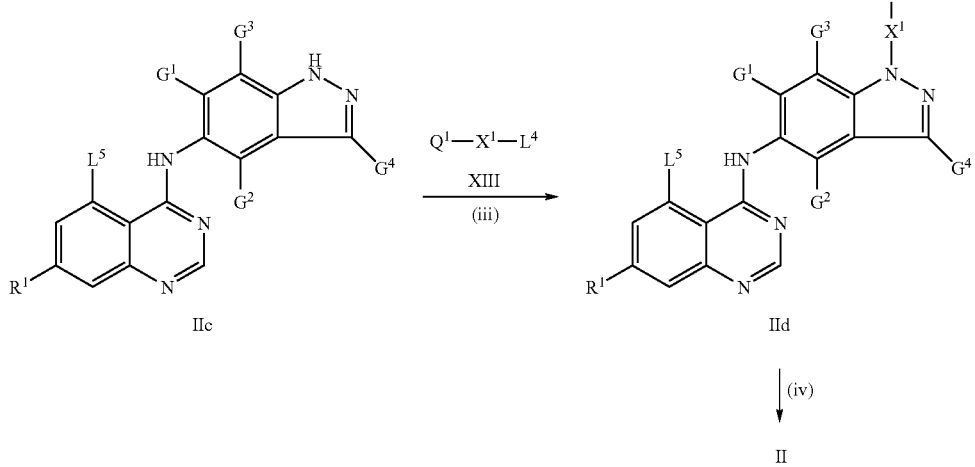

wherein $L^4$, $L^5$ and $L^6$ are suitable displaceable groups, provided that $L^1$ is more labile than $L^5$, and $R^1$, $G^1$, $G^2$, $G^3$, $G^4$, $X^1$ and $Q^1$ have any of the meanings defined hereinbefore except that any functional group is protected if necessary.

A suitable displaceable group $L^4$ is as defined above. A suitable displaceable group $L^5$ is, for example, halogeno or a sulfonyloxy group, such as fluoro, chloro, methylsulfonyloxy or toluene-4-sulfonyloxy, particularly fluoro. A suitable displaceable group $L^6$ is, for example, halogeno or an alkoxy, aryloxy, mercapto, alkylthio, arylthio, alkylsulfinyl, arylsulfinyl, alkylsulfonyl, arylsulfonyl, alkylsulfonyloxy or arylsulfonyloxy group, for example a chloro, bromo, methoxy, phenoxy, pentafluorophenoxy, methylthio, methanesulfonyl, methanesulfonyloxy or toluene-4-sulfonyloxy group. Preferably $L^5$ and $L^6$ are both halogeno, for example $L^5$ is fluoro and $L^6$ is chloro.

Notes for Reaction Scheme 1:

Step (i)

As the skilled person would appreciate, the conversion of a quinazolone of the Formula IIa to a quinazoline of the Formula IIb may be conducted using conventional methods, for example by reacting the compound of the Formula IIa with a suitable activating agent. For example, when $L^5$ is fluoro and $L^6$ is halogeno (for example chloro), 5-fluoro-quinazolin-4(3H)-one may be reacted with a suitable halogenating agent such as thionyl chloride, phosphoryl chloride or a mixture of carbon tetrachloride and triphenylphosphine.

Steps (ii) and (iia)

The reaction of the quinazoline of the Formula IIb with the amine of the Formula IX or IXa is conveniently carried out in the presence of an acid, for example in the presence of a catalytic amount of an acid. Suitable acids include, for example hydrogen chloride gas (conveniently dissolved in a suitable inert solvent such as diethyl ether or dioxane) or hydrochloric acid.

Alternatively, the reaction may be carried out in the presence of a suitable base. A suitable base is, for example, lithium hexamethyldisilazide (LiHMDS) or sodium hexamethyldisilazide (NaHMDS).

Alternatively, the reaction may be carried out in the absence of an acid or a base. In this reaction displacement of the halogeno leaving group results in the formation of the acid (H-halogeno) in-situ and the autocatalysis of the reaction.

The above reactions are conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran, diethyl ether or 1,4-dioxan, an aromatic solvent such as toluene, or a dipolar aprotic solvent such as N,N-dimethylformamide, N,N-dimethylacetamide, N-methylpyrrolidin-2-one or dimethylsulfoxide.

When conducted in the presence or absence of an acid, the above reactions are conveniently carried out at a temperature in the range, for example, 0 to 250° C., conveniently in the range 40 to 80° C. or, preferably, at or near the reflux temperature of the solvent when used. When conducted in the presence of a base, the above reactions are conveniently carried out at a temperature in the range, for example, −78 to 30° C.

Step (iii)

The reaction of step (iii) may conveniently be carried out using analogous conditions to those used in process (g) as discussed above.

Step (iv)

The conversion of a quinazoline of the Formula IId to a quinazoline of the Formula II may be carried out by reaction with a suitably protected oxygen nucleophile, followed by removal of the protecting group by conventional means. For example, the conversion may conveniently be carried out by reaction with N-acetylethanolamine in the presence of a suitable base. A suitable base is, for example, a strong non-nucleophilic base such as an alkali metal hydride (for example sodium hydride) or an alkali metal amide (for example lithium di-isopropylamide (LDA)). The reaction is conveniently carried out in the presence of a suitable inert solvent or diluent, for example an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, from 10 to 250° C., preferably in the range from 100 to 150° C.

The conversion may alternatively be carried out by reaction with a suitable alkali metal alkoxide (for example sodium methoxide), followed by a conventional demethylation reaction. For example, the reaction with a suitable alkali metal alkoxide, such as sodium methoxide, may be carried out in the presence of a suitable inert solvent such as methanol at or near the reflux temperature of the solvent. Any suitable demethylation reaction conditions may be used. For example, the demethylation step may be carried out by reaction with pyridinium hydrochloride at a temperature in the range from 50 to 180° C., by reaction with boron tribromide at a temperature in the range from −78 to 30° C. or by reaction with a suitable thiolate, such as sodium thiophenolate at a temperature in the range from 50 to 200° C. In particular, the demethylation reaction may be carried out by reaction with pyridinium hydrochloride in the presence of a pyridine solvent at or near the reflux temperature of the solvent.

Starting Materials for Reaction Scheme 1

The compounds of the Formula IIa are commercially available or may be prepared using conventional methods. For example, the 5-fluoro-quinazolin-4(3H)-one starting material is commercially available or can be prepared using conventional methods, for example as described in J. Org. Chem. 1952, 17, 164-176.

Compounds of the Formulae IX and IXa are commercially available compounds or they are known in the literature, or they can be prepared by standard processes known in the art. For example, compounds of the Formulae IX and IXa may be prepared in accordance with Reaction Scheme 2:

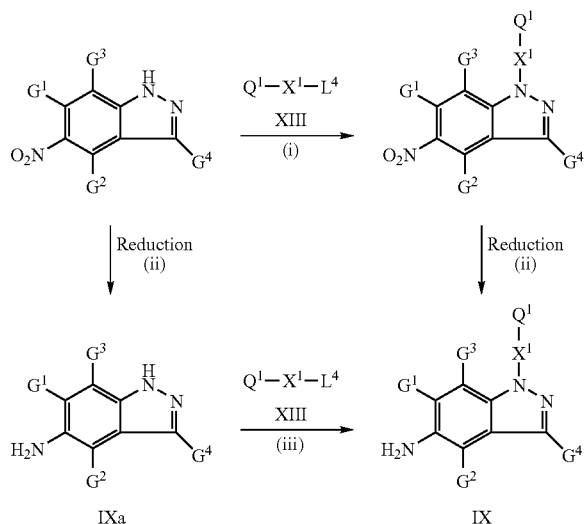

wherein $L^4$ is a suitable displaceable group as defined above and $G^1$, $G^2$, $G^3$, $G^4$, $X^1$ and $Q^1$ have any of the meanings defined hereinbefore except that any functional group is protected if necessary.

Notes for Reaction Scheme 2:

Step (i)

The reaction of step (i) may conveniently be carried out using analogous conditions to those used in process (g) as discussed above.

Step (ii)

As the skilled person would appreciate, the reduction in step (ii) of Reaction Scheme 2 may be conducted using conventional methods. For example, the reduction of the nitro group in step (ii) may be carried out under standard conditions, for example by catalytic hydrogenation over a platinum/carbon, palladium/carbon or nickel catalyst, treatment with a metal such as iron, titanium (III) chloride, tin (II) chloride or indium, or treatment with another suitable reducing agent such as sodium dithionite or a platinum (IV) oxide.

Step (iii)

The reaction of step (iii) may conveniently be carried out using analogous is conditions to those used in process (g) as discussed above, but the amino (—NH$_2$) group typically must be protected during this reaction.

The amides of the Formula III are commercially available, or they are known in the literature, or can be prepared using well-known processes in the art.

Starting Materials for Process (b)

The quinazoline of the Formula IV may be obtained by conventional procedures. For example quinazoline compounds of the Formula IV wherein $L^2$ is (1-3C)alkoxy (such as methoxy) may be prepared by reaction of a compound of the Formula II as defined above or a compound of the Formula IId as defined above with a compound of the Formula IVa:

wherein $R^8$ is a (1-3C)alkyl group and $R^2$ and $R^3$ have any of the meanings defined hereinbefore except that any functional group is protected if necessary.

The reaction of a compound of the Formula II with a compound of the Formula IVa may conveniently be carried out under suitable Mitsunobu conditions as described above.

The reaction of a compound of the Formula IId with a compound of the Formula IVa is conveniently carried out in the presence of a suitable base. A suitable base is, for example, an alkali metal alkoxide, such as sodium methoxide or sodium ethoxide.

Quinazoline compounds of the Formula IV wherein $L^2$ is hydroxy (or a suitable salt thereof) may be prepared by reaction of a compound of the Formula IV wherein $L^2$ is (1-3C) alkoxy with a suitable alkali metal hydroxide, for example sodium hydroxide at room temperature. This reaction is conveniently carried out in the presence of a suitable inert solvent or diluent, for example an ether such as tetrahydrofuran or 1,4-dioxane or an alcohol such as methanol.

Quinazoline compounds of the Formula IV wherein $L^2$ is hydroxy (or a suitable salt thereof) may alternatively be prepared by reaction of a compound of the Formula II with a suitable halogenated (for example chlorinated) alcohol under suitable chlorotone reaction conditions, as appreciated by a person skilled in the art and, for example, described in Reference Example 27 of WO 03/077847.

The compounds of the Formulae IVa and V are commercially available, or they are known in the literature, or can be prepared using well-known processes in the art.

Starting Materials for Process (c)

The compounds of the Formula VI can be prepared using well-known processes in the art. For example, the compounds of the Formula VI can be prepared by reaction of a compound of the Formula II as defined above with a compound of the Formula VIa:

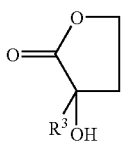

VIa wherein R³ has any of the meanings defined hereinbefore except that any functional group is protected if necessary, for example under suitable Mitsunobu conditions, as discussed above.

The compounds of the Formula V and VIa are commercially available, or they are known in the literature, or can be prepared using well-known processes in the art.

Starting Materials for Process (d)

The compounds of the Formula V are discussed above.

The compounds of the Formula VII may be prepared from compounds of the Formula IV wherein L² is hydroxy by an internal coupling reaction using a suitable coupling agent and a suitable base as described above (for example HATU and di-isopropylethylamine) under the reaction conditions discussed above for process (b).

Starting Materials for Process (e)

The compounds of the Formula VIII may be prepared using well-known processes in the art. Compounds of the Formula VIII may, for example, be prepared by reaction of an appropriate quinazolin-4(3H)-one compound of the Formula VIIIa:

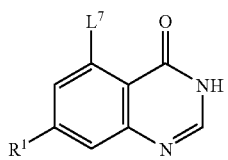

VIIIa wherein L⁷ is a suitable displaceable group such as halogeno or a sulfonyloxy group (for example fluoro, chloro, methylsulfonyloxy or toluene-4-sulfonyloxy group, particularly fluoro) or L⁷ is hydroxy, and R¹ has any of the meanings defined hereinbefore except that any functional group is protected if necessary, with a compound of the Formula III as defined above. Typically, the nitrogen at the 3-position on the quinazoline ring is protected, for example by a pyvaloyloxymethyl group.

When L⁷ is a suitable displaceable group, the reaction of a compound of the Formula VIIIa with a compound of the Formula III is conveniently carried out using analogous conditions to those used in step (iv) of Reaction Scheme 1 as described above and in process (a) above.

When L⁷ is hydroxy, the reaction of a compound of the Formula VIIIa with a compound of the Formula III is conveniently carried out under the conditions described above for process (a).

The compounds of the Formula VIIIa are commercially available, or they are known in the literature, or they can be prepared using well-known processes in the art (for example, when R¹ is hydrogen and L⁷ is fluoro, the compound 5-fluoro-3,4-dihydroquinazoline starting material is commercially available or can be prepared using conventional methods, for example as described in J. Org. Chem. 1952, 17, 164-176).

The compounds of the Formula IX are commercially available, or they are known in the literature, or can be prepared using well-known processes in the art (for example as described in Reaction Scheme 2 above).

Starting Materials for Process (f)

Quinazolines of the Formula X may be prepared using processes as discussed above, for example as discussed in Reaction Scheme 1.

The compounds of the Formula XI are commercially available, or they are known in the literature, or can be prepared using well-known processes in the art.

Starting Materials for Process (g)

Quinazolines of the Formula XII may be prepared using processes as discussed above, for example as discussed in Reaction Scheme 1.

Compounds of the Formula XIII are commercially available compounds or they are known in the literature, or they can be can be prepared by standard processes known in the art.

Starting Materials for Process (h)

Quinazolines of the Formula XIV may be prepared using processes as discussed above.

The quinazoline derivative of the Formula I may be obtained from the above processes in the form of the free base or alternatively it may be obtained in the form of a salt, for example an acid addition salt. When it is desired to obtain the free base from a salt of the quinazoline derivative of the Formula I, the salt may be treated with a suitable base, for example, an alkali or alkaline earth metal carbonate or hydroxide, for example sodium carbonate, potassium carbonate, calcium carbonate, sodium hydroxide or potassium hydroxide, or by treatment with ammonia for example using a methanolic ammonia solution such as 7N ammonia in methanol.

The conversion of a quinazoline derivative of the Formula I into another quinazoline derivative of the Formula I may be conducted using any suitable process, as the skilled person would appreciate. For example, a quinazoline derivative of the Formula I wherein R¹ is hydroxy may be converted into another quinazoline derivative of the Formula I wherein R¹ is (1-4C)alkoxy by means of a Mitsunobu reaction, details of which are discussed above.

The protecting groups used in the processes above may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1 to 4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1 to 20 carbon atoms). Examples of carboxy protecting groups include straight or branched chain (1 to 12C)alkyl groups (for example isopropyl and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); lower alkanoyloxyalkyl groups (for example pivaloyloxymethyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl. For example a tert butoxycarbonyl protecting group may be removed from an amino group by an acid catalysed hydrolysis using trifluoroacetic acid.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

It will be appreciated that certain of the various ring substituents in the quinazoline derivatives of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group.

When a pharmaceutically acceptable salt of a quinazoline derivative of the Formula I is required, for example an acid-addition salt, it may be obtained by, for example, reaction of said quinazoline derivative with a suitable acid using a conventional procedure.

As mentioned hereinbefore some of the compounds according to the present invention may contain one or more chiral centers and may therefore exist as stereoisomers. Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. When a specific stereoisomer is isolated it is suitably isolated substantially free for other stereoisomers, for example containing less than 20%, particularly less than 10% and more particularly less than 5% by weight of other stereoisomers.

In the section above relating to the preparation of the quinazoline derivative of the Formula I, the expression "inert solvent" refers to a solvent which does not react with the starting materials, reagents, intermediates or products in a manner which adversely affects the yield of the desired product.

Persons skilled in the art will appreciate that, in order to obtain quinazoline derivatives of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

Certain intermediates used in the processes described above are novel and form a further feature of the present invention. Accordingly there is provided a compound selected from a compound the Formulae II, IV, VI, VII, VIII, X, XII and XIV as hereinbefore defined, or a salt thereof.

Particular compounds of the Formula IV include one or more quinazoline derivatives selected from methyl (2R)-2-[(4-{[1-(pyridin-2-ylmethyl)-1H-indazol-5-yl]amino}quinazolin-5-yl)oxy]propanoate, (2R)-2-[(4-{[1-(pyridin-2-ylmethyl)-1H-indazol-5-yl]amino}quinazolin-5-yl)oxy]propanoic acid and methyl [(4-{[1-(pyridin-2-ylmethyl)-1H-indazol-5-yl]amino}quinazolin-5-yl)oxy]acetate.

Further particular compounds of Formula IV include one or more quinazoline derivatives selected from methyl (2S)-2-[(4-{[1-(3-fluorobenzyl)-1H-indazol-5-yl]amino}quinazolin-5-yl)oxy]propanoate, methyl (2R)-2-[(4-{[1-(3-fluorobenzyl)-1H-indazol-5-yl]amino}quinazolin-5-yl)oxy]propanoate, methyl (2S)-2-[(4-{[1-(pyridin-2-ylmethyl)-1H-indazol-5-yl]amino}quinazolin-5-yl)oxy]propanoate, methyl (2S)-2-[(4-{[1-(1,3-thiazol-2-ylmethyl)-1H-indazol-5-yl]amino}quinazolin-5-yl)oxy]propanoate and methyl (2R)-2-[(4-{[1-(1,3-thiazol-2-ylmethyl)-1H-indazol-5-yl]amino}quinazolin-5-yl)oxy]propanoate.

Still further particular compounds of Formula IV include one or more quinazoline derivatives selected from methyl (2R)-2-[(4-{[1-(1,3-thiazol-4-ylmethyl)-1H-indazol-5-yl]amino}quinazolin-5-yl)oxy]propanoate, (2R)-2-[(4-{[1-(1,3-thiazol-4-ylmethyl)-1H-indazol-5-yl]amino}quinazolin-5-yl)oxy]propanoic acid, methyl (2S)-2-[(4-{[1-(1,3-thiazol-4-ylmethyl)-1H-indazol-5-yl]amino}quinazolin-5-yl)oxy]propanoate, (2S)-2-[(4-{[1-(1,3-thiazol-4-ylmethyl)-1H-indazol-5-yl]amino}quinazolin-5-yl)oxy]propanoic acid, (2S)-2-[(4-{[1-(pyridin-2-ylmethyl)-1H-indazol-5-yl]amino}quinazolin-5-yl)oxy]propanoic acid, (2R)-2-[(4-{[1-(3-fluorobenzyl)-1H-indazol-5-yl]amino}quinazolin-5-yl)oxy]propanoic acid, (2S)-2-[(4-{[1-(3-fluorobenzyl)-1H-indazol-5-yl]amino}quinazolin-5-yl)oxy]propanoic acid, (2R)-2-[(4-{[1-(1,3-thiazol-2-ylmethyl)-1H-indazol-5-yl]amino}quinazolin-5-yl)oxy]propanoic acid and (2S)-2-[(4-{[1-(1,3-thiazol-2-ylmethyl)-1H-indazol-5-yl]amino}quinazolin-5-yl)oxy]propanoic acid.

A particular compound of the Formula VII is (6R)-6-methyl-4-[1-(pyridin-2-ylmethyl)-1H-indazol-5-yl]-4H-[1,4]oxazepino[5,6,7-de]quinazolin-5(6H)-one.

Particular compounds of the Formula VIII include one or more quinazoline derivatives selected from (2R)—N,N-dimethyl-2-[(4-oxo-3,4-dihydroquinazolin-5-yl)oxy]propanamide and (2S)—N,N-dimethyl-2-[(4-oxo-3,4-dihydroquinazolin-5-yl)oxy]propanamide.

Particular compounds of the Formula II include one or more of the quinazoline derivatives selected from 4-{[1-(pyridin-2-ylmethyl)-1H-indazol-5-yl]amino}quinazolin-5-ol, 4-{[1-(3-fluorobenzyl)-1H-indazol-5-yl]amino}quinazolin-5-ol and 4-{[1-(1,3-thiazol-2-ylmethyl)-1H-indazol-5-yl]amino}quinazolin-5-ol. A further particular compound of the Formula II includes 4-{[1-(1,3-thiazol-4-ylmethyl)-1H-indazol-5-yl]amino}quinazolin-5-ol.

Particular compounds of the Formula X include one or more of is 5-fluoro-N-[1-(pyridin-2-ylmethyl)-1H-indazol-5-yl]quinazolin-4-amine, 5-fluoro-N-[1-(3-fluorobenzyl)-1H-indazol-5-yl]quinazolin-4-amine and 5-fluoro-N-[1-(1,3-thiazol-2-ylmethyl)-1H-indazol-5-yl]quinazolin-4-amine. A further particular compound of the Formula X includes 5-fluoro-N-[1-(1,3-thiazol-4-ylmethyl)-1H-indazol-5-yl]quinazolin-4-amine.

The intermediate may be in the form of a salt of the intermediate. Such salts need not be a pharmaceutically acceptable salt. For example it may be useful to prepare an intermediate in the form of a pharmaceutically non-acceptable salt if, for example, such salts are useful in the manufacture of a quinazoline derivative of the Formula I.

Biological Assays

The inhibitory activities of compounds were assessed in non-cell based protein tyrosine kinase assays as well as in cell based proliferation assays before their in vivo activity was assessed in Xenograft studies.

a) Protein Tyrosine Kinase Phosphorylation Assays

This test measures the ability of a test compound to inhibit the phosphorylation of a tyrosine containing polypeptide substrate by EGFR, erbB2 and erbB4 tyrosine kinase enzyme.

Recombinant intracellular fragments of EGFR, erbB2 and erbB4 (accession numbers X00588, X03363 and L07868 respectively) were cloned and expressed in the baculovirus/Sf21 system. Lysates were prepared from these cells by treatment with ice-cold lysis buffer (20 mM N-2-hydroxyethylpiperizine-N'-2-ethanesulfonic acid (HEPES) pH7.5, 150 mM NaCl, 10% glycerol, 1% Triton X-100, 1.5 mM MgCl$_2$, 1 mM ethylene glycol-bis(β-aminoethyl ether) N',N',N',N'-tetraacetic acid (EGTA), plus protease inhibitors and then cleared by centrifugation.

Constitutive kinase activity of these recombinant proteins was determined by their ability to phosphorylate a synthetic peptide (made up of a random co-polymer of Glutamic Acid, Alanine and Tyrosine in the ratio of 6:3:1). Specifically, Maxisorb™ 96-well immunoplates were coated with synthetic peptide (0.2 µg of peptide in a 100 µl phosphate buffered saline (PBS) solution and incubated at 4° C. overnight). Plates were washed in 50 mM HEPES pH 7.4 at room temperature to remove any excess unbound synthetic peptide. EGFR or erbB2 activities were assessed by incubation in peptide coated plates for 20 minutes at room temperature in 50 mM HEPES pH 7.4 at room temperature, adenosine trisphosphate (ATP) at Km concentration for the respective enzyme, 10 mM MnCl$_2$, 0.05 mM Na$_3$VO$_4$, 0.1 mM DL-dithiothreitol (DTT), 0.05% Triton X-100 with test compound in DMSO (final concentration of 2.5%). Reactions were terminated by the removal of the liquid components of the assay followed by washing of the plates with PBS-T (phosphate buffered saline with 0.05% Tween 20).

The immobilised phospho-peptide product of the reaction was detected by immunological methods. Firstly, plates were incubated for 90 minutes at room temperature with anti-phosphotyrosine primary antibodies that were raised in the mouse (4G10 from Upstate Biotechnology). Following extensive washing, plates were treated with Horseradish Peroxidase (HRP) conjugated sheep anti-mouse secondary antibody (NXA931 from Amersham) for 60 minutes at room temperature. After further washing, HRP activity in each well of the plate was measured colorimetrically using 22'-Azino-di-[3-ethylbenzothiazoline sulfonate (6)] diammonium salt crystals (ABTS™ from Roche) as a substrate.

Quantification of colour development and thus enzyme activity was achieved by the measurement of absorbance at 405 nm on a Molecular Devices ThermoMax microplate reader. Kinase inhibition for a given compound was expressed as an IC$_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b) EGFR Driven KB Cell Proliferation Assay

This assay measures the ability of a test compound to inhibit the proliferation of human tumour cell line, KB (obtained from the American Type Culture Collection (ATCC)).

KB cells were cultured in Dulbecco's modified Eagle's medium (DMEM) containing 10% foetal calf serum, 2 mM glutamine and non-essential amino acids at 37° C. in a 7.5% CO$_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of 1.25×10$^3$ cells per well of a 96 well plate in DMEM containing 2.5% charcoal stripped serum, 1 mM glutamine and non-essential amino acids at 37° C. in 7.5% CO$_2$ and allowed to settle for 4 hours.

Following adhesion to the plate, the cells are treated with or without EGF (final concentration of 1 ng/ml) and with or without compound at a range of concentrations in dimethylsulfoxide (DMSO) (0.1% final) before incubation for 4 days. Following the incubation period, cell numbers were determined by addition of 50 µl of 3-(4,5-Dimethylthiazol-2-yl)-2,5-diphenyltetrazolium bromide (MTT) (stock 5 mg/ml) for 2 hours. MTT solution was then tipped off, the plate gently tapped dry and the cells dissolved upon the addition of 100 μl of DMSO.

Absorbance of the solubilised cells was read at 540 nm using a Molecular Devices ThermoMax microplate reader. Inhibition of proliferation was expressed as an $IC_{50}$ value. This was determined by calculation of the concentration of compound that was required to give 50% inhibition of proliferation. The range of proliferation was calculated from the positive (vehicle plus EGF) and negative (vehicle minus EGF) control values.

c) Clone 24 phospho-erbB2 Cell Assay

This immunofluorescence end point assay measures the ability of a test compound to inhibit the phosphorylation of erbB2 in a MCF7 (breast carcinoma) derived cell line which was generated by transfecting MCF7 cells with the full length erbB2 gene using standard methods to give a cell line that overexpresses full length wild type erbB2 protein (hereinafter 'Clone 24' cells).

Clone 24 cells were cultured in Growth Medium (phenol red free Dulbecco's modified Eagle's medium (DMEM) containing 10% foetal bovine serum, 2 mM glutamine and 1.2 mg/ml G418) in a 7.5% $CO_2$ air incubator at 37° C. Cells were harvested from T75 stock flasks by washing once in PBS (phosphate buffered saline, pH7.4, Gibco No. 10010-015) and harvested using 2 mls of Trypsin (1.25 mg/ml)/ethylaminediaminetetraacetic acid (EDTA) (0.8 mg/ml) solution. The cells were resuspended in Growth Medium. Cell density was measured using a haemocytometer and viability was calculated using Trypan Blue solution before being further diluted in Growth Medium and seeded at a density of $1\times10^4$ cells per well (in 100 ul) into clear bottomed 96 well plates (Packard, No. 6005182).

3 days later, Growth Medium was removed from the wells and replaced with 100 μl Assay Medium (phenol red free DMEM, 2 mM glutamine, 1.2 mg/ml G418) either with or without erbB inhibitor compound. Plates were returned to the incubator for 4 hours and then 20 μl of 20% formaldehyde solution in PBS was added to each well and the plate was left at room temperature for 30 minutes. This fixative solution was removed with a multichannel pipette, 100 μl of PBS was added to each well and then removed with a multichannel pipette and then 50 μl PBS was added to each well. Plates were then sealed and stored for up to 2 weeks at 4° C.

Immunostaining was performed at room temperature. Cells were washed once with 200 μl PBS/Tween 20 (made by adding 1 sachet of PBS/Tween dry powder (Sigma, No. P3563) to 1 L of double distilled $H_2O$) using a plate washer, then 100 μl of 0.5% Triton X-100/PBS was added to each well to permeabalise the cells. After 10 minutes, the plates were washed with 200 μl PBS/Tween 20 and then 100 μl Blocking Solution (5% Marvel dried skimmed milk (Nestle) in PBS) was added per well and the plates were incubated for 15 minutes. Following removal of the Blocking Solution with a plate washer, 30 μl of rabbit polyclonal anti-phospho erbB2 IgG antibody (epitope phospho-Tyr 1248, SantaCruz, No. SC-12352-R), diluted 1:250 in Blocking Solution, was added to each well and incubated for 2 hours. Then this primary antibody solution was removed from the wells using a plate washer followed by two 200 μl PBS/Tween 20 washes using a plate washer. 100 μl of Blocking solution was added per well and the plates were incubated for 10 minutes. Then 30 μl of Alexa-Fluor 488 goat anti-rabbit IgG secondary antibody (Molecular Probes, No. A-11008), diluted 1:750 in Blocking Solution, was added to each well. From now onwards, wherever possible, plates were protected from light exposure, at this stage by sealing with black backing tape. The plates were incubated for 45 minutes and then the secondary antibody solution was removed from the wells followed by three 200 μl PBS/Tween 20 washes using a plate washer. Then 100 μl PBS was added to each plate, incubated for 10 minutes and then removed using a plate washer. Then 50 μl of PBS was added to each well and plates were resealed with black backing tape and stored at 4° C. before analysis. Plates were analysed within six hours of completing the immunostaining.

The Fluorescence signal is each well was measured using an Acumen Explorer Instrument (Acumen Bioscience Ltd.), a plate reader that can be used to rapidly quantitate features of images generated by laser-scanning. The instrument was set to measure the number of fluorescent objects above a pre-set threshold value and this provided a measure of the phosphorylation status of erbB2 protein. Fluorescence dose response data obtained with each compound was exported into a suitable software package (such as Origin) to perform curve fitting analysis. Inhibition of erbB2 phosphorylation was expressed as an $IC_{50}$ value. This was determined by calculation of the concentration of compound that was required to give 50% inhibition of erbB2 phosphorylation signal.

d) In Vivo BT474C Xenograft Assay

This assay measures the ability of a test compound to inhibit the growth of a specific variant of the BT-474 tumour cell line grown as a xenograft in Female Swiss athymic mice (Alderley Park, nu/nu genotype) (Baselga, J. et al. (1998) *Cancer Research*, 58, 2825-2831).

The BT-474 tumour cell line (human mammary carcinoma) was obtained from Dr Baselga (at Laboratorio Recerca Oncologica, Paseo Vall D'Hebron 119-129, Barcelona 08035, Spain). This cell line was subcloned and a certain population (hereinafter referred to as "BT474C") was obtained.

Female Swiss athymic (nu/nu genotype) mice were bred and maintained in Alderley Park in negative pressure Isolators (PFI Systems Ltd.). Mice were housed in a barrier facility with 12 hour light/dark cycles and provided with sterilised food and water ad libitum. All procedures were performed on mice of at least 8 weeks of age. BT474C tumour cell xenografts were established in the hind flank of donor mice by sub-cutaneous injections of $1\times10^7$ freshly cultured cells in 100 μl of serum free media with 50% Matrigel per animal. Animals were supplemented with oestradiol benzoate (Mesalin, Intravet UK 0.2 mg/ml), 100 μg/animal injected subcutaneously on the day before cell implant, with subsequent weekly boosts of 50 μg/animal; or by implantation of 0.5 mg 21 day release oestrogen pellets (Innovative Research of America) on the day before cell implant. As an example, selection on day 14 post-implant, mice were randomised into groups of 10 prior to the treatment with compound or vehicle control that was administered once daily at 0.1 ml/10 g body weight. Tumour volume was assessed twice weekly by bilateral Vernier calliper measurement, using the formula (length×width)×√(length×width)×(π/6), where length was the longest diameter across the tumour, and width was the corresponding perpendicular. Growth inhibition from start of treatment was calculated by comparison of the mean changes in tumour volume for the control and treated groups, and statistical significance between the two groups was evaluated using a Students t test.

e) BT474C Cell Proliferation Assay

BT474C cells are a sub-cloned population of in vivo competent cells, as discussed above.

The BT474C assay is a MTS (3-(4,5-dimethylthiazol-2-yl)-5-(3-carboxymethoxyphenyl)-2-(4-sulfophenyl)-2H-tetrazolium, inner salt—Promega G1111) endpoint-based cell proliferation assay, which measures the ability of a test compound to inhibit the proliferation of cells over a four-day period. Cells are grown to logarithmic phase in growth media (phenol red free Dulbecco's modified Eagle's medium (DMEM) containing 10% foetal bovine serum, 10% M1 supplement (AstraZeneca internal supply), 1% oxaloacetic acid in a 7.5% $CO_2$ air incubator at 37° C. Cells are harvested from stock flasks by washing once in PBS (phosphate buffered saline, pH7.4, Gibco No. 10010-015) and removed using 2 mls of Trypsin (1.25 mg/ml)/ethylaminediaminetetraacetic acid (EDTA) (0.8 mg/ml) solution. The cells are re-suspended in assay media (phenol red free Dulbecco's modified Eagle's medium (DMEM) containing 10% charcoal/Dextran stripped foetal bovine serum, 10% M1 supplement, 1% oxaloacetic acid. Cell density is measured using a haemocytometer and viability is calculated using Trypan Blue solution before being further diluted in Assay Medium and seeded at a density of $1\times10^4$ cells per well (in 100 ul) into clear bottomed 96 well plates (Costar 3598). One extra plate is set up to act as a Day 0 control plate.

4 hours later, assay medium containing test compound, serially diluted in 100% DMSO (Sigma D5879), in the form of a dose response is added across the plate in triplicate. The Day 0 plate is treated with MTS solution (Tetrazolium compound—made from MTS powder in a Phenazine ethosulfate (PES—Sigma P4544)/PBS) and incubated for 2 hours before the reaction is stopped by the addition of 10% SDS. The plate is read at 490 nm on a spectrophotometer.

Assay plates are left at 37° C. for 4 days and then treated with MTS solution (as above), which is converted to a soluble formazan product by active cells. After incubating the plates for 2 hours the reaction is stopped by the addition of 10% SDS (Sodium dodecyl sulphate) and the plates are read at 490 nm on a spectrophotometer giving absorbance values relative to the concentration of converted dye.

Absorbance dose response data obtained with each compound is exported into a suitable software package (such as Origin) to perform curve-fitting analysis. Inhibition of BT474C cell proliferation is expressed as an $IC_{50}$ value (calculated as GI50 by use of a log/lin plot—analyzing data above the day 0 absorbance values). This is determined by calculation of the concentration of compound that is required to give 50% inhibition of cell proliferation.

f) hERG-Encoded Potassium Channel Inhibition Assay

Cell Culture for IonWorks™ HT:

The hERG-expressing Chinese hamster ovary K1 (CHO) cells described by Persson et al. (Persson, F., Carlsson, L., Duker, G., and Jacobson, I., Blocking characteristics of hERG, hNav1.5, and hKvLQT1/hminK after administration of the novel anti-arrhythmic compound AZD7009., J Cardiovasc. Electrophysiol., 16, 329-341.2005) were grown to semi-confluence at 37° C. in a humidified environment (5% $CO_2$) in F-12 Ham medium containing L-glutamine, 10% foetal calf serum (FCS) and 0.6 mg/ml hygromycin (all Sigma). Prior to use, the monolayer was washed using a pre-warmed (37° C.) 3 ml aliquot of Versene 1:5,000 (Invitrogen). After aspiration of this solution the flask was incubated at 37° C. in an incubator with a further 2 ml of Versene 1:5,000 for a period of 6 minutes. Cells were then detached from the bottom of the flask by gentle tapping and 10 ml of Dulbecco's-PBS containing calcium (0.9 mM) and magnesium (0.5 mM) (PBS; Invitrogen) was then added to the flask and aspirated into a 15 ml centrifuge tube prior to centrifugation (50 g, for 4 minutes). The resulting supernatant was discarded and the pellet gently re-suspended in 3 ml of PBS. A 0.5 ml aliquot of cell suspension was removed to determine viable cell number based on trypan blue exclusion (Cedex; Innovatis) and the cell re-suspension volume adjusted with PBS to give the desired final cell concentration. CHO-Kv1.5 cells, which were used to adjust the voltage offset on IonWorks™ HT, were maintained and prepared for use in the same way.

IonWorks™ HT Electrophysiology:

The principles and operation of this device have been described by Schroeder et al. (Schroeder, K., Neagle, B., Trezise, D. J., and Worley, J., Ionworks H T: a new high-throughput electrophysiology measurement platform, J Biomol Screen, 8, 50-64, 2003). Briefly, the technology is based on a 384-well plate (PatchPlate™) in which a recording is attempted in each well by using suction to position and hold a cell on a small hole separating two isolated fluid chambers. Once sealing has taken place, the solution on the underside of the PatchPlate™ is changed to one containing amphotericin B. This permeablises the patch of cell membrane covering the hole in each well and in effect allows a perforated, whole-cell patch clamp recording to be made.

IonWorks™ HT (a beta-test machine from Essen Instruments) was operated at room temperature (~21° C.) in the following way. The reservoir in the "Buffer" position was loaded with 4 ml of PBS and that in the "Cells" position with the CHO-hERG cell suspension described above. A 96-well plate (V-bottom, Greiner Bio-one) containing the compounds to be tested (at 3× their final test concentration) was placed in the "Plate 1" position and a PatchPlate™ was clamped into the PatchPlate™ station. Each compound plate was laid-out in 12 columns to enable ten, 8-point concentration-effect curves to be constructed; the remaining two columns on the plate were taken up with vehicle (final concentration 0.33% DMSO), to define the assay baseline, and a supra-maximal blocking concentration of cisapride (final concentration 10 µM), to define the 100% inhibition level. The fluidics-head (F-Head) of IonWorks™ HT then added 3.5 µl of PBS to each well of the PatchPlate™ and its underside was perfused with "internal" solution that had the following composition (in mM): K-Gluconate 100, KCl 40, $MgCl_2$ 3.2, EGTA 3 and HEPES 5 (all Sigma) (pH 7.25-7.30 using 10 M KOH). After priming and de-bubbling, the electronics-head (E-head) then moved round the PatchPlate™ performing a hole test (i.e. applying a voltage pulse to determine whether the hole in each well was open). The F-head then dispensed 3.5 µl of the cell suspension described above into each well of the PatchPlate™ and the cells were given 200 seconds to reach and seal to the hole in each well. Following this, the E-head moved round the PatchPlate™ to determine the seal resistance obtained in each well. Next, the solution on the underside of the PatchPlate™ was changed to "access" solution that had the following composition (in mM): KCl 140, EGTA 1, $MgCl_2$ 1 and HEPES 20 (pH 7.25-7.30 using 10 M KOH) plus 100 µg/ml of amphotericin B (all Sigma). After allowing 9 minutes for patch perforation to take place, the E-head moved round the PatchPlate™ 48 wells at a time to obtain pre-compound hERG current measurements. The F-head then added 3.5 µl of solution from each well of the compound plate to 4 wells on the PatchPlate™ (the final DMSO concentration was 0.33% in every well). This was achieved by moving from the most dilute to the most concentrated well of the compound plate to minimise the impact of any compound carry-over. After approximately three and a half minutes incubation, the E-head then moved around all 384-wells of the PatchPlate™ to obtain post-compound hERG current measurements. In this way, non-cumulative concentration-effect curves could be produced where, providing the acceptance criteria were achieved in a sufficient percentage of wells (see below), the effect of each concentration of test compound was based on recording from between 1 and 4 cells.

The pre- and post-compound hERG current was evoked by a single voltage pulse consisting of a 20 s period holding at −70 mV, a 160 ms step to −60 mV (to obtain an estimate of leak), a 100 ms step back to −70 mV, a 1 s step to +40 mV, a 2 s step to −30 mV and finally a 500 ms step to −70 mV. In between the pre- and post-compound voltage pulses there was no clamping of the membrane potential. Currents were leak-subtracted based on the estimate of current evoked during the +10 mV step at the start of the voltage pulse protocol. The current signal was sampled at 2.5 k Hz.

Pre- and post-scan hERG current magnitude was measured automatically from the leak subtracted traces by the IonWorks™ HT software by taking a 40 ms average of the current during the initial holding period at −70 mV (baseline current) and subtracting this from the peak of the tail current response. The acceptance criteria for the currents evoked in each well were: pre-scan seal resistance >60 MΩ, pre-scan hERG tail current amplitude >150 pA; post-scan seal resistance >60 MΩ. The degree of inhibition of the hERG current was assessed by dividing the post-scan hERG current by the respective pre-scan hERG current for each well.

Although the pharmacological properties of the quinazoline derivatives of the Formula I vary with structural change as expected, in general activity possessed by the quinazoline derivatives of the Formula I, may be demonstrated at the following concentrations or doses in one or more of the above tests (a), (b), (c), (d) and (e):—

| | |
|---|---|
| Test (a):- | $IC_{50}$ in the range, for example, 0.001-1 μM; |
| Test (b):- | $IC_{50}$ in the range, for example, 0.001-5 μM; |
| Test (c):- | $IC_{50}$ in the range, for example, 0.001-5 μM; |
| Test (d):- | activity in the range, for example, 1-200 mg/kg/day; |
| Test (e):- | $IC_{50}$ in the range, for example, 0.001-5 μM; |

No physiologically unacceptable toxicity was observed in Test (d) at the effective dose for quinazoline derivatives tested of the present invention. Test (f) shows a safe margin between target and hERG activity, suggesting the unlikelihood of arrhythmia caused by inhibition of the hERG channel. Accordingly no untoward toxicological effects are expected when a quinazoline derivative of the Formula I, or a pharmaceutically acceptable salt thereof, as defined hereinbefore is administered at the dosage ranges defined hereinafter.

By way of example, Table A illustrates the activity of representative compounds according to the invention. Column 2 of Table A shows $IC_{50}$ data from Test (a) for the inhibition of EGFR tyrosine kinase protein phosphorylation; column 3 shows $IC_{50}$ data from Test (a) for the inhibition of erbB2 tyrosine kinase protein phosphorylation; and column 4 shows $IC_{50}$ data for inhibition of phosphorylation of erbB2 in a MCF7 derived cell line in Test (c) described above:

TABLE A

| Example Number | $IC_{50}$ (μM) Test (a): Inhibition of EGFR tyrosine kinase protein phosphorylation | $IC_{50}$ (μM) Test (a): Inhibition of erbB2 tyrosine kinase protein phosphorylation | $IC_{50}$ (μM) Test (c): Inhibition of erbB2 tyrosine kinase protein phosphorylation |
|---|---|---|---|
| 1 | 0.21 | 0.012 | — |
| 2 | 0.032 | 0.003 | 0.035 |

According to a further aspect of the invention there is provided a pharmaceutical composition which comprises a quinazoline derivative of the Formula I, or a pharmaceutically acceptable thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a quinazoline derivative of the Formula I will naturally vary according to the nature and severity of the conditions, the age and sex of the animal or patient and the route of administration, according to well known principles of medicine.

In using a quinazoline derivative of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a quinazoline derivative of this invention.

We have found that the quinazoline derivatives of the present invention possess anti-proliferative properties such as anti-cancer properties that are believed to arise from their erbB, particularly EGF and more particularly erbB2 receptor tyrosine kinase inhibitory activity. Furthermore, certain of the quinazoline derivatives according to the present invention possess substantially better potency against the erbB2 receptor tyrosine kinase, than against other tyrosine kinases enzymes, such as EGFR tyrosine kinase. Such quinazoline derivatives possess sufficient potency against the erbB2 receptor tyrosine kinase that they may be used in an amount sufficient to inhibit erbB2 receptor tyrosine kinase whilst demonstrating little, or significantly lower, activity against other tyrosine kinases such as EGFR. Such quinazoline derivatives are likely to be useful for the selective inhibition of erbB2 receptor tyrosine kinase and are likely to be useful for the effective treatment of, for example, erbB2 driven tumours.

Accordingly, the quinazoline derivatives of the present invention are expected to be useful in the treatment of diseases or medical conditions mediated alone or in part by and erbB, particularly erbB2 receptor tyrosine kinases, i.e. the quinazoline derivatives may be used to produce an erbB, particularly an erbB2, receptor tyrosine kinase inhibitory effect in a warm-blooded animal in need of such treatment. Thus the quinazoline derivatives of the present invention provide a method for the treatment of malignant cells characterised by inhibition of the erbB, particularly the erbB2, receptor tyrosine kinase. Particularly the quinazoline derivatives of the invention may be used to produce an anti-proliferative and/or pro-apoptotic and/or anti-invasive effect mediated alone or in part by the inhibition of erbB, particularly erbB2, receptor tyrosine kinases. Particularly, the quinazoline derivatives of the present invention are expected to be useful in the prevention or treatment of those tumours that are sensitive to inhibition of an erbB, particularly the erbB2, receptor tyrosine kinase that are involved in the signal transduction steps which drive proliferation and survival of these tumour cells. Accordingly the quinazoline derivatives of the present invention are expected to be useful in the treatment and/or prevention of a number of hyperproliferative disorders by providing an anti-proliferative effect. These disorders include, for example psoriasis, benign prostatic hyperplasia (BPH), atherosclerosis and restenosis and, in particular, erbB, more particularly erbB2, receptor tyrosine kinase driven tumours. Such benign or malignant tumours may affect any tissue and include non-solid tumours such as leukaemia, multiple myeloma or lymphoma, and also solid tumours, for example bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval tumours.

According to this aspect of the invention there is provided a quinazoline derivative of the Formula I, or a pharmaceutically acceptable salt thereof, for use as a medicament.

Thus according to this aspect of the invention there is provided the use of a quinazoline derivative of the Formula I, or a pharmaceutically acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline derivative of the Formula I, or a pharmaceutically acceptable salt thereof, as hereinbefore defined.

According to a further aspect of the invention there is provided a quinazoline derivative of the Formula I, or a pharmaceutically acceptable salt thereof, for use in the production of an anti-proliferative effect in a warm-blooded animal such as man.

According to a further aspect of the invention there is provided the use of a quinazoline derivative of the Formula I, or a pharmaceutically acceptable salt thereof, as defined hereinbefore in the manufacture of a medicament for use in the production of an anti-proliferative effect which effect is produced alone or in part by inhibiting erbB2 receptor tyrosine kinase in a warm-blooded animal such as man.

According to a further feature of this aspect of the invention there is provided a method for producing an anti-proliferative effect which effect is produced alone or in part by inhibiting erbB2 receptor tyrosine kinase in a warm-blooded animal, such as man, in need of such treatment which comprises administering to said animal an effective amount of a quinazoline derivative of the Formula I, or a pharmaceutically acceptable salt thereof, as hereinbefore defined.

According to a further aspect of the invention there is provided a quinazoline derivative of the Formula I, or a pharmaceutically acceptable salt thereof, for use in the production of an anti-proliferative effect which effect is produced alone or in part by inhibiting erbB2 receptor tyrosine kinase in a warm-blooded animal such as man.

According to a further aspect of the present invention there is provided the use of a quinazoline derivative of the Formula I, or a pharmaceutically acceptable salt thereof, as defined hereinbefore in the manufacture of a medicament for use in the treatment of a disease or medical condition (for example a cancer as mentioned herein) mediated alone or in part by erbB, particularly erbB2, receptor tyrosine kinase.

According to a further feature of this aspect of the invention there is provided a method for treating a disease or medical condition (for example a cancer as mentioned herein) mediated alone or in part by erbB, particularly erbB2, receptor tyrosine kinase in a warm-blooded animal, such as man, in need of such treatment, which comprises administering to said animal an effective amount of a quinazoline derivative of the Formula I, or a pharmaceutically acceptable salt thereof, as defined hereinbefore.

According to a further aspect of the invention there is provided a quinazoline derivative of the Formula I, or a pharmaceutically acceptable salt thereof, for use in the treatment of a disease or medical condition (for example a cancer as mentioned herein) mediated alone or in part by erbB, particularly erbB2, receptor tyrosine kinase.

According to a further aspect of the invention there is provided the use of a quinazoline derivative of the Formula I, or a pharmaceutically acceptable salt thereof, as defined hereinbefore in the manufacture of a medicament for use in the prevention or treatment of those tumours which are sensitive to inhibition of one or more erbB receptor tyrosine kinases, such as EGF and/or erbB2 and/or erbB4 (especially erbB2) receptor tyrosine kinase that are involved in the signal transduction steps which lead to the proliferation of tumour cells.

According to a further feature of this aspect of the invention there is provided a method for the prevention or treatment of those tumours which are sensitive to inhibition of one or more erbB receptor tyrosine kinases, such as EGF and/or erbB2 and/or erbB4 (especially erbB2) receptor tyrosine kinase, that are involved in the signal transduction steps which lead to the proliferation and/or survival of tumour cells in a warm-blooded animal, such as man, in need of such treatment, which comprises administering to said animal an effective amount of a quinazoline derivative of the Formula I, or a pharmaceutically acceptable salt thereof, as defined hereinbefore.

According to a further aspect of the invention there is provided a quinazoline derivative of the Formula I, or a pharmaceutically acceptable salt thereof, for use in the prevention or treatment of those tumours which are sensitive to inhibition of one or more erbB receptor tyrosine kinases, such as EGF and/or erbB2 and/or erbB4 (especially erbB2) receptor tyrosine kinase, that are involved in the signal transduction steps which lead to the proliferation and/or survival of tumour cells.

According to a further aspect of the invention there is provided the use of a quinazoline derivative of the Formula I, or a pharmaceutically acceptable salt thereof, as defined hereinbefore in the manufacture of a medicament for use in providing an EGF and/or erbB2 and/or erbB4 (especially erbB2) receptor tyrosine kinase inhibitory effect.

According to a further feature of this aspect of the invention there is provided a method for providing an EGF and/or erbB2 and/or erbB4 (especially erbB2) receptor tyrosine kinase inhibitory effect in a warm-blooded animal, such as man, in need of such treatment, which comprises administering to said animal an effective amount of a quinazoline derivative of the Formula I, or a pharmaceutically acceptable salt thereof, as defined hereinbefore.

According to a further aspect of the invention there is provided a quinazoline derivative of the Formula I, or a pharmaceutically acceptable salt thereof, for use in providing an EGF and/or erbB2 and/or erbB4 (especially erbB2) receptor tyrosine kinase inhibitory effect.

According to a further aspect of the invention there is provided the use of a quinazoline derivative of the Formula I, or a pharmaceutically acceptable salt thereof, as defined hereinbefore in the manufacture of a medicament for use in providing a selective erbB2 kinase inhibitory effect.

According to a further feature of this aspect of the invention there is provided a method for providing a selective erbB2 kinase inhibitory effect in a warm-blooded animal, such as man, in need of such treatment, which comprises administering to said animal an effective amount of a quinazoline derivative of the Formula I, or a pharmaceutically acceptable salt thereof, as defined hereinbefore.

According to a further aspect of the invention there is provided a quinazoline derivative of the Formula I, or a pharmaceutically acceptable salt thereof, for use in providing a selective erbB2 kinase inhibitory effect.

By "a selective erbB2 kinase inhibitory effect" is meant that the quinazoline derivative of the Formula I is more potent against erbB2 receptor tyrosine kinase than it is against other kinases. In particular some of the compounds according to the invention are more potent against erbB2 receptor kinase than it is against other tyrosine kinases such as other erbB receptor tyrosine kinases, particularly EGFR tyrosine kinase. For example a selective erbB2 kinase inhibitor according to the invention is at least 5 times, preferably at least 10 times more potent against erbB2 receptor tyrosine kinase than it is against EGFR tyrosine kinase, as determined from the relative $IC_{50}$ values in suitable assays (for example the by comparing the $IC_{50}$ value from the Clone 24 phospho-erbB2 cell assay (a measure of the erbB2 tyrosine kinase inhibitory activity in cells) with the $IC_{50}$ from the KB cell assay (a measure of the EGFR tyrosine kinase inhibitory activity in cells) for a given test compound as described above).

According to a further aspect of the present invention there is provided the use of a quinazoline derivative of the Formula I, or a pharmaceutically acceptable salt thereof, as defined hereinbefore in the manufacture of a medicament for use in the treatment of a cancer, for example a cancer selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer.

According to a further feature of this aspect of the invention there is provided a method for treating a cancer, for example a cancer selected from selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer in a warm-blooded animal, such as man, in need of such treatment, which comprises administering to said animal an effective amount of a quinazoline derivative of the Formula I, or a pharmaceutically acceptable salt thereof, as defined hereinbefore.

According to a further aspect of the invention there is provided a quinazoline derivative of the Formula I, or a pharmaceutically acceptable salt thereof, for use in the treatment of a cancer, for example a cancer selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer.

As mentioned above the size of the dose required for the therapeutic or prophylactic treatment of a particular disease will necessarily be varied depending upon, amongst other things, the host treated, the route of administration and the severity of the illness being treated.

The quinazoline derivatives of the invention may be administered in the form of a pro-drug, by which we mean a compound that is broken down in a warm-blooded animal, such as man, to release a quinazoline derivative of the invention. A pro-drug may be used to alter the physical properties and/or the pharmacokinetic properties of a quinazoline derivative of the invention. A pro-drug can be formed when the quinazoline derivative of the invention contains a suitable group or substituent to which a property-modifying group can be attached. Examples of pro-drugs include in vivo cleavable ester derivatives that may be formed at a hydroxy group in a quinazoline derivative of the Formula I and in vivo cleavable amide derivatives that may be formed at an amino group in a quinazoline derivative of the Formula I.

Accordingly, the present invention includes those quinazoline derivatives of the Formula I as defined hereinbefore when made available by organic synthesis and when made available within the human or animal body by way of cleavage of a pro-drug thereof. Accordingly, the present invention includes those quinazoline derivatives of the Formula I that are produced by organic synthetic means and also such quinazoline derivatives that are produced in the human or animal body by way of metabolism of a precursor compound, that is a quinazoline derivative of the Formula I may be a synthetically-produced quinazoline derivative or a metabolically-produced quinazoline derivative.

A suitable pharmaceutically acceptable pro-drug of a quinazoline derivative of the Formula I is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309 to 396, edited by K. Widder, et al. (Academic Press, 1985);

b) Design of Pro-drugs, edited by H. Bundgaard, (Elsevier, 1985);

c) A Textbook of Drug Design and Development, edited by Krogsgaard-Larsen and H. Bundgaard, Chapter 5 "Design and Application of Pro-drugs", edited by H. Bundgaard, p. 113 to 191 (1991);

d) H. Bundgaard, *Advanced Drug Delivery Reviews*, 8, 1 to 38 (1992); and e) H. Bundgaard, et al., *Journal of Pharmaceutical Sciences*, 77, 285 (1988).

The anti-proliferative treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [Erbitux, C225]); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 and AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), compounds such as those disclosed in International Patent Applications WO 97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the quinazoline derivatives of this invention within the dosage range described hereinbefore and the other pharmaceutically-active agent within its approved dosage range.

According to this aspect of the invention there is provided a pharmaceutical product comprising a quinazoline derivative of the Formula I as defined hereinbefore and an additional anti-tumour agent as defined hereinbefore for the conjoint treatment of cancer.

Although the quinazoline derivatives of the Formula I are primarily of value as therapeutic agents for use in warm-blooded animals (including man), they are also useful whenever it is required to inhibit the effects of the erbB receptor tyrosine protein kinases. Thus, they are useful as pharmacological standards for use in the development of new biological tests and in the search for new pharmacological agents.

The invention will now be illustrated by the following non-limiting examples in which, unless stated otherwise:

(i) temperatures are given in degrees Celsius (° C.); operations were carried out at room or ambient temperature, that is, at a temperature in the range of 18 to 25° C.;

(ii) organic solutions were dried over anhydrous magnesium sulfate or anhydrous sodium sulfate; evaporation of solvent was carried out using a rotary evaporator under reduced pressure (600 to 4000 Pascals; 4.5 to 30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and/or analytical LC-MS, and reaction times are given for illustration only. The retention times ($t_R$) were measured on a LC/MS Waters 2790/ZMD Micromass system equipped with a Waters Symmetry column (C18, 3.5 μM, 4.6×50 mm); detection UV 254 nM and MS; elution: flow rate 2.5 ml/min, linear gradient from 95% water-5% methanol containing 5% formic acid to 40% water-55% acetonitrile-5% methanol containing 5% formic acid over 3 minutes; then linear gradient to 95% acetonitrile-5% methanol containing 5% formic acid over 1 minute;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 400 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; br, broad;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is (MH)$^+$ which refers to the protonated mass ion; reference to M$^+$ is to the mass ion generated by loss of an electron; and reference to M-H+ is to the mass ion generated by loss of a proton;

(xi) unless stated otherwise compounds containing an asymmetrically substituted carbon and/or sulfur atom have not been resolved;

(xii) where a synthesis is described as being analogous to that described in a previous example the amounts used are the millimolar ratio equivalents to those used in the previous example;

(xiii) all microwave reactions were carried out in a Personal Chemistry EMRYS™ Optimizer EXP microwave synthesisor;

(xiv) preparative high performance liquid chromatography (HPLC) was performed on a Waters instrument using the following conditions:

| | |
|---|---|
| Column: | 30 mm × 15 cm Xterra Waters, C18, 5 mm |
| Solvent A: | Water with 1% acetic acid or 2 g/l ammonium carbonate |
| Solvent B: | Acetonitrile |
| Flow rate: | 40 ml/min |
| Run time: | 15 minutes with a 10 minute gradient from 5-95% B |
| Wavelength: | 254 nm |
| Injection volume | 2.0-4.0 ml; |

(xv) the following abbreviations have been used:
HATU O-(7-azabenzotriazol-1-yl)-N,N,N',N'-tetramethyluronium hexafluoro-phosphate; and
THF tetrahydrofuran;
DMF N,N-dimethylformamide;
DMA N,N-dimethylacetamide;
DCM dichloromethane;
DMSO dimethylsulfoxide;
DTAD di-tert-butyl azodicarboxylate;
DIPEA di-isopropylethylamine;
IPA isopropyl alcohol;
Ether diethyl ether; and
TFA trifluoroacetic acid.

EXAMPLE 1

(2R)—N-(2-Hydroxyethyl)-N-methyl-2-[(4-{[1-(pyridin-2-ylmethyl)-1H-indazol-5-yl]amino}quinazolin-5-yl)oxy]propanamide A stirred suspension of methyl (2R)-2-[(4-{[1-(pyridin-2-ylmethyl)-1H-indazol-5-yl]amino}quinazolin-5-yl)oxy]propanoate (200 mg, 0.44 mmol) in 2-(methylamino)-ethanol (2 ml) was heated in a microwave reactor at 100° C. for 30 minutes. The 2-(methylamino)-ethanol was evaporated under high vacuum and the residue was partitioned between water and DCM. The organic phase was washed with brine, dried and evaporated to a gum. The title compound was isolated by chromatography (silica, 5% 2M NH$_3$-methanol in DCM) as a white solid after trituration with ether (126 mg, 58%); NMR spectrum (393 K) 1.65 (d, 3H), 3.07 (s, 2H), 3.39-3.66 (m, 5H), 4.40 (s, 1H), 5.71 (s, 2H), 5.76-5.83 (m, 1H), 7.05 (d, 1H), 7.20 (d, 1H), 7.23-7.28 (m, 1H), 7.35 (d, 1H), 7.58 (d, 1H), 7.65-7.73 (m, 2H), 7.84 (dd, 1H), 8.07 (s, 1H), 8.45 (s, 1H), 8.48 (s, 1H), 8.52 (d, 1H), 10.86 (s, 1H); Mass spectrum MH$^+$ 498.

The methyl (2R)-2-[(4-{[1-(pyridin-2-ylmethyl)-1H-indazol-5-yl]amino}quinazolin-5-yl)oxy]propanoate used as starting material was prepared as follows:

DMF (0.2 ml) was added to a suspension of 5-fluoro-3,4-dihydro-3H-quinazolin-4-one (1.64 g) in thionyl chloride (10 ml) and the mixture was stirred and heated at 80° C. for 6 hours. Volatile material was removed by evaporation and the residue was azeotroped with toluene (20 ml). The resulting solid was added portion-wise to a vigorously stirred mixture of saturated sodium bicarbonate (50 ml), crushed ice (50 g) and DCM (50 ml) such that the temperature was kept below 5° C. The organic phase was separated, dried and concentrated to give 4-chloro-5-fluoroquinazoline as a solid which was used without purification (1.82 g, 99%); NMR spectrum (300 MHz, CDCl$_3$) 7.35-7.45 (m, 1H), 7.85-7.95 (m, 2H), 9.0 (s, 1H).

A stirred partial solution of 4-chloro-5-fluoroquinazoline (10.95 g, 60 mmol) and 5-aminoindazole (7.98 g, 60 mmol) in isopropanol (300 ml) was heated under reflux for 3 hours. On cooling to ambient temperature the product hydrochloride salt was filtered off and washed with isopropanol and ether. The salt was heated with water (400 ml)/ethanol (100 ml) and the partial solution was basified with aqueous ammonia. The precipitated solid was filtered off and washed with water to provide 5-fluoro-N-1H-indazol-5-ylquinazolin-4-amine (14.91 g, 89%); NMR spectrum (300 MHz) 7.42 (dd, 1H), 7.53 (s, 2H), 7.60 (d, 1H), 7.83 (m, 1H), 8.08 (d, 2H), 8.50 (s, 1H), 9.20 (d, 1H), 13.05 (s, 1H); Mass spectrum MH$^+$ 280.

To a stirred partial solution of 5-fluoro-N-1H-indazol-5-ylquinazolin-4-amine (3.35 g, 12 mmol) and 2-picolyl chloride hydrochloride (2.07 g, 12.6 mmol) in DMF (60 ml) was added portion-wise, sodium hydride (60% dispersion in mineral oil, 1.01 g, 25.2 mmol). The reaction was maintained at ambient temperature by slight cooling and stirred for 18 hours. The reaction mixture was quenched by addition of saturated aqueous ammonium chloride solution (5 ml) and evaporated under high vacuum. The residue was partitioned between 2.5M aqueous NaOH and DCM and the organic phase was dried over anhydrous Na$_2$SO$_4$ and evaporated. The product was purified by chromatography (5% methanol/ethyl acetate) and the crystallized by trituration with ether to give 5-fluoro-N-[1-(pyridin-2-ylmethyl)-1H-indazol-5-yl]quinazolin-4-amine (1.8 g, 41%); NMR spectrum (300 MHz) 5.75 (s, 2H), 6.97 (d, 1H), 7.27 (m, 1H), 7.41 (dd, 1H), 7.54-7.75 (m, 4H), 7.84 (q, 1H), 8.12 (d, 2H), 8.50 (m, 2H), 9.23 (d, 1H); Mass spectrum MH$^+$ 371.

To a stirred suspension of sodium hydride (60% in mineral oil, 1.68 g, 42 mmol) in DMA (25 ml) was slowly added N-(2-hydroxyethyl)acetamide (1.80 g, 17.5 mmol). When the effervescence had subsided, 5-fluoro-N-[1-(pyridin-2-ylmethyl)-1H-indazol-5-yl]quinazolin-4-amine (2.60 g, 7.0 mmol) was added and the mixture was heated at 120° C. for 18 hours. The reaction was quenched by addition of saturated aqueous NH$_4$Cl (5 ml) and evaporated (high vacuum). The residue was stirred with water (100 ml) giving a gelatinous precipitate, which was filtered off and washed with water. The product was purified by chromatography (silica, dry loaded, 5 to 10% methanol/DCM) and crystallized by trituration with ether to give 4-{[1-(pyridin-2-ylmethyl)-1H-indazol-5-yl]amino}quinazolin-5-ol (928 mg, 32%); NMR spectrum (373 K) 5.72 (s, 2H), 6.77 (m, 3H), 7.03 (d, 1H), 7.23 (dd, 1H), 7.44 (t, 1H), 7.50 (d, 1H), 7.59 (d, 1H), 7.70 (t, 1H), 8.07 (s, 1H), 8.13 (s, 1H), 8.27 (s, 1H), 8.52 (d, 1H), 11.87 (br s, 1H); Mass spectrum MH$^+$ 369.

To a stirred partial solution of 4-{[1-(pyridin-2-ylmethyl)-1H-indazol-5-yl]amino}quinazolin-5-ol (870 mg, 2.36 mmol), methyl (2S)-2-hydroxypropanoate (368 mg, 3.54 mmol) and triphenylphosphine (927 mg, 3.54 mmol) in DCM (20 ml) was added DTAD (814 mg, 3.54 mmol). The mixture was stirred for 1 hour, becoming a clear solution. The solution was extracted with 2N aqueous hydrogen chloride, discarding the organic phase. The aqueous phase was basified with aqueous ammonia and extracted with DCM. The organic phase was washed with brine, dried and evaporated to an oil which crystallised on trituration with ether to give methyl (2R)-2-[(4-{[1-(pyridin-2-ylmethyl)-1H-indazol-5-yl]amino}quinazolin-5-yl)oxy]propanoate (789 mg, 74%); NMR spectrum (300 MHz) 1.70 (d, 3H), 3.78 (s, 3H), 5.51 (q, 1H), 5.76 (s, 2H), 6.95 (d, 1H), 7.16 (d, 1H), 7.28 (dd, 1H), 7.37 (d, 1H), 7.69 (m, 4H), 8.16 (s, 1H), 8.43 (s, 1H), 8.52 (s, 2H), 10.48 (s, 1H); Mass spectrum MH$^+$ 455.

EXAMPLE 2

5-[(1R)-1-Methyl-2-morpholin-4-yl-2-oxoethoxy]-N-[1-(pyridin-2-ylmethyl)-1H-indazol-5-yl]quinazolin-4-amine To a stirred solution of morpholine (2 ml) in methanol (10 ml), was added 4 A molecular sieve powder (2 g). After stirring for 10 minutes, (6R)-6-methyl-4-[1-(pyridin-2-ylmethyl)-1H-indazol-5-yl]-4H-[1,4]oxazepino[5,6,7-de]quinazolin-5(6H)-one (125 mg, 0.3 mmol) was added and the mixture was stirred for 3 days. The reaction mixture was filtered and the solvent was evaporated. The residue was taken into DCM and washed with aqueous ammonia and brine, dried and evaporated to a gum. The product was purified by chromatography (silica, 5% methanol/DCM) and crystallized by trituration with ether to give the title compound (75 mg, 50%); NMR spectrum (373 K) 1.63 (d, 3H), 3.58-3.66 (m, 8H), 5.72 (s, 2H), 5.81 (q, 1H), 7.04 (d, 1H), 7.22 (d, 1H), 7.26 (dd, 1H), 7.36 (d, 1H), 7.59 (d, 1H), 7.67-7.73 (m, 2H), 7.83 (dd, 1H), 8.08 (d, 1H), 8.45 (d, 1H), 8.49 (s, 1H), 8.52 (d, 1H), 10.90 (s, 1H); Mass spectrum MH$^+$ 510.

The (6R)-6-methyl-4-[1-(pyridin-2-ylmethyl)-1H-indazol-5-yl]-4H-[1,4]oxazepino[5,6,7-de]quinazolin-5(6H)-one used as starting material was prepared as follows:

To a stirred solution of methyl (2R)-2-[(4-{[1-(pyridin-2-ylmethyl)-1H-indazol-5-yl]amino}quinazolin-5-yl)oxy]propanoate (520 mg, 1.15 mmol) (obtained as described in example 1, preparation of starting materials) in methanol (10 ml), was added 2.5M aqueous sodium hydroxide (2 ml, 5 mmol) and the solution was stirred for 3 hours. The solution was evaporated and the residue was taken into water and was acidified to about pH4 with acetic acid and stirred for 15 minutes. The precipitate was filtered off, washed with water and dried to provide (2R)-2-[(4-{[1-(pyridin-2-ylmethyl)-1H-indazol-5-yl]amino}quinazolin-5-yl)oxy]propanoic acid, (435 mg, 86%); NMR spectrum (300 MHz) 1.69 (d, 3H), 5.36 (q, 1H), 5.75 (s, 2H), 6.94 (d, 1H), 7.14 (d, 1H), 7.27 (t, 1H), 7.35 (d, 1H), 7.71 (m, 4H), 8.12 (s, 1H), 8.43 (s, 1H), 8.52 (s, 2H), 10 76 (s, 1H), one exchangeable not observed; Mass spectrum MH$^+$ 441.

To a stirred solution of (2R)-2-[(4-{[1-(pyridin-2-ylmethyl)-1H-indazol-5-yl]amino}quinazolin-5-yl)oxy]propanoic acid (415 mg, 0.94 mmol) in DMA (8 ml) was added DIPEA (1 ml) and HATU (447 mg, 1.18 mmol) and the solution was heated at 80° C. for 90 minutes. More HATU (223 mg, 0.59 mmol) was added and the reaction mixture was heated at 70° C. for a further 60 minutes. The solvent was evaporated (high vacuum) and the residue was taken into DCM. The product was washed with aqueous ammonia and brine, dried and evaporated to a gum. The gum was purified by chromatography (silica, 2% methanol/ethyl acetate) and the product crystallized by trituration with ether to give (6R)-6-methyl-4-[1-(pyridin-2-ylmethyl)-1H-indazol-5-yl]-4H-[1,4]oxazepino[5,6,7-de]quinazolin-5(6H)-one (316 mg, 80%); NMR spectrum (300 MHz) 1.55 (d, 3H), 5.25 (q, 1H), 5.75 (s, 2H), 7.17 (d, 1H), 7.30 (m, 3H), 7.68 (m, 4H), 7.91 (t, 1H), 8.10 (s, 1H), 8.50 (d, 1H), 8.75 (s, 1H); Mass spectrum MH$^+$ 423.

EXAMPLE 3

(2R)—N,N-Dimethyl-2-[(4-{[1-(pyridin-2-ylmethyl)-1H-indazol-5-yl]amino}quinazolin-5-yl)oxy]propanamide A mixture of (2R)—N,N-dimethyl-2-[(4-oxo-3,4-dihydroquinazolin-5-yl)oxy]propanamide (783 mg, 3 mmol), triphenylphosphine (2.35 g, 9 mmol) and carbon tetrachloride (8.62 ml, 90 mmol) in 1,2-dichloroethane (20 ml) was stirred at 45° C. for 2 hours. The mixture was cooled and the solvents were evaporated under vacuum. 1-(Pyridin-2-ylmethyl)-1H-indazol-5-amine (706 mg, 3.15 mmol) and acetonitrile (15 ml) were added. The mixture was stirred at 75° C. for 1 hour. After cooling, the solvents were evaporated under vacuum. The residue was diluted in DCM and extracted with 2N hydrochloric acid. The aqueous layer was neutralised by addition of 6N aqueous ammonia and extracted with DCM. The DCM layer was dried over magnesium sulfate and the solvents were evaporated under vacuum. The residue was purified twice by chromatography on silica gel (first eluant: 3% 6N methanolic ammonia in DCM; second eluant: 3% methanol in DCM) to give the title compound as a white foam (600 mg, 43%); NMR Spectrum (CDCl$_3$) 1.72 (d, 3H), 3.06 (s, 3H), 3.14 (s, 3H), 5.43 (q, 1H), 5.75 (s, 2H), 6.81 (m, 2H), 7.17 (m, 1H), 7.41 (d, 1H), 7.48 (d, 1H), 7.62-7.53 (m, 2H), 7.81 (dd, 1H), 8.10 (s, 1H), 8.44 (d, 1H), 8.58 (d, 1H), 8.62 (s, 1H); Mass spectrum 468.

The (2R)—N,N-dimethyl-2-[(4-oxo-3,4-dihydroquinazolin-5-yl)oxy]propanamide used as starting material was prepared as follows:

Sodium hydride (1.24 g, 60% in oil, 31 mmol) was added portion-wise to a solution of 5-methoxyquinazolin-4(3H)-one (5 g, 28.4 mmol; obtained as described in WO-96/09294) in anhydrous DMF (50 ml) while maintaining the temperature at 25° C. The mixture was stirred at room temperature for 30 minutes. Chloromethyl pivalate (4.45 ml, 31 mmol) was added at room temperature for 3 hours. Additional sodium hydride (0.12 g, 3 mmol) and chloromethyl pivalate (0.67 ml, 4.5 mmol) were added and the mixture was stirred another hour. After evaporation of the solvents under high vacuum, the mixture was diluted with water and extracted with DCM. After drying with magnesium sulfate and evaporation of the solvents, the residue was purified by chromatography on silica gel (eluant: ethyl acetate-petroleum ether, 6:4 to 8:2) to give (5-methoxy-4-oxoquinazolin-3(4H)-yl)methyl pivalate as a white solid (7.4 g, 90%); HPLC t$_R$: 2.69 min; Mass spectrum MH$^+$ 291.

Magnesium bromide (7 g, 38 mmol) was added to a solution of (5-methoxy-4-oxoquinazolin-3(4H)-yl)methyl pivalate (7.4 g, 25.5 mmol) in pyridine (25 ml). The mixture was stirred at 120° C. for one hour. After cooling, the solvents were evaporated under high vacuum. Diluted acetic acid (15 ml in 100 ml water) was added. The precipitated solid was filtered, washed with water and dried under high vacuum in the presence of P$_2$O$_5$ to give (5-hydroxy-4-oxoquinazolin-3(4H)-yl)methyl pivalate as a white solid (6.33 g, 90%); NMR Spectrum (CDCl$_3$) 1.23 (s, 9H), 5.93 (s, 2H), 6.99 (d, 1H), 7.22 (d, 1H), 7.68 (t, 1H), 8.21 (s, 1H); Mass spectrum MH$^+$ 277.

DTAD (13.34 g, 58 mmol) was added portion-wise to an ice-cooled solution of (5-hydroxy-4-oxoquinazolin-3(4H)-yl)methyl pivalate (8 g, 29 mmol), triphenylphosphine (15.2 g, 58 mmol) and (S)—N,N-dimethyl lactamide (5.1 g, 43.5 mmol; obtained as described in Larcheveque M., Synthesis 1986, 1, 60) in DCM (300 ml). The mixture was stirred at room temperature for one hour. After evaporation of the solvents under vacuum, the residue was diluted with 6N methanolic ammonia (100 ml). The mixture was stirred at room temperature for 18 hours. After evaporation of the solvents, the residue was triturated in ether. The resulting solid was filtered and purified further by chromatography on silica gel (eluant: 3 to 5% methanol in DCM) to give (2R)—N,N-dimethyl-2-[(4-oxo-3,4-dihydroquinazolin-5-yl)oxy]propanamide as a white solid (5.4 g, 71%); NMR Spectrum (CDCl$_3$) 1.77 (d, 3H), 2.94 (s, 3H), 3.19 (s, 3H), 5.10 (q, 1H), 6.92 (d, 1H), 7.35 (d, 1H), 7.63 (t, 1H), 8.00 (s, 1H); Mass spectrum MH$^+$ 262.

The 1-(pyridin-2-ylmethyl)-1H-indazol-5-amine used as starting material was prepared as follows:

A mixture of 5-nitroindazole (40.75 g, 250 mmol), picolyl chloride hydrochloride (45.1 g, 275 mmol) and potassium carbonate (72.4 g, 525 mmol) in DMF (400 ml) was heated at 75° C. for 3 hours. Additional picolyl chloride hydrochloride (4.1 g, 25 mmol) and potassium carbonate (3.45 g, 25 mmol) were added and the mixture was heated at 75° C. for 2 additional hours. After cooling, the mixture was diluted with water (800 ml). The precipitate was filtered, washed with water and dried. The resulting solid was purified by chromatography on silica gel (eluant: 50% ethyl acetate in petroleum ether) to give 5-nitro-1-(pyridin-2-ylmethyl)-1H-indazole as a solid (34.5 g, 55%); NMR Spectrum (CDCl$_3$) 5.77 (s, 2H), 7.03 (d, 1H), 7.23 (m, 1H), 7.55 (d, 1H), 7.63 (m, 1H), 8.27-8.23 (m, 2H), 8.58 (m, 1H), 8.74 (d, 1H); Mass spectrum MH$^+$ 255.

Further elution gave 5-nitro-2-(pyridin-2-ylmethyl)-2H-indazole; NMR Spectrum (CDCl$_3$) 5.76 (s, 2H), 7.26 (m, 2H), 7.77-7.69 (m, 2H), 8.10 (dd, 1H), 8.42 (s, 1H), 8.61 (m, 1H), 8.74 (d, 1H); Mass spectrum MH$^+$ 255.

A mixture of 5-nitro-1-(pyridin-2-ylmethyl)-1H-indazole (34 g, 134 mmol) and platinum(IV) oxide (1 g) in methanol (500 ml) was hydrogenated under a 1 bar pressure. After 4 hours (when absorption of hydrogen had stopped), the mixture was filtered on celite. The filtrate was evaporated under reduced pressure. The residue was triturated in ether to give 1-(pyridin-2-ylmethyl)-1H-indazol-5-amine as an off-white solid (28.6 g, 95%); NMR Spectrum (CDCl$_3$) 3.61 (m, 2H), 5.67 (m, 2H), 6.78 (d, 1H), 6.82 (dd, 1H), 6.95 (d, 1H), 7.16 (m, 1H), 7.20 (d, 1H), 7.53 (m, 1H), 7.87 (s, 1H), 8.57 (d, 1H); Mass spectrum MH$^+$ 225.

EXAMPLE 4

(2S)—N,N-Dimethyl-2-[(4-{[1-(pyridin-2-ylmethyl)-1H-indazol-5-yl]amino}quinazolin-5-yl)oxy]propanamide A mixture of (2S)—N,N-dimethyl-2-[(4-oxo-3,4-dihydroquinazolin-5-yl)oxy]propanamide (200 mg, 0.77 mmol), triphenylphosphine (603 mg, 2.3 mmol) and carbon tetrachloride (2.2 ml, 23 mmol) in 1,2-dichloroethane (5 ml) was stirred at 45° C. for 2 hours. 1-(Pyridin-2-ylmethyl)-1H-indazol-5-amine (179 mg, 0.8 mmol) was added and the solvent was evaporated under vacuum. Acetonitrile (5 ml) was added. The mixture was stirred at 75° C. for 2 hours. After cooling, 6N methanolic ammonia (3 ml) was added. The solvents were evaporated under vacuum. The residue was purified by chromatography on silica gel (eluant: 3% to 5% methanol in DCM) to give the title compound as a white foam (208 mg, 58%); NMR Spectrum (CDCl$_3$) 1.72 (d, 3H), 3.06 (s, 3H), 3.14 (s, 3H), 5.43 (q, 1H), 5.75 (s, 2H), 6.81 (m, 2H), 7.17 (m, 1H), 7.41 (d, 1H), 7.48 (d, 1H), 7.62-7.53 (m, 2H), 7.81 (dd, 1H), 8.10 (s, 1H), 8.44 (d, 1H), 8.58 (d, 1H), 8.62 (s, 1H); Mass spectrum 468.

The (2S)—N,N-dimethyl-2-[(4-oxo-3,4-dihydroquinazolin-5-yl)oxy]propanamide used as starting material was made from (5-hydroxy-4-oxoquinazolin-3(4H)-yl)methyl pivalate and (R)—N,N-dimethyl lactamide (5.1 g, 43.5 mmol; made from (R)-methyl lactate according to Larcheveque M., Synthesis 1986, 1, 60) using an analogous procedure to Example 3, starting material. The (2S)—N,N-dimethyl-2-[(4-oxo-3,4-dihydroquinazolin-5-yl)oxy]propanamide provided was a white solid (5 g, 66%); NMR Spectrum 1.49 (d, 3H), 2.82 (s, 3H), 3.07 (s, 3H), 5.21 (q, 1H), 6.74 (d, 1H), 7.17 (d, 1H), 7.62 (t, 1H), 7.96 (s, 1H); Mass spectrum MH+ 262.

EXAMPLE 5

(2R)-2-[(4-{[1-(pyridin-2-ylmethyl)-1H-indazol-5-yl]amino}quinazolin-5-yl)oxy]propanamide A solution of methyl (2R)-2-[(4-{[1-(pyridin-2-ylmethyl)-1H-indazol-5-yl]amino}quinazolin-5-yl)oxy]propanoate (250 mg, 0.55 mmol) in methanol (3 ml) was saturated with ammonia by bubbling gaseous ammonia into the solution for a few minutes. The tube containing the solution was sealed and the mixture was stirred for 48 hours at room temperature. The precipitate was filtered, washed with ether and dried to give the title compound as a white solid (165 mg, 65%); NMR Spectrum 1.66 (d, 3H), 5.14 (q, 1H), 5.77 (s, 2H), 6.94 (d, 1H), 7.02 (d, 1H), 7.30 (m, 1H), 7.36 (d, 1H), 7.55 (br s, 1H), 7.78-7.67 (m, 4H), 7.89 (br s, 1H), 8.15 (s, 1H), 8.52 (m, 3H), 10.80 (br s, 1H); Mass spectrum MH+ 440.

The methyl (2R)-2-[(4-{[1-(pyridin-2-ylmethyl)-1H-indazol-5-yl]amino}quinazolin-5-yl)oxy]propanoate used as starting material was made as follows.

4N Hydrogen chloride in dioxane (9.6 ml, 38.4 mmol) was added to a mixture of 1-(pyridin-2-ylmethyl)-1H-indazol-5-amine (8.78 g, 39.2 mmol) and 4-chloro-5-fluoroquinazoline (7 g, 38.4 mmol; prepared as described in WO 2001/094341) in acetonitrile (100 ml). The mixture was stirred at 75° C. for 1.5 hours. After cooling, the mixture was evaporated to dryness. The residue was diluted in 6N methanolic ammonia. The mixture was evaporated to dryness and was diluted in DCM. After filtration of the solids, the filtrate was evaporated to dryness. The residue was purified by chromatography on silica gel (eluant: methanol in DCM) to give 5-fluoro-N-[1-(pyridin-2-ylmethyl)-1H-indazol-5-yl]quinazolin-4-amine as a beige solid (10.2 g, 72%); NMR spectrum (CDCl$_3$) 5.76 (s, 2H), 6.89 (d, 1H), 7.22-7.18 (m, 2H), 7.58-7.45 (m, 3H), 7.72 (m, 2H), 8.11 (s, 1H), 8.21 (s, 1H), 8.47 (m, 1H), 8.60 (d, 1H), 8.68 (s, 1H); Mass spectrum MH+ 371.

A mixture of 5-fluoro-N-[1-(pyridin-2-ylmethyl)-1H-indazol-5-yl]quinazolin-4-amine (10.2 g, 27.5 mmol) and sodium methoxide (4.46 g, 82.6 mmol) in methanol (250 ml) was heated at reflux for 24 hours. After cooling and evaporation of the solvents, the residue was dissolved in DCM. This solution was washed with water and brine and dried over MgSO$_4$. Evaporation of the solvents gave 5-methoxy-N-[1-(pyridin-2-ylmethyl)-1H-indazol-5-yl]quinazolin-4-amine as a beige solid (10.5 g, 100%); NMR spectrum (CDCl$_3$) 4.11 (s, 3H), 5.75 (s, 2H), 6.87 (d, 1H), 6.91 (d, 1H), 7.19 (m, 1H), 7.57-7.42 (m, 4H), 7.64 (t, 1H), 8.09 (s, 1H), 8.22 (m, 1H), 8.59 (m, 2H), 9.83 (br s, 1H); Mass spectrum MH+ 383.

A mixture of 5-methoxy-N-[1-(pyridin-2-ylmethyl)-1H-indazol-5-yl]quinazolin-4-amine (10.1 g, 27.4 mmol) and pyridine hydrochloride (15.8 g, 137 mmol) in pyridine (150 ml) was heated at reflux for 3 hours. After cooling and evaporation of the solvents, the residue was triturated in 5% aqueous sodium bicarbonate and the resulting mixture was stirred for 30 minutes. The yellowish precipitate was filtered, washed with water and ether, and dried over P$_2$O$_5$ under high vacuum to give 4-{[1-(pyridin-2-ylmethyl)-1H-indazol-5-yl]amino}quinazolin-5-ol as a solid (10.1 g, 100%); NMR spectrum 5.76 (s, 2H), 6.67 (m, 2H), 6.96 (d, 1H), 7.29 (m, 1H), 7.42 (m, 1H), 7.52 (dd, 1H), 7.74-7.66 (m, 2H), 8.13 (s, 1H), 8.33 (s, 2H), 8.52 (d, 1H); Mass spectrum MH+ 369.

DTAD (11.48 g, 49.9 mmol) was added portion-wise to an ice-cooled solution of 4-{[1-(pyridin-2-ylmethyl)-1H-indazol-5-yl]amino}quinazolin-5-ol (7.36 g, 20 mmol), (S)-methyl lactate (2.29 ml, 24 mmol) and triphenylphosphine (13.1 g, 49.9 mmol) in DCM (200 ml). The mixture was stirred at room temperature for 1 hour. The mixture was extracted with 2N hydrochloric acid (2×50 ml). The hydrochloric layers were combined and washed with DCM. The pH of the solution was adjusted to pH 9 by slow addition of concentrated aqueous ammonia while cooling. This aqueous solution was extracted with DCM (2×100 ml). These DCM layers were combined, washed with water and brine and dried over MgSO$_4$. After evaporation of the solvents, the residue was purified by chromatography on silica gel (eluant: 4% methanol in DCM) to give methyl (2R)-2-[(4-{[1-(pyridin-2-ylmethyl)-1H-indazol-5-yl]amino}quinazolin-5-yl)oxy]propanoate as a yellowish solid (7.35 g, 80%); NMR Spectrum (CDCl$_3$) 1.80 (d, 3H), 3.85 (s, 3H), 5.15 (q, 1H), 5.76 (s, 2H), 6.79 (d, 1H), 6.85 (d, 1H), 7.18 (m, 1H), 7.43 (d, 1H), 7.50 (d, 1H), 7.63-7.54 (m, 2H), 7.70 (dd, 1H), 8.11 (s, 1H), 8.38 (s, 1H), 8.59 (br d, 1H), 8.63 (s, 1H); Mass spectrum MH+ 455.

EXAMPLE 6

(2R)—N-methyl-2-[(4-{[1-(pyridin-2-ylmethyl)-1H-indazol-5-yl]amino}quinazolin-5-yl)oxy]propanamide Using the same procedure as in Example 5, methyl (2R)-2-[(4-{[1-(pyridin-2-ylmethyl)-1H-indazol-5-yl]amino}quinazolin-5-yl)oxy]propanoate (250 mg, 0.55 mmol) was reacted with methylamine to give the title compound as a beige solid (213 mg, 86%); NMR Spectrum 1.65 (d, 3H), 2.67 (d, 3H), 5.16 (q, 1H), 5.77 (s, 2H), 6.96 (d, 1H), 7.00 (d, 1H), 7.29 (m, 1H), 7.36 (d, 1H), 7.72 (m, 4H), 8.17 (s, 1H), 8.38 (m, 1H), 8.53 (m, 3H), 10.68 (br s, 1H); Mass spectrum MH+ 454.

EXAMPLE 7

(2R)—N-ethyl-2-[(4-{[1-(pyridin-2-ylmethyl)-1H-indazol-5-yl]amino}quinazolin-5-yl)oxy]propanamide Using the same procedure as in Example 5, methyl (2R)-2-[(4-{[1-(pyridin-2-ylmethyl)-1H-indazol-5-yl]amino}quinazolin-5-yl)oxy]propanoate (250 mg, 0.55 mmol) was reacted with ethylamine to give the title compound as a beige solid (160 mg, 62%), except that the crude material was purified on an HPLC column (C18, 5 microns, 19 mm diameter, 100 mm length) of a preparative HPLC-MS system eluting with a mixture of water and acetonitrile containing 2 g/l of ammonium carbonate (gradient). NMR Spectrum 1.04 (t, 3H), 1.65 (d, 3H), 3.17 (m, 2H), 5.15 (q, 1H), 5.77 (s, 2H), 6.95 (d, 1H), 7.01 (d, 1H), 7.29 (m, 1H), 7.36 (d, 1H), 7.72 (m, 4H), 8.17 (s, 1H), 8.44 (br t, 1H), 8.53 (m, 3H), 10.70 (br s, 1H); Mass spectrum MH+ 468.

EXAMPLE 8

5-[(1R)-1-methyl-2-oxo-2-pyrrolidin-1-ylethoxy]-N-[1-(pyridin-2-ylmethyl)-1H-indazol-5-yl]quinazolin-4-amine Using the same procedure as in Example 5, methyl (2R)-2-[(4-{[1-(pyridin-2-ylmethyl)-1H-indazol-5-yl]amino}quinazolin-5-yl)oxy]propanoate (200 mg, 0.44 mmol) was reacted with pyrrolidine (0.22 ml, 2.6 mmol) to give the title compound as a beige solid (152 mg, 70%), except that 3 Å molecular sieve was added and that the crude material was purified on an HPLC column (C18, 5 microns, 19 mm diameter, 100 mm length) of a preparative HPLC-MS system eluting with a mixture of water and acetonitrile containing 2 g/l of ammonium carbonate (gradient). NMR Spectrum 1.60 (d, 3H), 1.81 (m, 2H), 1.94 (m, 2H), 3.47-3.30 (m, 3H), 3.77 (m, 1H), 5.62 (q, 1H), 5.77 (s, 2H), 6.95 (d, 1H), 7.28 (m, 2H), 7.35 (d, 1H), 7.74-7.68 (m, 3H), 7.82 (dd, 1H), 8.15 (s, 1H), 8.53 (m, 3H), 11.07 (br s, 1H); Mass spectrum MH$^+$ 494.

EXAMPLE 9

(2R)—N-(2-hydroxyethyl)-2-[(4-{[1-(pyridin-2-ylmethyl)-1H-indazol-5-yl]amino}quinazolin-5-yl)oxy]propanamide Using the same procedure as in Example 5, methyl (2R)-2-[(4-{[1-(pyridin-2-ylmethyl)-1H-indazol-5-yl]amino}quinazolin-5-yl)oxy]propanoate (250 mg, 0.55 mmol) was reacted with ethanolamine (0.332 ml, 5.5 mmol) to give the title compound as a white solid (164 mg, 62%); NMR Spectrum 1.64 (d, 3H), 3.21 (m, 2H), 3.43 (m, 2H), 4.75 (t, 1H), 5.22 (q, 1H), 5.77 (s, 2H), 6.95 (d, 1H), 7.01 (d, 1H), 7.29 (m, 1H), 7.36 (d, 1H), 7.72 (m, 4H), 8.16 (s, 1H), 8.48 (br t, 1H), 8.53 (m, 3H), 10.73 (br s, 1H); Mass spectrum MH$^+$ 484.

EXAMPLE 10

N,N-dimethyl-2-[(4-{[1-(pyridin-2-ylmethyl)-1H-indazol-5-yl]amino}quinazolin-5-yl)oxy]acetamide Using the same procedure as in Example 5, methyl [(4-{[1-(pyridin-2-ylmethyl)-1H-indazol-5-yl]amino}quinazolin-5-yl)oxy]acetate (250 mg, 0.55 mmol) was reacted with dimethylamine to give the title compound as a white solid (183 mg, 73%); NMR Spectrum 2.97 (s, 3H), 3.04 (s, 3H), 5.17 (s, 2H), 5.77 (s, 2H), 6.96 (d, 1H), 7.22 (d, 1H), 7.29 (m, 1H), 7.36 (d, 1H), 7.76-7.69 (m, 3H), 7.91 (m, 1H), 8.15 (s, 1H), 8.53 (m, 2H), 8.57 (s, 1H), 11.21 (br s, 1H); Mass spectrum MH$^+$ 454.

The methyl [(4-{[1-(pyridin-2-ylmethyl)-1H-indazol-5-yl]amino}quinazolin-5-yl)oxy]acetate used as starting material was made as follows:

DTAD (2.51 g, 10.9 mmol) was added portion-wise to a solution of 4-{[1-(pyridin-2-ylmethyl)-1H-indazol-5-yl]amino}quinazolin-5-ol (2 g, 5.43 mmol), methyl glycolate (0.629 ml, 8.15 mmol) and triphenylphosphine (2.86 g, 10.9 mmol) in DCM (50 ml). The mixture was stirred at room temperature for 2 hours. The solvents were evaporated under vacuum. The residue was triturated with ethyl acetate. The resulting precipitate was filtered, washed with ethyl acetate and dried under vacuum to give the title compound to give methyl [(4-{[1-(pyridin-2-ylmethyl)-1H-indazol-5-yl]amino}quinazolin-5-yl)oxy]acetate (1.4 g, 59%); NMR Spectrum 3.82 (s, 3H), 5.15 (s, 2H), 5.78 (s, 2H), 6.97 (d, 1H), 7.14 (d, 1H), 7.29 (m, 1H), 7.39 (d, 1H), 7.73 (m, 4H), 8.17 (s, 1H), 8.52 (m, 3H), 10.56 (br s, 1H); Mass spectrum MH$^+$ 441.

EXAMPLE 11

2-[(4-{[1-(pyridin-2-ylmethyl)-1H-indazol-5-yl]amino}quinazolin-5-yl)oxy]acetamide Using the same procedure as in Example 5, methyl [(4-{[1-(pyridin-2-ylmethyl)-1H-indazol-5-yl]amino}quinazolin-5-yl)oxy]acetate (250 mg, 0.55 mmol) was reacted with ammonia to give the title compound as a white solid (210 mg, 90%); NMR Spectrum 4.87 (s, 2H), 5.77 (s, 2H), 6.97 (m, 2H), 7.29 (m, 1H), 7.37 (d, 1H), 7.59 (br s, 1H), 7.76-7.66 (m, 3H), 7.84 (br s, 1H), 7.91 (m, 1H), 8.14 (s, 1H), 8.57-8.52 (m, 3H), 10.98 (br s, 1H); Mass spectrum MH$^+$ 426.

EXAMPLE 12

N-ethyl-2-[(4-{[1-(pyridin-2-ylmethyl)-1H-indazol-5-yl]amino}quinazolin-5-yl)oxy]acetamide Using the same procedure as in Example 5, methyl [(4-{[1-(pyridin-2-ylmethyl)-1H-indazol-5-yl]amino}quinazolin-5-yl)oxy]acetate (250 mg, 0.55 mmol) was reacted with ethylamine to give the title compound as a beige solid (140 mg, 56%); NMR Spectrum 1.09 (t, 3H), 3.23 (m, 2H), 4.87 (s, 2H), 5.77 (s, 2H), 6.97 (m, 2H), 7.29 (m, 1H), 7.37 (d, 1H), 7.76-7.69 (m, 3H), 7.83 (m, 1H), 8.16 (s, 1H), 8.38 (br t, 1H), 8.56-8.53 (m, 3H), 10.85 (br s, 1H); Mass spectrum MH$^+$ 454.

EXAMPLE 13

N-(2-hydroxyethyl)-2-[(4-{[1-(pyridin-2-ylmethyl)-1H-indazol-5-yl]amino}quinazolin-5-yl)oxy]acetamide Using the same procedure as in Example 5, methyl [(4-{[1-(pyridin-2-ylmethyl)-1H-indazol-5-yl]amino}quinazolin-5-yl)oxy]acetate (250 mg, 0.55 mmol) was reacted with ethanolamine (0.333 ml, 5.5 mmol) to give the title compound as a white solid (220 mg, 85%), except that the reaction was run at 45° C. for 2 days. NMR Spectrum 3.30 (m, 2H), 3.49 (m, 2H), 4.79 (m, 1H), 4.89 (s, 2H), 5.77 (s, 2H), 6.96 (m, 2H), 7.29 (m, 1H), 7.37 (d, 1H), 7.77-7.69 (m, 3H), 7.84 (m, 1H), 8.16 (s, 1H), 8.42 (br t, 1H), 8.57-8.53 (m, 3H), 10.87 (br s, 1H); Mass spectrum MH$^+$ 470.

EXAMPLE 14

N-methyl-2-[(4-{[1-(pyridin-2-ylmethyl)-1H-indazol-5-yl]amino}quinazolin-5-yl)oxy]acetamide Using the same procedure as in Example 5, methyl [(4-{[1-(pyridin-2-ylmethyl)-1H-indazol-5-yl]amino}quinazolin-5-yl)oxy]acetate (250 mg, 0.55 mmol) was reacted with methylamine to give the title compound as a white solid (185 mg, 76%), except that the residue was purified by chromatography on silica gel (eluant: 5% to 6% methanol in DCM). NMR Spectrum 2.73 (d, 3H), 4.88 (s, 2H), 5.77 (s, 2H), 6.97 (m, 2H), 7.29 (m, 1H), 7.37 (d, 1H), 7.76-7.69 (m, 3H), 7.84 (m, 1H), 8.16 (s, 1H), 8.32 (m, 1H), 8.54 (m, 3H), 10.84 (br s, 1H); Mass spectrum MH$^+$ 440.

EXAMPLE 15

N-(2-hydroxyethyl)-N-methyl-2-[(4-{[1-(pyridin-2-ylmethyl)-1H-indazol-5-yl]amino}quinazolin-5-yl)oxy]acetamide Using the same procedure as in Example 5, methyl [(4-{[1-(pyridin-2-ylmethyl)-1H-indazol-5-yl]amino}quinazolin-5-yl)oxy]acetate (200 mg, 0.45 mmol) was reacted with 2-(methylamino)ethanol (0.219 ml, 2.73 mmol) to give the title compound as a white solid (130 mg, 59%), except that the reaction was run at 45° C. for 18 hours. NMR Spectrum (2 rotamers, ratio 2/1) 2.97 and 3.08 (s, 3H), 3.62-3.43 (m, 4H), 4.73 and 4.99 (t, 1H), 5.16 and 5.23 (s, 2H), 5.77 (s, 2H), 6.96 (d, 1H), 7.37-7.18 (m, 3H), 7.75-7.69 (m, 3H), 7.90 (m, 1H), 8.15 (s, 1H), 8.53 (m, 2H), 8.57 (s, 1H), 11.20 and 11.21 (br s, 1H); Mass spectrum MH$^+$ 484.

EXAMPLE 16

5-(2-oxo-2-pyrrolidin-1-ylethoxy)-N-[1-(pyridin-2-ylmethyl)-1H-indazol-5-yl]quinazolin-4-amine Using the same procedure as in Example 5, methyl [(4-{[1-(pyridin-2-ylmethyl)-1H-indazol-5-yl]amino}quinazolin-5-yl)oxy]acetate (180 mg, 0.41 mmol) was reacted with pyrrolidine (0.205 ml, 2.45 mmol) to give the title compound as a light brown solid (160 mg, 82%), except that the reaction was run at 45° C. for 18 hours in the presence of 3 Å molecular sieve. NMR Spectrum 1.83 (m, 2H), 1.95 (m, 2H), 3.45 (t, 2H), 3.50 (t, 2H), 5.09 (s, 2H), 5.77 (s, 2H), 6.96 (d, 1H), 7.18 (d, 1H), 7.29 (m, 1H), 7.37 (d, 1H), 7.77-7.69 (m, 3H), 7.91 (m, 1H), 8.15 (s, 1H), 8.53 (s, 2H), 8.57 (s, 1H), 11.16 (br s, 1H); Mass spectrum MH$^+$ 480.

EXAMPLE 17

5-(2-morpholin-4-yl-2-oxoethoxy)-N-[1-(pyridin-2-ylmethyl)-1H-indazol-5-yl]quinazolin-4-amine Using the same procedure as in Example 5, methyl [(4-{[1-(pyridin-2-ylmethyl)-1H-indazol-5-yl]amino}quinazolin-5-yl)oxy]acetate (180 mg, 0.40 mmol) was reacted with morpholine (0.346 ml, 3.96 mmol) to give the title compound as a solid (115 mg, 59%), except that the reaction was run at 60° C. for 32 hours in the presence of 3 Å molecular sieve. NMR Spectrum 3.68-3.52 (m, 8H), 5.20 (s, 2H), 5.77 (s, 2H), 6.96 (d, 1H), 7.23 (d, 1H), 7.30 (m, 1H), 7.37 (d, 1H), 7.77-7.68 (m, 3H), 7.90 (m, 1H), 8.15 (s, 1H), 8.53 (s, 2H), 8.56 (s, 1H), 11.18 (br s, 1H); Mass spectrum MH$^+$ 496.

EXAMPLE 18

(2R)—N,N-dimethyl-2-[(4-{[1-(1,3-thiazol-4-ylmethyl)-1H-indazol-5-yl]amino}quinazolin-5-yl)oxy]propanamide A mixture of (2R)—N,N-dimethyl-2-[(4-oxo-3,4-dihydroquinazolin-5-yl)oxy]propanamide (200 mg, 0.77 mmol), triphenylphosphine (603 mg, 2.3 mmol) and carbon tetrachloride (2.2 ml, 23 mmol) in 1,2-dichloroethane (5 ml) was stirred at 45° C. for 2 hours. 1-(1,3-Thiazol-4-ylmethyl)-1H-indazol-5-amine (184 mg, 0.8 mmol) was added and the solvents were evaporated under vacuum. Acetonitrile (5 ml) was added. The mixture was stirred at 75° C. for 2 hours. After cooling, the solvents were evaporated under vacuum. The residue was diluted in 6N methanolic ammonia and the solvents were evaporated under vacuum. The residue was purified by chromatography on silica gel (eluant: 3% to 5% methanol in DCM) to give the title compound as a beige foam (215 mg, 60%); NMR Spectrum (CDCl$_3$) 1.73 (d, 3H), 3.06 (s, 3H), 3.14 (s, 3H), 5.43 (q, 1H), 5.80 (s, 2H), 6.81 (d, 1H), 6.93 (s, 1H), 7.48 (m, 2H), 7.60 (t, 1H), 7.84 (dd, 1H), 8.08 (s, 1H), 8.43 (s, 1H), 8.62 (s, 1H), 8.78 (s, 1H); Mass spectrum 474.

The 1-(1,3-thiazol-4-ylmethyl)-1H-indazol-5-amine used as starting material was made from 5-nitroindazole and 4-(chloromethyl)-1,3-thiazole hydrochloride according to the procedure described in Example 3, starting material:

5-Nitro-1-(1,3-thiazol-4-ylmethyl)-1H-indazole: Yield: 1.31 g, 55%; NMR Spectrum (CDCl$_3$) 5.82 (s, 2H), 7.16 (s, 1H), 7.63 (d, 1H), 8.27 (m, 2H), 8.73 (s, 1H), 8.79 (s, 1H).

1-(1,3-Thiazol-4-ylmethyl)-1H-indazol-5-amine: beige solid, 505 mg, 57%, except that the reaction was performed in ethanol; NMR Spectrum (CDCl$_3$) 5.72 (s, 2H), 6.95-6.85 (m, 3H), 7.29 (d, 1H), 7.85 (s, 1H), 8.77 (s, 1H); Mass spectrum MH$^+$ 231.

EXAMPLE 19

(2R)-2-[(4-{[1-(3-fluorobenzyl)-1H-indazol-5-yl]amino}quinazolin-5-yl)oxy]-N,N-dimethylpropanamide Using the same procedure as in Example 18, (2R)—N,N-dimethyl-2-[(4-oxo-3,4-dihydroquinazolin-5-yl)oxy]propanamide (200 mg, 0.77 mmol) and 1-(3-fluorobenzyl)-1H-indazol-5-amine (193 mg, 0.8 mmol) were reacted to give the title compound as a pale solid (272 mg, 74%); NMR Spectrum (CDCl$_3$) 1.72 (d, 3H), 3.06 (s, 3H), 3.14 (s, 3H), 5.43 (q, 1H), 5.59 (s, 2H), 6.81 (d, 1H), 6.87 (d, 1H), 6.96 (m, 2H), 7.25 (m, 1H), 7.34 (d, 1H), 7.47 (d, 1H), 7.60 (t, 1H), 7.84 (dd, 1H), 8.07 (s, 1H), 8.42 (s, 1H), 8.62 (s, 1H); Mass spectrum 485.

The 1-(3-fluorobenzyl)-1H-indazol-5-amine used as starting material was made from 5-nitroindazole and 3-fluorobenzyl bromide according to the procedure described in Example 3, starting material:

1-(3-Fluorobenzyl)-5-nitro-1H-indazole: 1.31 g, 55%, except that potassium iodide (1.05 equivalents) was added; NMR Spectrum (CDCl$_3$) 5.82 (s, 2H), 7.16 (s, 1H), 7.63 (d, 1H), 8.27 (m, 2H), 8.73 (s, 1H), 8.79 (s, 1H).

1-(3-Fluorobenzyl)-1H-indazol-5-amine: beige solid, 804 mg, 95%; NMR Spectrum (CDCl$_3$) 5.52 (s, 2H), 6.83 (m, 2H), 6.95 (m, 3H), 7.13 (d, 1H), 7.25 (m, 1H), 7.85 (s, 1H).

EXAMPLE 20

(2R)—N,N-dimethyl-2-[(4-{[1-(1,3-thiazol-2-ylmethyl)-1H-indazol-5-yl]amino}quinazolin-5-yl)oxy]propanamide Using the same procedure as in Example 18, (2R)—N,N-dimethyl-2-[(4-oxo-3,4-dihydroquinazolin-5-yl)oxy]propanamide (150 mg, 0.57 mmol) and 1-(1,3-thiazol-2-ylmethyl)-1H-indazol-5-amine (138 mg, 0.6 mmol) were reacted to give the title compound as a white solid (208 mg, 77%); NMR Spectrum (CDCl$_3$) 1.73 (d, 3H), 3.06 (s, 3H), 3.14 (s, 3H), 5.43 (q, 1H), 5.92 (s, 2H), 6.82 (d, 1H), 7.26 (m, 1H), 7.50 (d, 2H), 7.61 (t, 1H), 7.75 (d, 1H), 7.87 (dd, 1H), 8.11 (s, 1H), 8.45 (s, 1H), 8.62 (s, 1H); Mass spectrum 474.

The 1-(1,3-thiazol-2-ylmethyl)-1H-indazol-5-amine used as starting material was made from 5-nitroindazole and 2-(chloromethyl)-1,3-thiazole (prepared as described in Dondoni A. et al, Tetrahedron, 1988, 44, 2021) according to the procedure described in Example 3, starting material 5-Nitro-1-(1,3-thiazol-2-ylmethyl)-1H-indazole: Yield: 724 mg, 65%; NMR Spectrum (CDCl$_3$) 5.96 (s, 2H), 7.32 (d, 1H), 7.62 (d, 1H), 7.77 (d, 2H), 8.28 (m, 2H), 8.74 (s, 1H).

1-(1,3-Thiazol-2-ylmethyl)-1H-indazol-5-amine: pale solid, 578 mg, 90%; NMR Spectrum (CDCl$_3$) 3.48 (m, 2H), 5.84 (s, 2H), 6.86 (dd, 1H), 6.94 (s, 1H), 7.29-7.23 (m, 2H), 7.73 (s, 1H), 7.88 (s, 1H).

EXAMPLE 21

(2R)—N,N-dimethyl-2-{[4-({1-[(2-methyl-1,3-thiazol-5-yl)methyl]-1H-indazol-5-yl}amino)quinazolin-5-yl]oxy}propanamide Using the same procedure as in Example 18, (2R)—N,N-dimethyl-2-[(4-oxo-3,4-dihydroquinazolin-5-yl)oxy]propanamide (261 mg, 1 mmol) and 1-[(2-methyl-1,3-thiazol-5-yl)methyl]-1H-indazol-5-amine (269 mg, 1.1 mmol) were reacted to give the title compound as a white solid (300 mg, 61%); NMR Spectrum (CDCl$_3$) 1.73 (d, 3H), 2.62 (s, 3H), 3.07 (s, 3H), 3.15 (s, 3H), 5.43 (q, 1H), 5.71 (s, 2H), 6.82 (d, 1H), 7.43 (d, 1H), 7.49 (d, 1H), 7.61 (m, 2H), 7.86 (dd, 1H), 8.05 (s, 1H), 8.42 (s, 1H), 8.62 (s, 1H); Mass spectrum 488.

The 1-[(2-methyl-1,3-thiazol-5-yl)methyl]-1H-indazol-5-amine used as starting material was made from 5-nitroindazole and 5-(chloromethyl)-2-methyl-1,3-thiazole (prepared as described in Mashraqi S. H. et al, J. Am. Chem. Soc., 1982, 104, 4461) according to the procedure described in Example 3, starting material:

1-[(2-Methyl-1,3-thiazol-5-yl)methyl]-5-nitro-1H-indazole: Yield: 1.5 g, 59%; NMR Spectrum (CDCl$_3$) 2.64 (s, 3H), 5.76 (s, 2H), 7.50 (d, 1H), 7.62 (d, 1H), 8.25 (s, 1H), 8.29 (dd, 1H), 8.74 (s, 1H).

1-[(2-Methyl-1,3-thiazol-5-yl)methyl]-1H-indazol-5-amine: pale solid, 1.2 g, 93%; NMR Spectrum (CDCl$_3$) 2.61 (s, 3H), 3.62 (m, 2H), 5.63 (s, 2H), 6.86 (dd, 1H), 6.93 (s, 1H), 7.23 (d, 1H), 7.54 (s, 1H), 7.82 (s, 1H).

EXAMPLE 22

(2R)-2-{[4-({1-[(6-fluoropyridin-3-yl)methyl]-1H-indazol-5-yl}amino)quinazolin-5-yl]oxy}-N,N-dimethylpropanamide Using the same procedure as in Example 18, (2R)—N,N-dimethyl-2-[(4-oxo-3,4-dihydroquinazolin-5-yl)oxy]propanamide (200 mg, 0.77 mmol) and 1-[(6-fluoropyridin-3-yl)methyl]-1H-indazol-5-amine (204 mg, 0.84 mmol) were reacted to give the title compound as a white solid (225 mg, 60%); NMR Spectrum (CDCl$_3$) 1.73 (d, 3H), 3.07 (s, 3H), 3.15 (s, 3H), 5.44 (q, 1H), 5.59 (s, 2H), 6.84 (m, 2H), 7.37 (d, 1H), 7.8-7.45 (m, 3H), 7.87 (dd, 1H), 8.07 (s, 1H), 8.21 (s, 1H), 8.44 (s, 1H), 8.62 (s, 1H); Mass spectrum 486.

The 1-[(6-fluoropyridin-3-yl)methyl]-1H-indazol-5-amine used as starting material was made from 5-nitroindazole and 5-(chloromethyl)-2-fluoropyridine (Pesti J. A. et al, J. Org. Chem., 2000, 65, 7718) according to the procedure described in Example 3, starting material:

1-[(6-Fluoropyridin-3-yl)methyl]-5-nitro-1H-indazole: Yield: 672 mg, 54%; NMR Spectrum (CDCl$_3$) 5.64 (s, 2H), 6.90 (dd, 1H), 7.45 (d, 1H), 7.67 (m, 1H), 8.22 (s, 1H), 8.28 (m, 2H), 8.76 (s, 1H).

1-[(6-Fluoropyridin-3-yl)methyl]-1H-indazol-5-amine: pale solid, 490 mg, 93%; NMR Spectrum (CDCl$_3$) 3.63 (m, 2H), 5.51 (s, 2H), 6.83 (m, 2H), 6.94 (s, 1H), 7.15 (d, 1H), 7.57 (m, 1H), 7.84 (s, 1H), 8.15 (s, 1H).

EXAMPLE 23

(2R)-2-[(4-{[1-(3-methoxybenzyl)-1H-indazol-5-yl]amino}quinazolin-5-yl)oxy]-N,N-dimethylpropanamide Using the same procedure as in Example 18, (2R)—N,N-dimethyl-2-[(4-oxo-3,4-dihydroquinazolin-5-yl)oxy]propanamide (220 mg, 0.84 mmol) and 1-(3-methoxybenzyl)-1H-indazol-5-amine (1.1 equivalents) were reacted to give the title compound as a beige foam (242 mg, 58%); NMR spectrum (CDCl$_3$) 1.72 (d, 3H), 3.05 (s, 3H), 3.14 (s, 3H), 3.73 (s, 3H), 5.42 (q, 1H), 5.57 (s, 2H), 6.74 (s, 1H), 6.78-6.81 (m, 3H), 7.20 (t, 1H), 7.36 (d, 1H), 7.46 (d, 1H), 7.59 (t, 1H), 7.80 (d, 1H), 8.06 (s, 1H), 8.40 (s, 1H), 8.61 (s, 1H), 10.85 (br s, 1H); Mass spectrum MH$^+$ 497.

The 1-(3-methoxybenzyl)-1H-indazol-5-amine used as starting material was made from 5-nitroindazole and 3-methoxybenzyl chloride according to the procedure described in Example 3, starting material:

1-(3-methoxybenzyl)-5-nitro-1H-indazole: Yield: 2.22 g, 43%; NMR spectrum (CDCl$_3$) 3.74 (s, 3H), 5.61 (s, 2H), 6.73 (s, 1H), 6.78 (d, 1H), 6.83 (d, 1H), 7.23 (d, 1H), 7.39 (d, 1H), 8.22 (d, 1H), 8.25 (s, 1H), 8.73 (s, 1H); Mass spectrum MH$^+$ 284.

1-(3-methoxybenzyl)-1H-indazol-5-amine: Yield: 364 mg, 94%; NMR spectrum (CDCl$_3$) 3.72 (s, 3H), 5.50 (s, 2H), 6.70 (s, 1H), 6.76-6.82 (m, 3H), 6.93 (s, 1H), 7.15 (d, 1H), 7.19 (t, 1H), 7.83 (s, 1H); Mass spectrum MH$^+$ 254.

EXAMPLE 24

(2R)-2-[(4-{[1-(2-cyanobenzyl)-1H-indazol-5-yl]amino}quinazolin-5-yl)oxy]-N,N-dimethylpropanamide Using the same procedure as in Example 18, (2R)—N,N-dimethyl-2-[(4-oxo-3,4-dihydroquinazolin-5-yl)oxy]propanamide (220 mg, 0.84 mmol) and 2-[(5-amino-1H-indazol-1-yl)methyl]benzonitrile (1.1 equivalents) were reacted to give the title compound as a beige foam (334 mg, 81%); NMR spectrum (CDCl$_3$) 1.72 (d, 3H), 3.06 (s, 3H), 3.14 (s, 3H), 5.43 (q, 1H), 5.83 (s, 2H), 6.81 (d, 1H), 7.01 (d, 1H), 7.37 (t, 1H), 7.42-7.47 (m, 3H), 7.60 (t, 1H), 7.70 (d, 1H), 7.86 (d, 1H), 8.10 (s, 1H), 8.47 (s, 1H), 8.62 (s, 1H), 10.92 (br s, 1H); Mass spectrum MH$^+$ 492.

The 2-[(5-amino-1H-indazol-1-yl)methyl]benzonitrile used as starting material was made from 5-nitroindazole and 2-bromomethyl benzonitrile according to the procedure described in Example 3, starting material:

2-[(5-nitro-1H-indazol-1-yl)methyl]benzonitrile: Yield: 3.12 g, 61%; NMR spectrum (CDCl$_3$) 5.95 (s, 2H), 7.20 (d, 1H), 7.53 (t, 1H), 7.65 (t, 1H), 7.90 (d, 1H), 8.01 (d, 1H), 8.29 (d, 1H), 8.48 (s, 1H), 8.87 (s, 1H); Mass spectrum MH$^+$ 277.

2-[(5-amino-1H-indazol-1-yl)methyl]benzonitrile: Yield: 212 mg, 68%; NMR spectrum (CDCl$_3$) 5.74 (s, 2H), 6.86 (d, 1H), 6.95 (s, 1H), 7.01 (d, 1H), 7.23 (d, 1H), 7.35 (t, 1H), 7.44 (t, 1H), 7.68 (d, 1H), 7.87 (s, 1H); Mass spectrum MH$^+$ 249.

EXAMPLE 25

(2R)—N,N-dimethyl-2-[(4-{[1-(1,3-oxazol-2-ylmethyl)-1H-indazol-5-yl]amino}quinazolin-5-yl)oxy]propanamide Using the same procedure as in Example 18, (2R)—N,N-dimethyl-2-[(4-oxo-3,4-dihydroquinazolin-5-yl)oxy]propanamide (212 mg, 0.81 mmol) and 1-(1,3-oxazol-2-ylmethyl)-1H-indazol-5-amine (1 equivalents) were reacted to give the title compound as a beige foam (295 mg, 80%); NMR spectrum (CDCl$_3$) 1.73 (d, 3H), 3.06 (s, 3H), 3.14 (s, 3H), 5.43 (q, 1H), 5.71 (s, 2H), 6.81 (d, 1H), 7.09 (s, 1H), 7.48-7.53 (m, 2H), 7.58-7.62 (m, 2H), 7.88 (d, 1H), 8.07 (s, 1H), 8.41 (s, 1H), 8.61 (s, 1H), 10.92 (br s, 1H); Mass spectrum MH$^+$ 458.

The 1-(1,3-oxazol-2-ylmethyl)-1H-indazol-5-amine used as starting material was made as follows:

n-BuLi (66.8 mL, 2.5 N in hexane, 167 mmol) was added drop-wise to oxazole (10.5 g, 152 mmol) in solution in THF (200 mL) at −70° C. After 2 hours at room temperature, the mixture was cooled to −60° C. and DMF (12.8 mL, 167 mmol) was added drop-wise. After one night at room temperature, the mixture was hydrolyzed with cold 1N hydrochloric acid and extracted with dichloromethane. The residue was purified on silica gel (5 to 10% Et$_2$O/CH$_2$Cl$_2$) to give a yellow oil (4.57 g) which was dissolved in methanol (100 mL). To this solution at 0° C. was added NaBH$_4$ (3.16 g, 83 mmol) portion-wise and the mixture was stirred at room temperature overnight. Brine was added and the pH adjusted to 7 with HCl 6N. After filtration and extraction with EtOAc, the organic layer was evaporated and the residue purified on silica gel (3 to 5% MeOH/CH$_2$Cl$_2$) to give 1,3-oxazol-2-ylmethanol as a colorless oil (2.95 g); NMR spectrum (CDCl$_3$) 4.75 (s, 2H), 7.10 (s, 1H), 7.64 (s, 1H).

1,3-oxazol-2-ylmethanol (2.68 g, 27 mmol) and triphenylphosphine (10.6 g, 40.6 mmol) were dissolved in CCl$_4$ (44 mL) and benzene (50 mL) and the mixture was refluxed for 6 hours, cooled down, filtered and evaporated. The residue was purified on silica gel (50% Et2O/petroleum ether) to give 2-(chloromethyl)-1,3-oxazole as a colorless oil (1.5 g); NMR spectrum (CDCl$_3$) 4.63 (s, 2H), 7.13 (s, 1H), 7.68 (s, 1H).

A mixture of 5-nitroindazole (500 mg, 3.07 mmol), potassium carbonate (889 mg, 6.44 mmol) and 2-(chloromethyl)-1,3-oxazole (396 mg, 3.37 mmol) in DMF (3 mL) was stirred for 3 hours at room temperature. Saturated NH$_4$Cl was added and the mixture was extracted with dichloromethane. After evaporation, the residue was purified on silica gel (30 to 35% EtOAc/petroleum ether) to give 5-nitro-1-(1,3-oxazol-2-ylmethyl)-1H-indazole (474 mg, 63%); NMR spectrum (CDCl$_3$) 5.76 (s, 2H), 7.11 (s, 1H), 7.60 (d, 1H), 7.62 (s, 1H) 8.26 (s, 1H), 8.31 (d, 1H), 8.74 (s, 1H).

Concentrated HCl (2.5 mL) was added to a solution of 5-nitro-1-(1,3-oxazol-2-ylmethyl)-1H-indazole (456 mg, 1.87 mmol) and SnCl$_2$ (1.42 g, 7.47 mmol) in ethanol (10 mL) and the mixture was heated at 50° C. for 4 hours. The mixture was cooled down, neutralized to pH 8 with 2N sodium hydroxide and extracted with ethyl acetate. The residue is purified on silica gel (EtOAc) to give 1-(1,3-oxazol-2-ylmethyl)-1H-indazol-5-amine (182 mg, 46%); NMR spectrum (CDCl$_3$) 5.55 (s, 2H), 6.79 (d, 1H), 6.86 (s, 1H), 7.00 (s, 1H), 7.24 (d, 1H), 7.50 (s, 1H), 7.77 (s, 1H); Mass spectrum MH$^+$ 215.

EXAMPLE 26

(2S)-2-[(4-{[1-(3-fluorobenzyl)-1H-indazol-5-yl]amino}quinazolin-5-yl)oxy]-N,N-dimethylpropanamide A solution of methyl (2S)-2-[(4-{[1-(3-fluorobenzyl)-1H-indazol-5-yl]amino}quinazolin-5-yl)oxy]propanoate (200 mg, 0.42 mmol) in 6N methanolic dimethylamine (10 ml) was stirred for 18 hours. After evaporation of the solvents, the residue was purified by chromatography on silica gel (eluant: 2% methanol in dichloromethane) to give the title compound as a beige solid (115 mg, 56%); NMR Spectrum 1.59 (d, 3H), 2.94 (s, 3H), 3.15 (s, 3H), 5.71 (s, 2H), 5.86 (q, 1H), 7.07 (m, 3H), 7.30 (d, 1H), 7.36 (m, 2H), 7.74 (m, 2H), 7.84 (m, 1H), 8.17 (s, 1H), 8.51 (s, 1H), 8.55 (s, 1H); Mass spectrum 485.

The methyl (2S)-2-[(4-{[1-(3-fluorobenzyl)-1H-indazol-5-yl]amino}quinazolin-5-yl)oxy]propanoate used as starting material was made as follows:

A mixture of 4-chloro-5-fluoroquinazoline (1.82 g, 10 mmol), 1-(3-fluorobenzyl)-1H-indazol-5-amine (2.41 g, 10 mmol, obtained as described in WO 98/02438) and diisopropylethylamine (1.74 ml, 10 mmol) in isopropanol (20 ml) was heated at 80° C. for 45 minutes. On cooling to ambient temperature, the product was filtered off and washed with isopropanol and ether. The precipitated solid was dried under high vacuum to give 5-fluoro-N-[1-(3-fluorobenzyl)-1H-indazol-5-yl]quinazolin-4-amine (3.2 g, 83%); NMR Spectrum (CDCl$_3$) 5.61 (s, 2H), 6.88 (d, 1H), 6.98 (m, 2H), 7.25 (m, 2H), 7.37 (d, 1H), 7.53 (dd, 1H), 7.73 (m, 2H), 8.09 (s, 1H), 8.19 (s, 1H), 8.49 (d, 1H), 8.69 (s, 1H); Mass spectrum MH$^+$ 388.

The 5-fluoro-N-[1-(3-fluorobenzyl)-1H-indazol-5-yl]quinazolin-4-amine (2.4 g, 6.48 mmol) was reacted as in Example 5 starting material, except that (R)-methyl lactate was used instead of (s)-methyl lactate, to give methyl (2S)-2-[(4-{[1-(3-fluorobenzyl)-1H-indazol-5-yl]amino}quinazolin-5-yl)oxy]propanoate:

N-[1-(3-fluorobenzyl)-1H-indazol-5-yl]-5-methoxy-quinazolin-4-amine: beige solid, Yield: 2.4 g, 97%; NMR Spectrum (CDCl$_3$) 4.11 (s, 3H), 5.59 (s, 2H), 7.00-6.85 (m, 4H), 7.27 (m, 1H), 7.34 (d, 1H), 7.48 (d, 1H), 7.53 (d, 1H), 7.65 (t, 1H), 8.06 (s, 1H), 8.19 (s, 1H), 8.61 (s, 1H), 9.82 (br s, 1H); Mass spectrum 400.

4-{[1-(3-fluorobenzyl)-1H-indazol-5-yl]amino}quinazolin-5-ol: solid, Yield: 2.8 g, 100%; Mass spectrum 386.

methyl (2S)-2-[(4-{[1-(3-fluorobenzyl)-1H-indazol-5-yl]amino}quinazolin-5-yl)oxy]propanoate: Yield: 875 mg, 60%; Mass spectrum 472.

EXAMPLE 27

N-[1-(3-fluorobenzyl)-1H-indazol-5-yl]-5-[(1S)-1-methyl-2-oxo-2-pyrrolidin-1-ylethoxy]-quinazolin-4-amine Using the same procedure as in Example 26, methyl (2S)-2-[(4-{[1-(3-fluorobenzyl)-1H-indazol-5-yl]amino}quinazolin-5-yl)oxy]propanoate (200 mg, 0.42 mmol) was reacted with pyrrolidine (0.35 ml, 4.2 mmol) to give the title compound as a solid (135 mg, 62%), except that the mixture was heated at 55° C. for 20 hours and purified by chromatography on silica gel (eluant: 3% methanol in DCM); NMR Spectrum 1.60 (d, 3H), 1.82 (m, 2H), 1.94 (m, 2H), 3.5-3.3 (m, 3H), 3.76 (m, 1H), 5.62 (q, 1H), 5.70 (s, 2H), 7.07

(m, 3H), 7.27 (d, 1H), 7.36 (m, 2H), 7.74 (m, 2H), 7.85 (m, 1H), 8.16 (s, 1H), 8.51 (s, 1H), 8.56 (s, 1H), 11.07 (br s, 1H); Mass spectrum 511.

EXAMPLE 28

(2S)-2-[(4-{[1-(3-fluorobenzyl)-1H-indazol-5-yl]amino}quinazolin-5-yl)oxy]propanamide Using the same procedure as in Example 5, methyl (2S)-2-[(4-{[1-(3-fluorobenzyl)-1H-indazol-5-yl]amino}quinazolin-5-yl)oxy]propanoate (200 mg, 0.42 mmol) was reacted with ammonia to give the title compound as a solid (150 mg, 77%); NMR Spectrum 1.66 (d, 3H), 5.14 (q, 1H), 5.70 (s, 2H), 7.12-7.01 (m, 4H), 7.36 (m, 2H), 7.54 (s, 1H), 7.75 (m, 3H), 7.89 (s, 1H), 8.16 (s, 1H), 8.52 (s, 2H), 10.80 (s, 1H); Mass spectrum 457.

EXAMPLE 29

N-[1-(3-fluorobenzyl)-1H-indazol-5-yl]-5-[(1R)-1-methyl-2-oxo-2-pyrrolidin-1-ylethoxy]-quinazolin-4-amine Using the same procedure as in Example 26, methyl (2R)-2-[(4-{[1-(3-fluorobenzyl)-1H-indazol-5-yl]amino}quinazolin-5-yl)oxy]propanoate (250 mg, 0.53 mmol) was reacted with pyrrolidine (0.44 ml, 5.3 mmol) to give the title compound as a white solid (210 mg, 77%), except that the mixture was heated at 55° C. for 20 hours and purified by chromatography on silica gel (eluant: 3% methanol in DCM); NMR Spectrum 1.60 (d, 3H), 1.82 (m, 2H), 1.94 (m, 2H), 3.5-3.3 (m, 3H), 3.76 (m, 1H), 5.62 (q, 1H), 5.70 (s, 2H), 7.07 (m, 3H), 7.27 (d, 1H), 7.36 (m, 2H), 7.74 (m, 2H), 7.85 (m, 1H), 8.16 (s, 1H), 8.51 (s, 1H), 8.56 (s, 1H), 11.08 (br s, 1H); Mass spectrum 511.

The methyl (2R)-2-[(4-{[1-(3-fluorobenzyl)-1H-indazol-5-yl]amino}quinazolin-5-yl)oxy]propanoate used as starting material was obtained as follows:

4-{[1-(3-fluorobenzyl)-1H-indazol-5-yl]amino}quinazolin-5-ol was reacted with (S)-methyl lactate as described in Example 5, starting material to give methyl (2R)-2-[(4-{[1-(3-fluorobenzyl)-1H-indazol-5-yl]amino}quinazolin-5-yl)oxy]propanoate (760 mg, 69%); Mass spectrum 472.

EXAMPLE 30

(2R)-2-[(4-{[1-(3-fluorobenzyl)-1H-indazol-5-yl]amino}quinazolin-5-yl)oxy]propanamide Using the same procedure as in Example 5, methyl (2R)-2-[(4-{[1-(3-fluorobenzyl)-1H-indazol-5-yl]amino}quinazolin-5-yl)oxy]propanoate (250 mg, 0.53 mmol) was reacted with ammonia to give the title compound as a pale solid (220 mg, 91%); NMR Spectrum 1.66 (d, 3H), 5.14 (q, 1H), 5.70 (s, 2H), 7.12-7.01 (m, 4H), 7.36 (m, 2H), 7.54 (s, 1H), 7.75 (m, 3H), 7.90 (s, 1H), 8.16 (s, 1H), 8.52 (s, 2H), 10.80 (s, 1H); Mass spectrum 457.

EXAMPLE 31

5-[(1S)-1-methyl-2-oxo-2-pyrrolidin-1-ylethoxy]-N-[1-(pyridin-2-ylmethyl)-1H-indazol-5-yl]quinazolin-4-amine Using the same procedure as in Example 26, methyl (2S)-2-[(4-{[1-(pyridin-2-ylmethyl)-1H-indazol-5-yl]amino}quinazolin-5-yl)oxy]propanoate (250 mg, 0.55 mmol) was reacted with pyrrolidine (0.46 ml, 5.5 mmol) to give the title compound as a beige solid (140 mg, 50%), except that the mixture was heated at 55° C. for 20 hours and purified by chromatography on silica gel (eluant: 4% methanol in DCM); NMR Spectrum 1.60 (d, 3H), 1.82 (m, 2H), 1.94 (m, 2H), 3.49-3.30 (m, 3H), 3.76 (m, 1H), 5.62 (q, 1H), 5.77 (s, 2H), 6.95 (d, 1H), 7.28 (m, 2H), 7.35 (d, 1H), 7.74-7.68 (m, 3H), 7.82 (dd, 1H), 8.15 (s, 1H), 8.53 (m, 3H), 11.08 (br s, 1H); Mass spectrum MH+ 494.

The methyl (2S)-2-[(4-{[1-(pyridin-2-ylmethyl)-1H-indazol-5-yl]amino}quinazolin-5-yl)oxy]propanoate used as starting material was made from 4-{[1-(pyridin-2-ylmethyl)-1H-indazol-5-yl]amino}quinazolin-5-ol (1.2 g, 3.3 mmol) and (R)-methyl lactate (0.37 ml, 3.9 mmol) using the same procedure as in Example 5 starting material:

Methyl (2S)-2-[(4-{[1-(pyridin-2-ylmethyl)-1H-indazol-5-yl]amino}quinazolin-5-yl)oxy]propanoate: white solid, Yield: 870 mg, 59%; NMR Spectrum (CDCl$_3$) 1.80 (d, 3H), 3.86 (s, 3H), 5.15 (q, 1H), 5.76 (s, 2H), 6.80 (d, 1H), 6.85 (d, 1H), 7.18 (m, 1H), 7.43 (d, 1H), 7.50 (d, 1H), 7.63-7.54 (m, 2H), 7.70 (dd, 1H), 8.11 (s, 1H), 8.38 (s, 1H), 8.59 (br d, 1H), 8.63 (s, 1H); Mass spectrum MH+ 455.

EXAMPLE 32

(2S)-2-[(4-{[1-(pyridin-2-ylmethyl)-1H-indazol-5-yl]amino}quinazolin-5-yl)oxy]propanamide Using the same procedure as in Example 5, methyl (2S)-2-[(4-{[1-(pyridin-2-ylmethyl)-1H-indazol-5-yl]amino}quinazolin-5-yl)oxy]propanoate (250 mg, 0.55 mmol) was reacted with ammonia to give the title compound as a pale solid (210 mg, 84%); NMR Spectrum 1.67 (d, 3H), 5.14 (q, 1H), 5.77 (s, 2H), 6.94 (d, 1H), 7.02 (d, 1H), 7.30 (m, 1H), 7.36 (d, 1H), 7.55 (br s, 1H), 7.76-7.67 (m, 4H), 7.90 (br s, 1H), 8.15 (s, 1H), 8.52 (m, 3H), 10.80 (br s, 1H); Mass spectrum MH+ 440.

EXAMPLE 33

5-[(1S)-1-methyl-2-oxo-2-pyrrolidin-1-ylethoxy]-N-[1-(1,3-thiazol-2-ylmethyl)-1H-indazol-5-yl]quinazolin-4-amine Using the same procedure as in Example 26, methyl (2S)-2-[(4-{[1-(1,3-thiazol-2-ylmethyl)-1H-indazol-5-yl]amino}quinazolin-5-yl)oxy]propanoate (250 mg, 0.54 mmol) was reacted with pyrrolidine (0.45 ml, 5.4 mmol) to give the title compound (189 mg, 70%) as a solid, except that the mixture was heated at 55° C. for 20 hours and purified by chromatography on silica gel (eluant: 1-5% methanol in DCM); NMR Spectrum 1.61 (d, 3H), 1.82 (m, 2H), 1.94 (m, 2H), 3.47-3.30 (m, 3H), 3.77 (m, 1H), 5.63 (q, 1H), 6.04 (s, 2H), 7.27 (d, 1H), 7.35 (d, 1H), 7.65 (d, 1H), 7.74 (m, 3H), 7.88 (dd, 1H), 8.20 (s, 1H), 8.52 (s, 1H), 8.56 (s, 1H), 11.09 (br s, 1H); Mass spectrum 500.

The methyl (2S)-2-[(4-{[1-(1,3-thiazol-2-ylmethyl)-1H-indazol-5-yl]amino}quinazolin-5-yl)oxy]propanoate used as starting material was made from 1-(1,3-thiazol-2-ylmethyl)-1H-indazol-5-amine, 4-chloro-5-fluoroquinazoline and (R)-methyl lactate using the procedure described in Example 26, starting material:

5-fluoro-N-[1-(1,3-thiazol-2-ylmethyl)-1H-indazol-5-yl]quinazolin-4-amine: beige solid, Yield: 3.6 g, 77%; NMR Spectrum (CDCl₃) 5.93 (s, 2H), 7.29-7.21 (m, 2H), 7.55 (m, 2H), 7.74 (m, 3H), 8.12 (s, 1H), 8.23 (s, 1H), 8.48 (br d, 1H), 8.69 (s, 1H); Mass spectrum 377.

5-methoxy-N-[1-(1,3-thiazol-2-ylmethyl)-1H-indazol-5-yl]quinazolin-4-amine: beige solid, Yield: 3.7 g, 100%; Mass spectrum 389.

4-{[1-(1,3-thiazol-2-ylmethyl)-1H-indazol-5-yl]amino}quinazolin-5-ol: solid, Yield: 3.4 g, 98%; NMR Spectrum (DMSOd₆ and CF₃CO₂D) 6.10 (s, 2H), 7.24 (m, 2H), 7.65 (m, 2H), 7.78 (m, 1H), 7.88 (m, 2H), 8.14 (m, 1H), 8.27 (s, 1H), 8.80 (m, 1H); Mass spectrum 375.

Methyl (2S)-2-[(4-{[1-(1,3-thiazol-2-ylmethyl)-1H-indazol-5-yl]amino}quinazolin-5-yl)oxy]propanoate: white solid, Yield: 1.6 g, 77%, using the (R)-methyl lactate; NMR Spectrum 1.72 (d, 3H), 3.80 (s, 3H), 5.54 (q, 1H), 6.05 (s, 2H), 7.18 (d, 1H), 7.38 (d, 1H), 7.80-7.66 (m, 5H), 8.21 (s, 1H), 8.48 (s, 1H), 8.54 (s, 1H), 10.53 (br s, 1H); Mass spectrum 461.

EXAMPLE 34

(2S)—N,N-dimethyl-2-[(4-{[1-(1,3-thiazol-2-ylmethyl)-1H-indazol-5-yl]amino}quinazolin-5-yl)oxy]propanamide Using the same procedure as in Example 26, methyl (2S)-2-[(4-{[1-(1,3-thiazol-2-ylmethyl)-1H-indazol-5-yl]amino}quinazolin-5-yl)oxy]propanoate (250 mg, 0.54 mmol) was reacted with dimethylamine to give the title compound as a white solid (195 mg, 76%); NMR Spectrum 1.59 (d, 3H), 2.93 (s, 3H), 3.14 (s, 3H), 5.85 (q, 1H), 6.04 (s, 2H), 7.30 (d, 1H), 7.35 (d, 1H), 7.65 (d, 1H), 7.74 (m, 3H), 7.87 (dd, 1H), 8.20 (s, 1H), 8.51 (s, 1H), 8.55 (s, 1H), 11.15 (br s, 1H); Mass spectrum 474.

EXAMPLE 35

(2S)-2-[(4-{[1-(1,3-thiazol-2-ylmethyl)-1H-indazol-5-yl]amino}quinazolin-5-yl)oxy]propanamide Using the same procedure as in Example 5, methyl (2S)-2-[(4-{[1-(1,3-thiazol-2-ylmethyl)-1H-indazol-5-yl]amino}quinazolin-5-yl)oxy]propanoate (250 mg, 0.54 mmol) was reacted with ammonia to give the title compound as a white solid (216 mg, 89%); NMR Spectrum 1.67 (d, 3H), 5.14 (q, 1H), 6.04 (s, 2H), 7.02 (d, 1H), 7.36 (d, 1H), 7.56 (br s, 1H), 7.66 (d, 1H), 7.83-7.72 (m, 4H), 7.90 (br s, 1H), 8.19 (s, 1H), 8.53 (s, 2H), 10.82 (br s, 1H); Mass spectrum 446.

EXAMPLE 36

5-[(1R)-1-methyl-2-oxo-2-pyrrolidin-1-ylethoxy]-N-[1-(1,3-thiazol-2-ylmethyl)-1H-indazol-5-yl]quinazolin-4-amine Using the same procedure as in Example 26, methyl (2R)-2-[(4-{[1-(1,3-thiazol-2-ylmethyl)-1H-indazol-5-yl]amino}quinazolin-5-yl)oxy]propanoate (250 mg, 0.54 mmol) was reacted with pyrrolidine (0.45 ml, 5.4 mmol) to give the title compound (160 mg, 59%) as a solid, except that the mixture was heated at 55° C. for 20 hours and purified by chromatography on silica gel (eluant: 1-5% methanol in DCM); NMR Spectrum 1.61 (d, 3H), 1.82 (m, 2H), 1.94 (m, 2H), 3.47-3.30 (m, 3H), 3.77 (m, 1H), 5.63 (q, 1H), 6.04 (s, 2H), 7.27 (d, 1H), 7.35 (d, 1H), 7.65 (d, 1H), 7.74 (m, 3H), 7.88 (dd, 1H), 8.20 (s, 1H), 8.52 (s, 1H), 8.56 (s, 1H), 11.09 (br s, 1H); Mass spectrum 500.

The methyl (2R)-2-[(4-{[1-(1,3-thiazol-2-ylmethyl)-1H-indazol-5-yl]amino}quinazolin-5-yl)oxy]propanoate used as starting material was made from 4-{[1-(1,3-thiazol-2-ylmethyl)-1H-indazol-5-yl]amino}quinazolin-5-ol and (S)-methyl lactate using the procedure described in Example 26, starting material:

Methyl (2R)-2-[(4-{[1-(1,3-thiazol-2-ylmethyl)-1H-indazol-5-yl]amino}quinazolin-5-yl)oxy]propanoate: white solid, Yield: 1.4 g, 76%; NMR Spectrum 1.72 (d, 3H), 3.80 (s, 3H), 5.54 (q, 1H), 6.05 (s, 2H), 7.18 (d, 1H), 7.38 (d, 1H), 7.80-7.66 (m, 5H), 8.21 (s, 1H), 8.48 (s, 1H), 8.54 (s, 1H), 10.53 (br s, 1H); Mass spectrum 461.

EXAMPLE 37

(2R)-2-[(4-{[1-(1,3-thiazol-2-ylmethyl)-1H-indazol-5-yl]amino}quinazolin-5-yl)oxy]propanamide Using the same procedure as in Example 5, methyl (2R)-2-[(4-{[1-(1,3-thiazol-2-ylmethyl)-1H-indazol-5-yl]amino}quinazolin-5-yl)oxy]propanoate (250 mg, 0.54 mmol) was reacted with ammonia to give the title compound as a white solid (212 mg, 88%); NMR Spectrum 1.67 (d, 3H), 5.14 (q, 1H), 6.04 (s, 2H), 7.02 (d, 1H), 7.36 (d, 1H), 7.56 (br s, 1H), 7.66 (d, 1H), 7.83-7.72 (m, 4H), 7.90 (br s, 1H), 8.19 (s, 1H), 8.53 (s, 2H), 10.82 (br s, 1H); Mass spectrum 446.

EXAMPLE 38

(2R)-2-[(4-{[1-(1,3-thiazol-4-ylmethyl)-1H-indazol-5-yl]amino}quinazolin-5-yl)oxy]propanamide Using the same procedure as in Example 5, methyl (2R)-2-[(4-{[1-(1,3-thiazol-4-ylmethyl)-1H-indazol-5-yl]amino}quinazolin-5-yl)oxy]propanoate (200 mg, 0.43 mmol) was reacted with ammonia to give the title compound as a white solid (170 mg, 88%); NMR Spectrum 1.67 (d, 3H), 5.14 (q, 1H), 5.79 (s, 2H), 7.02 (d, 1H), 7.36 (d, 1H), 7.50 (s, 1H), 7.56 (br s, 1H), 7.79-7.72 (m, 3H), 7.90 (br s, 1H), 8.10 (s, 1H), 8.51 (m, 2H), 9.04 (s, 1H), 10.80 (br s, 1H); Mass spectrum MH⁺ 446.

The methyl (2R)-2-[(4-{[1-(1,3-thiazol-4-ylmethyl)-1H-indazol-5-yl]amino}quinazolin-5-yl)oxy]propanoate used as starting material was made from 1-(1,3-thiazol-4-ylmethyl)-1H-indazol-5-amine, 4-chloro-5-fluoroquinazoline and (S)-methyl lactate using the procedure described in Example 26, starting material:

5-fluoro-N-[1-(1,3-thiazol-4-ylmethyl)-1H-indazol-5-yl]quinazolin-4-amine (solid): Yield: 13 g, 90%; Mass spectrum MH⁺ 377.

5-methoxy-N-[1-(1,3-thiazol-4-ylmethyl)-1H-indazol-5-yl]quinazolin-4-amine (beige solid): Yield: 13.4 g, 100%; Mass spectrum MH⁺ 389.

4-{[1-(1,3-thiazol-4-ylmethyl)-1H-indazol-5-yl]amino}quinazolin-5-ol (solid): Yield: 12.5 g, 100%; Mass spectrum MH⁺ 375.

Methyl (2R)-2-[(4-{[1-(1,3-thiazol-4-ylmethyl)-1H-indazol-5-yl]amino}quinazolin-5-yl)oxy]propanoate (white solid): Yield: 2.6 g, 70%, using the (S)-methyl lactate; NMR Spectrum (CDCl₃) 1.80 (d, 3H), 3.86 (s, 3H), 5.16 (q, 1H), 5.80 (s, 2H), 6.80 (d, 1H), 6.97 (s, 1H), 7.52 (m, 2H), 7.62 (t, 1H), 7.73 (m, 1H), 8.08 (s, 1H), 8.36 (s, 1H), 8.63 (s, 1H), 8.79 (s, 1H); Mass spectrum MH⁺ 461.

EXAMPLE 39

(2R)—N-methyl-2-[(4-{[1-(1,3-thiazol-4-ylmethyl)-1H-indazol-5-yl]amino}quinazolin-5-yl)oxy]propanamide Using the same procedure as in Example 5, methyl (2R)-2-[(4-{[1-(1,3-thiazol-4-ylmethyl)-1H-indazol-5-yl]amino}quinazolin-5-yl)oxy]propanoate (200 mg, 0.43 mmol) was reacted with methylamine to give the title compound as a white solid (156 mg, 78%); NMR Spectrum 1.65 (d, 3H), 2.68 (d, 3H), 5.16 (q, 1H), 5.80 (s, 2H), 7.00 (d, 1H), 7.36 (d, 1H), 7.51 (s, 1H), 7.79-7.71 (m, 3H), 8.12 (s, 1H), 8.39 (m, 1H), 8.52 (m, 2H), 9.05 (s, 1H), 10.68 (br s, 1H); Mass spectrum MH$^+$ 460.

EXAMPLE 40

(2R)—N-ethyl-2-[(4-{[1-(1,3-thiazol-4-ylmethyl)-1H-indazol-5-yl]amino}quinazolin-5-yl)oxy]propanamide Using the same procedure as in Example 5, methyl (2R)-2-[(4-{[1-(1,3-thiazol-4-ylmethyl)-1H-indazol-5-yl]amino}quinazolin-5-yl)oxy]propanoate (200 mg, 0.43 mmol) was reacted with ethylamine to give the title compound as a white solid (188 mg, 91%); NMR Spectrum 1.04 (t, 3H), 1.65 (d, 3H), 3.17 (m, 2H), 5.15 (q, 1H), 5.80 (s, 2H), 7.01 (d, 1H), 7.36 (d, 1H), 7.51 (s, 1H), 7.79-7.72 (m, 3H), 8.12 (s, 1H), 8.44 (m, 1H), 8.53 (m, 2H), 9.04 (s, 1H), 10.69 (br s, 1H); Mass spectrum MH$^+$ 474.

EXAMPLE 41

5-[(1R)-1-methyl-2-oxo-2-pyrrolidin-1-ylethoxy]-N-[1-(1,3-thiazol-4-ylmethyl)-1H-indazol-5-yl]quinazolin-4-amine Using the same procedure as in Example 26, methyl (2R)-2-[(4-{[1-(1,3-thiazol-4-ylmethyl)-1H-indazol-5-yl]amino}quinazolin-5-yl)oxy]propanoate (200 mg, 0.43 mmol) was reacted with pyrrolidine (0.36 ml, 4.3 mmol) to give the title compound as a solid (130 mg, 60%), except that the mixture was heated at 45° C. for 20 hours and purified by chromatography on silica gel (eluant: 3% methanol in DCM). NMR Spectrum 1.60 (d, 3H), 1.81 (m, 2H), 1.94 (m, 2H), 3.47-3.38 (m, 3H), 3.77 (m, 1H), 5.62 (q, 1H), 5.79 (s, 2H), 7.26 (d, 1H), 7.35 (d, 1H), 7.51 (s, 1H), 7.77-7.71 (m, 2H), 7.83 (m, 1H), 8.11 (s, 1H), 8.53 (m, 2H), 9.04 (s, 1H), 11.07 (br s, 1H); Mass spectrum MH$^+$ 500.

EXAMPLE 42

(2R)—N-(2-hydroxyethyl)-N-methyl-2-[(4-{[1-(1,3-thiazol-4-ylmethyl)-1H-indazol-5-yl]amino}quinazolin-5-yl)oxy]propanamide Using the same procedure as in Example 26, methyl (2R)-2-[(4-{[1-(1,3-thiazol-4-ylmethyl)-1H-indazol-5-yl]amino}quinazolin-5-yl)oxy]propanoate (200 mg, 0.43 mmol) was reacted with 2-(methylamino)ethanol (0.35 ml, 4.3 mmol) to give the title compound as a solid (160 mg, 73%), except that the mixture was heated at 45° C. for 20 hours and purified by chromatography on silica gel (eluant: 3% methanol in DCM). NMR Spectrum (2 rotamers) 1.60 (m, 3H), 3.18 and 2.93 (s, 3H), 3.65-3.40 (m, 4H), 5.00 and 4.73 (t, 1H), 5.79 (s, 2H), 5.90 and 5.81 (q, 1H), 7.35-7.30 (m, 2H), 7.51 (s, 1H), 7.85-7.70 (m, 3H), 8.11 (s, 1H), 8.51 (m, 2H), 9.04 (s, 1H), 11.09 (br s, 1H); Mass spectrum MH$^+$ 504.

EXAMPLE 43

(2R)—N-(2-hydroxyethyl)-2-[(4-{[1-(1,3-thiazol-4-ylmethyl)-1H-indazol-5-yl]amino}quinazolin-5-yl)oxy]propanamide Using the same procedure as in Example 26, methyl (2R)-2-[(4-{[1-(1,3-thiazol-4-ylmethyl)-1H-indazol-5-yl]amino}quinazolin-5-yl)oxy]propanoate (200 mg, 0.43 mmol) was reacted with ethanolamine (0.26 ml, 4.3 mmol) to give the title compound as a solid (170 mg, 80%), except that the mixture was heated at 45° C. for 20 hours. NMR Spectrum 1.65 (d, 3H), 3.22 (m, 2H), 3.43 (m, 2H), 4.75 (t, 1H), 5.23 (q, 1H), 5.79 (s, 2H), 7.02 (d, 1H), 7.36 (d, 1H), 7.51 (s, 1H), 7.79-7.72 (m, 3H), 8.11 (s, 1H), 8.48 (m, 1H), 8.51 (s, 2H), 9.04 (s, 1H), 10.72 (br s, 1H); Mass spectrum MH$^+$ 490.

EXAMPLE 44

5-[(1R)-1-methyl-2-morpholin-4-yl-2-oxoethoxy]-N-[1-(1,3-thiazol-4-ylmethyl)-1H-indazol-5-yl]quinazolin-4-amine A mixture of (2R)-2-[(4-{[1-(1,3-thiazol-4-ylmethyl)-1H-indazol-5-yl]amino}quinazolin-5-yl)oxy]propanoic acid (250 mg, 0.56 mmol), 2-hydroxypyridine-N-oxide (124 mg, 1.1 mmol), morpholine (0.098 ml, 1.1 mmol), diisopropylethylamine (0.195 ml, 1.1 mmol) and EDCI (214 mg, 1.1 mmol) in DMF (2 ml) was stirred at room temperature for 18 hours. Additional coupling agents were added (1 equivalent) and the mixture was stirred for 2 hours more. The reaction mixture was directly injected on an HPLC column (C18, 5 microns, 20 mm diameter, 100 mm length) of a preparative HPLC-MS system eluting with a mixture of water and acetonitrile containing 2 g/l of ammonium carbonate (gradient) to give the title compound as a white solid (180 mg, 62%); NMR Spectrum 1.58 (d, 3H), 3.70-3.40 (m, 8H), 5.79 (s, 2H), 5.88 (q, 1H), 7.29 (d, 1H), 7.35 (s, 1H), 7.51 (s, 1H), 7.75 (m, 2H), 7.84 (m, 1H), 8.10 (s, 1H), 8.51 (s, 2H), 9.04 (s, 1H), 11.12 (br s, 1H); Mass spectrum: MH$^+$ 516.

The (2R)-2-[(4-{[1-(1,3-thiazol-4-ylmethyl)-1H-indazol-5-yl]amino}quinazolin-5-yl)oxy]propanoic acid used as starting material was made as follows:

Aqueous sodium hydroxide (2N, 1 ml, 2 mmol) was added to a solution of methyl (2R)-2-[(4-{[1-(1,3-thiazol-4-ylmethyl)-1H-indazol-5-yl]amino}quinazolin-5-yl)oxy]propanoate (480 mg, 1 mmol) in THF (3 ml) and methanol (3 ml). The mixture was stirred at room temperature for 2 hours. After evaporation of the solvents, the pH of the mixture was adjusted to 3 by addition of 2N hydrochloric acid. The precipitate formed was filtered, washed with water and dried under high vacuum to give (2R)-2-[(4-{[1-(1,3-thiazol-4-ylmethyl)-1H-indazol-5-yl]amino}quinazolin-5-yl)oxy]propanoic acid (435 mg, 97%); Mass spectrum MH$^+$ 447.

EXAMPLE 45

(2S)—N,N-dimethyl-2-[(4-{[1-(1,3-thiazol-4-ylmethyl)-1H-indazol-5-yl]amino}quinazolin-5-yl)oxy]propanamide Using the same procedure as in Example 5, methyl (2S)-2-[(4-{[1-(1,3-thiazol-4-ylmethyl)-1H-indazol-5-yl]amino}quinazolin-5-yl)oxy]propanoate (200 mg, 0.43 mmol) was reacted with dimethylamine to give the title compound as a solid (120 mg, 58%); NMR Spectrum 1.59 (d, 3H), 2.93 (s, 3H), 3.14 (s, 3H), 5.79 (s, 2H), 5.85 (q, 1H), 7.29 (d, 1H), 7.34 (d, 1H), 7.51 (s, 1H), 7.77-7.72 (m, 2H), 7.83 (m, 1H), 8.11 (s, 1H), 8.52 (m, 2H), 9.04 (s, 1H), 11.12 (br s, 1H); Mass spectrum MH+ 474.

The methyl (2S)-2-[(4-{[1-(1,3-thiazol-4-ylmethyl)-1H-indazol-5-yl]amino}quinazolin-5-yl)oxy]propanoate used as starting material was made from 4-{[1-(1,3-thiazol-4-ylmethyl)-1H-indazol-5-yl]amino}quinazolin-5-ol according to Example 38 starting material, using the (R)-methyl lactate.

Methyl (2S)-2-[(4-{[1-(1,3-thiazol-4-ylmethyl)-1H-indazol-5-yl]amino}quinazolin-5-yl)oxy]propanoate (white solid): Yield: 3 g, 81%; NMR Spectrum (CDCl$_3$) 1.80 (d, 3H), 3.86 (s, 3H), 5.16 (q, 1H), 5.80 (s, 2H), 6.80 (d, 1H), 6.97 (s, 1H), 7.52 (m, 2H), 7.62 (t, 1H), 7.73 (m, 1H), 8.08 (s, 1H), 8.36 (s, 1H), 8.63 (s, 1H), 8.79 (s, 1H); Mass spectrum MH+ 461.

EXAMPLE 46

(2S)—N-methyl-2-[(4-{[1-(1,3-thiazol-4-ylmethyl)-1H-indazol-5-yl]amino}quinazolin-5-yl)oxy]propanamide Using the same procedure as in Example 5, methyl (2S)-2-[(4-{[1-(1,3-thiazol-4-ylmethyl)-1H-indazol-5-yl]amino}quinazolin-5-yl)oxy]propanoate (200 mg, 0.43 mmol) was reacted with methylamine to give the title compound as a white solid (170 mg, 85%); NMR Spectrum 1.65 (d, 3H), 2.68 (d, 3H), 5.16 (q, 1H), 5.80 (s, 2H), 7.00 (d, 1H), 7.36 (d, 1H), 7.51 (s, 1H), 7.79-7.71 (m, 3H), 8.12 (s, 1H), 8.39 (m, 1H), 8.52 (m, 2H), 9.05 (s, 1H), 10.68 (br s, 1H); Mass spectrum MH+ 460.

EXAMPLE 47

5-[(1S)-1-methyl-2-oxo-2-pyrrolidin-1-ylethoxy]-N-[1-(1,3-thiazol-4-ylmethyl)-1H-indazol-5-yl]quinazolin-4-amine Using the same procedure as in Example 26, methyl (2S)-2-[(4-{[1-(1,3-thiazol-4-ylmethyl)-1H-indazol-5-yl]amino}quinazolin-5-yl)oxy]propanoate (200 mg, 0.43 mmol) was reacted with pyrrolidine (0.36 ml, 4.3 mmol) to give the title compound as a solid (130 mg, 60%), except that the mixture was heated at 45° C. for 20 hours and purified by chromatography on silica gel (eluant: 3% methanol in DCM). NMR Spectrum 1.60 (d, 3H), 1.81 (m, 2H), 1.94 (m, 2H), 3.47-3.38 (m, 3H), 3.77 (m, 1H), 5.62 (q, 1H), 5.79 (s, 2H), 7.26 (d, 1H), 7.35 (d, 1H), 7.51 (s, 1H), 7.77-7.71 (m, 2H), 7.83 (m, 1H), 8.11 (s, 1H), 8.53 (m, 2H), 9.04 (s, 1H), 11.07 (br s, 1H); Mass spectrum MH+ 500.

EXAMPLE 48

5-[(1S)-1-methyl-2-morpholin-4-yl-2-oxoethoxy]-N-[1-(1,3-thiazol-4-ylmethyl)-1H-indazol-5-yl]quinazolin-4-amine Using the same procedure as in Example 44, (2S)-2-[(4-{[1-(1,3-thiazol-4-ylmethyl)-1H-indazol-5-yl]amino}quinazolin-5-yl)oxy]propanoic acid (250 mg, 0.56 mmol) was reacted with morpholine to give the title compound as a white solid (160 mg, 55%); NMR Spectrum 1.58 (d, 3H), 3.70-3.40 (m, 8H), 5.79 (s, 2H), 5.88 (q, 1H), 7.29 (d, 1H), 7.35 (s, 1H), 7.51 (s, 1H), 7.75 (m, 2H), 7.84 (m, 1H), 8.10 (s, 1H), 8.51 (s, 2H), 9.04 (s, 1H), 11.12 (br s, 1H); Mass spectrum MH+ 516.

The (2S)-2-[(4-{[1-(1,3-thiazol-4-ylmethyl)-1H-indazol-5-yl]amino}quinazolin-5-yl)oxy]propanoic acid used as starting material was made from methyl (2S)-2-[(4-{[1-(1,3-thiazol-4-ylmethyl)-1H-indazol-5-yl]amino}quinazolin-5-yl)oxy]propanoate according to the procedure described in Example 44 starting material:

(2S)-2-[(4-{[1-(1,3-thiazol-4-ylmethyl)-1H-indazol-5-yl]amino}quinazolin-5-yl)oxy]propanoic acid (white solid): Yield: 448 mg, 100%; Mass spectrum MH+ 447.

EXAMPLE 49

(2S)—N-methyl-2-[(4-{[1-(pyridin-2-ylmethyl)-1H-indazol-5-yl]amino}quinazolin-5-yl)oxy]propanamide Using the same procedure as in Example 5, methyl (2S)-2-[(4-{[1-(pyridin-2-ylmethyl)-1H-indazol-5-yl]amino}quinazolin-5-yl)oxy]propanoate (250 mg, 0.55 mmol) was reacted with methylamine to give the title compound as a beige solid (110 mg, 46%); NMR Spectrum 1.65 (d, 3H), 2.67 (d, 3H), 5.16 (q, 1H), 5.77 (s, 2H), 6.96 (d, 1H), 7.00 (d, 1H), 7.29 (m, 1H), 7.36 (d, 1H), 7.72 (m, 4H), 8.17 (s, 1H), 8.38 (m, 1H), 8.53 (m, 3H), 10.68 (br s, 1H); Mass spectrum MH+ 454.

EXAMPLE 50

5-[(1S)-1-methyl-2-morpholin-4-yl-2-oxoethoxy]-N-[1-(pyridin-2-ylmethyl)-1H-indazol-5-yl]quinazolin-4-amine Using the same procedure as in Example 44, (2S)-2-[(4-{[1-(pyridin-2-ylmethyl)-1H-indazol-5-yl]amino}quinazolin-5-yl)oxy]propanoic acid (300 mg, 0.68 mmol) was reacted with morpholine to give the title compound as a white solid (120 mg, 34%); NMR spectrum 1.58 (d, 3H), 3.67-3.58 (m, 8H), 5.77 (s, 2H), 5.88 (q, 1H), 6.95 (d, 1H), 7.29 (m, 2H), 7.35 (d, 1H), 7.75-7.67 (m, 3H), 7.83 (m, 1H), 8.15 (s, 1H), 8.52 (m, 3H), 11.12 (s, 1H); Mass spectrum MH+ 510.

The (2S)-2-[(4-{[1-(pyridin-2-ylmethyl)-1H-indazol-5-yl]amino}quinazolin-5-yl)oxy]propanoic acid was made from methyl (2S)-2-[(4-{[1-(pyridin-2-ylmethyl)-1H-indazol-5-yl]amino}quinazolin-5-yl)oxy]propanoate according to the procedure described in Example 44 starting material:

(2S)-2-[(4-{[1-(pyridin-2-ylmethyl)-1H-indazol-5-yl]amino}quinazolin-5-yl)oxy]propanoic acid (solid): Yield: 440 mg, 100%; Mass spectrum MH+ 441.

EXAMPLE 51

(2R)-2-[(4-{[1-(3-fluorobenzyl)-1H-indazol-5-yl]amino}quinazolin-5-yl)oxy]-N-methylpropanamide Using the same procedure as in Example 26, methyl (2R)-2-[(4-{[1-(3-fluorobenzyl)-1H-indazol-5-yl]amino}quinazolin-5-yl)oxy]propanoate (200 mg, 0.42 mmol) was reacted with methylamine to give the title compound as a white solid (110 mg, 55%) except that the crude material was purified on an HPLC column (C18, 5 microns, 19 mm diameter, 100 mm length) of a preparative HPLC-MS system eluting with a mixture of water and acetonitrile containing 2 g/l of ammonium carbonate (gradient). NMR Spectrum 1.65 (d, 3H), 2.67 (d, 3H), 5.16 (q, 1H), 5.71 (s, 2H), 7.00 (d, 1H), 7.04-7.10 (m, 3H), 7.36 (dd, 2H), 7.71-7.77 (m, 3H), 8.17 (s, 1H), 8.37 (m, 1H), 8.53 (s, 1H), 8.55 (s, 1H), 10.68 (br s, 1H); Mass spectrum MH$^+$ 471.

EXAMPLE 52

(2R)-2-[(4-{[1-(3-fluorobenzyl)-1H-indazol-5-yl] amino}quinazolin-5-yl)oxy]-N-ethylpropanamide Using the same procedure as in Example 5, methyl (2R)-2-[(4-{[1-(3-fluorobenzyl)-1H-indazol-5-yl] amino}quinazolin-5-yl)oxy]propanoate (250 mg, 0.53 mmol) was reacted with ethylamine to give the title compound as a white solid (195 mg, 76%); NMR Spectrum 1.04 (t, 3H), 1.65 (d, 3H), 3.14-3.20 (m, 2H), 5.16 (q, 1H), 5.71 (s, 2H), 7.01 (d, 1H), 7.04-7.12 (m, 3H), 7.36 (dd, 2H), 7.72-7.78 (m, 3H), 8.17 (s, 1H), 8.44 (m, 1H), 8.53 (s, 1H), 8.56 (s, 1H), 10.68 (br s, 1H); Mass spectrum MH$^+$ 485.

EXAMPLE 53

(2R)-2-[(4-{[1-(3-fluorobenzyl)-1H-indazol-5-yl] amino}quinazolin-5-yl)oxy]-N-(2-hydroxyethyl) propanamide Using the same procedure as in Example 26, methyl (2R)-2-[(4-{[1-(3-fluorobenzyl)-1H-indazol-5-yl] amino}quinazolin-5-yl)oxy]propanoate (200 mg, 0.42 mmol) was reacted with ethanolamine (0.15 mL, 2.5 mmol) to give the title compound as a white solid (170 mg, 80%); NMR Spectrum 1.65 (d, 3H), 3.22 (q, 2H), 3.41-3.45 (m, 2H), 4.75 (t, 1H), 5.22 (q, 1H), 5.70 (s, 2H), 7.01-7.12 (m, 4H), 7.36 (dd, 2H), 7.72-7.76 (m, 3H), 8.17 (s, 1H), 8.47 (m, 1H), 8.53 (s, 1H), 8.56 (s, 1H), 10.73 (br s, 1H); Mass spectrum MH$^+$ 501.

EXAMPLE 54

(2R)-2-[(4-{[1-(3-fluorobenzyl)-1H-indazol-5-yl] amino}quinazolin-5-yl)oxy]-N-(2-hydroxyethyl)-N-methylpropanamide Using the same procedure as in Example 26, methyl (2R)-2-[(4-{[1-(3-fluorobenzyl)-1H-indazol-5-yl] amino}quinazolin-5-yl)oxy]propanoate (205 mg, 0.43 mmol) was reacted with 2-methylaminoethanol (326 mg, 4.3 mmol) to give the title compound as a white solid (124 mg, 56%) except that the reaction mixture was heated at 45° C. for 24 hours and the crude material was purified on an HPLC column (C18, 5 microns, 19 mm diameter, 100 mm length) of a preparative HPLC-MS system eluting with a mixture of water and acetonitrile containing 2 g/l of ammonium carbonate (gradient). NMR Spectrum (2 rotamers) 1.59-1.62 (m, 3H), 3.18 and 2.93 (s, 3H), 3.53-3.65 (m, 4H), 5.00 and 4.74 (t, 1H), 5.71 (s, 2H), 5.90 and 5.81 (q, 1H), 7.05-7.07 (m, 3H), 7.30-7.37 (m, 3H), 7.71-7.77 (m, 2H), 7.82-7.88 (m, 1H), 8.17 (s, 1H), 8.51 (s, 1H), 8.55 and 8.58 (s, 1H), 11.10 (br s, 1H); Mass spectrum MH$^+$ 515.

EXAMPLE 55

N-[1-(3-fluorobenzyl)-1H-indazol-5-yl]-5-[(1R)-1-methyl-2-morpholin-4-yl-2-oxoethoxy]quinazolin-4-amine Using the same procedure as in Example 44, (2R)-2-[(4-{[1-(3-fluorobenzyl)-1H-indazol-5-yl]amino}quinazolin-5-yl)oxy]propanoic acid (300 mg, 0.66 mmol) was reacted with morpholine to give the title compound as a white solid (144 mg, 42%); NMR Spectrum 1.58 (d, 3H), 3.46-3.73 (m, 8H), 5.70 (s, 2H), 5.88 (q, 1H), 7.04-7.12 (m, 3H), 7.29 (d, 1H), 7.34-7.37 (m, 2H), 7.72-7.75 (m, 2H), 7.86 (d, 1H), 8.16 (s, 1H), 8.51 (s, 1H), 8.54 (s, 1H), 11.13 (br s, 1H); Mass spectrum MH$^+$ 527.

The (2R)-2-[(4-{[1-(3-fluorobenzyl)-1H-indazol-5-yl] amino}quinazolin-5-yl)oxy]propanoic acid was made from methyl (2R)-2-[(4-{[1-(3-fluorobenzyl)-1H-indazol-5-yl] amino}quinazolin-5-yl)oxy]propanoate according to the procedure described in Example 44 starting material:

(2R)-2-[(4-{[1-(3-fluorobenzyl)-1H-indazol-5-yl] amino}quinazolin-5-yl)oxy]propanoic acid (solid): Yield: 477 mg, 98%; Mass spectrum MH$^+$ 458.

EXAMPLE 56

(2S)-2-[(4-{[1-(3-fluorobenzyl)-1H-indazol-5-yl] amino}quinazolin-5-yl)oxy]-N-methylpropanamide Using the same procedure as in Example 26, methyl (2S)-2-[(4-{[1-(3-fluorobenzyl)-1H-indazol-5-yl] amino}quinazolin-5-yl)oxy]propanoate (200 mg, 0.42 mmol) was reacted with methylamine to give the title compound as a white solid (126 mg, 63%) except that the crude material was purified on an HPLC column (C18, 5 microns, 19 mm diameter, 100 mm length) of a preparative HPLC-MS system eluting with a mixture of water and acetonitrile containing 2 g/l of ammonium carbonate (gradient). NMR Spectrum 1.65 (d, 3H), 2.67 (d, 3H), 5.16 (q, 1H), 5.71 (s, 2H), 7.00 (d, 1H), 7.04-7.10 (m, 3H), 7.36 (dd, 2H), 7.71-7.77 (m, 3H), 8.17 (s, 1H), 8.37 (m, 1H), 8.53 (s, 1H), 8.55 (s, 1H), 10.68 (br s, 1H); Mass spectrum MH$^+$ 471.

EXAMPLE 57

N-[1-(3-fluorobenzyl)-1H-indazol-5-yl]-5-[(1S)-1-methyl-2-morpholin-4-yl-2-oxoethoxy]quinazolin-4-amine Using the same procedure as in Example 44, (2S)-2-[(4-{[1-(3-fluorobenzyl)-1H-indazol-5-yl]amino}quinazolin-5-yl)oxy]propanoic acid (400 mg, 0.87 mmol) was reacted with morpholine to give the title compound as a white solid (120 mg, 26%); NMR Spectrum 1.58 (d, 3H), 3.46-3.73 (m, 8H), 5.70 (s, 2H), 5.88 (q, 1H), 7.04-7.12 (m, 3H), 7.29 (d, 1H), 7.34-7.37 (m, 2H), 7.72-7.75 (m, 2H), 7.86 (d, 1H), 8.16 (s, 1H), 8.51 (s, 1H), 8.54 (s, 1H), 11.13 (br s, 1H); Mass spectrum MH$^+$ 527.

The (2S)-2-[(4-{[1-(3-fluorobenzyl)-1H-indazol-5-yl] amino}quinazolin-5-yl)oxy]propanoic acid was made from methyl (2S)-2-[(4-{[1-(3-fluorobenzyl)-1H-indazol-5-yl] amino}quinazolin-5-yl)oxy]propanoate according to the procedure described in Example 44 starting material:

(2S)-2-[(4-{[1-(3-fluorobenzyl)-1H-indazol-5-yl] amino}quinazolin-5-yl)oxy]propanoic acid (solid): Yield: 231 mg, 79%; Mass spectrum MH$^+$ 458.

EXAMPLE 58

(2R)—N-(2-hydroxyethyl)-2-[(4-{[1-(1,3-thiazol-2-ylmethyl)-1H-indazol-5-yl]amino}quinazolin-5-yl) oxy]propanamide Using the same procedure as in Example 26, methyl (2R)-2-[(4-{[1-(1,3-thiazol-2-ylmethyl)-1H-indazol-5-yl] amino}quinazolin-5-yl)oxy]propanoate (210 mg, 0.46 mmol) was reacted with ethanolamine (0.17 ml, 2.7 mmol) to give the title compound as a solid (185 mg, 83%), except that the mixture was heated at 65° C. for 2 hours. NMR Spectrum 1.65 (d, 3H), 3.21-3.25 (m, 2H), 3.42-3.46 (m, 2H), 4.75 (t, 1H), 5.23 (q, 1H), 6.04 (s, 2H), 7.02 (d, 1H), 7.37 (d, 1H), 7.66 (s, 1H), 7.73 (t, 1H), 7.77-7.79 (m, 3H) 8.21 (s, 1H), 8.48 (m, 1H), 8.54 (s, 1H), 8.57 (s, 1H), 10.75 (br s, 1H); Mass spectrum MH+ 490.

EXAMPLE 59

(2R)—N-(2-hydroxyethyl)-N-methyl-2-[(4-{[1-(1,3-thiazol-2-ylmethyl)-1H-indazol-5-yl]amino}quinazolin-5-yl)oxy]propanamide Using the same procedure as in Example 26, methyl (2R)-2-[(4-{[1-(1,3-thiazol-2-ylmethyl)-1H-indazol-5-yl]amino}quinazolin-5-yl)oxy]propanoate (200 mg, 0.43 mmol) was reacted with 2-(methylamino)ethanol (0.35 ml, 4.3 mmol) to give the title compound as a solid (173 mg, 79%), except that the mixture was heated at 45° C. for 24 hours and purified on an HPLC column (C18, 5 microns, 19 mm diameter, 100 mm length) of a preparative HPLC-MS system eluting with a mixture of water and acetonitrile containing 2 g/l of ammonium carbonate (gradient). NMR Spectrum (2 rotamers) 1.60-1.63 (m, 3H), 3.18 and 2.93 (s, 3H), 3.41-3.65 (m, 4H), 5.01 and 4.75 (br s, 1H), 5.81 and 5.91 (q, 1H), 6.04 (s, 2H), 7.30-7.36 (m, 2H), 7.66 (s, 1H), 7.71-7.78 (m, 3H), 8.84-8.90 (m, 1H), 8.20 (s, 1H), 8.52 (s, 1H), 8.55 and 8.58 (s, 1H), 11.12 (br s, 1H); Mass spectrum MH+ 504.

EXAMPLE 60

(2R)—N-ethyl-2-[(4-{[1-(1,3-thiazol-2-ylmethyl)-1H-indazol-5-yl]amino}quinazolin-5-yl)oxy]propanamide Using the same procedure as in Example 5, methyl (2R)-2-[(4-{[1-(1,3-thiazol-2-ylmethyl)-1H-indazol-5-yl]amino}quinazolin-5-yl)oxy]propanoate (200 mg, 0.43 mmol) was reacted with ethylamine to give the title compound as a white solid (158 mg, 77%); NMR Spectrum 1.04 (t, 3H), 1.65 (d, 3H), 3.17 (m, 2H), 5.15 (q, 1H), 6.04 (s, 2H), 7.01 (d, 1H), 7.37 (d, 1H), 7.66 (s, 1H), 7.72-7.80 (m, 4H), 8.21 (s, 1H), 8.44 (m, 1H), 8.54 (s, 1H), 8.56 (s, 1H), 10.71 (br s, 1H); Mass spectrum MH+ 474.

EXAMPLE 61

(2R)—N-methyl-2-[(4-{[1-(1,3-thiazol-2-ylmethyl)-1H-indazol-5-yl]amino}quinazolin-5-yl)oxy]propanamide Using the same procedure as in Example 5, methyl (2R)-2-[(4-{[1-(1,3-thiazol-2-ylmethyl)-1H-indazol-5-yl]amino}quinazolin-5-yl)oxy]propanoate (210 mg, 0.46 mmol) was reacted with methylamine to give the title compound as a white solid (181 mg, 86%); NMR Spectrum 1.66 (d, 3H), 2.68 (d, 3H), 5.16 (q, 1H), 6.04 (s, 2H), 7.01 (d, 1H), 7.37 (d, 1H), 7.66 (s, 1H), 7.72-7.80 (m, 4H), 8.21 (s, 1H), 8.39 (m, 1H), 8.54 (s, 1H), 8.56 (s, 1H), 10.70 (br s, 1H); Mass spectrum MH+ 460.

EXAMPLE 62

5-[(1R)-1-methyl-2-morpholin-4-yl-2-oxoethoxy]-N-[1-(1,3-thiazol-2-ylmethyl)-1H-indazol-5-yl]quinazolin-4-amine Using the same procedure as in Example 44, (2R)-2-[(4-{[1-(1,3-thiazol-2-ylmethyl)-1H-indazol-5-yl]amino}quinazolin-5-yl)oxy]propanoic acid (390 mg, 0.87 mmol) was reacted with morpholine to give the title compound as a white solid (148 mg, 33%); NMR Spectrum 1.58 (d, 3H), 3.40-3.75 (m, 8H), 5.88 (q, 1H), 6.04 (s, 2H), 7.29 (d, 1H), 7.36 (d, 1H), 7.66 (s, 1H), 7.73-7.78 (m, 3H), 7.88-7.90 (m, 1H), 8.20 (s, 1H), 8.52 (s, 1H), 8.55 (s, 1H), 11.15 (br s, 1H); Mass spectrum MH+ 516.

The (2R)-2-[(4-{[1-(1,3-thiazol-2-ylmethyl)-1H-indazol-5-yl]amino}quinazolin-5-yl)oxy]propanoic acid used as starting material was made from methyl (2R)-2-[(4-{[1-(1,3-thiazol-2-ylmethyl)-1H-indazol-5-yl]amino}quinazolin-5-yl)oxy]propanoate according to the procedure described in Example 44 starting material:

(2R)-2-[(4-{[1-(1,3-thiazol-2-ylmethyl)-1H-indazol-5-yl]amino}quinazolin-5-yl)oxy]propanoic acid (white solid); Yield: 393 mg, 99%; Mass spectrum MH+ 447.

EXAMPLE 63

(2S)—N-methyl-2-[(4-{[1-(1,3-thiazol-2-ylmethyl)-1H-indazol-5-yl]amino}quinazolin-5-yl)oxy]propanamide Using the same procedure as in Example 5, methyl (2S)-2-[(4-{[1-(1,3-thiazol-2-ylmethyl)-1H-indazol-5-yl]amino}quinazolin-5-yl)oxy]propanoate (210 mg, 0.46 mmol) was reacted with methylamine to give the title compound as a white solid (178 mg, 84%); NMR Spectrum 1.66 (d, 3H), 2.68 (d, 3H), 5.16 (q, 1H), 6.04 (s, 2H), 7.01 (d, 1H), 7.37 (d, 1H), 7.66 (s, 1H), 7.72-7.80 (m, 4H), 8.21 (s, 1H), 8.39 (m, 1H), 8.54 (s, 1H), 8.56 (s, 1H), 10.70 (br s, 1H); Mass spectrum MH+ 460.

EXAMPLE 64

5-[(1S)-1-methyl-2-morpholin-4-yl-2-oxoethoxy]-N-[1-(1,3-thiazol-2-ylmethyl)-1H-indazol-5-yl]quinazolin-4-amine Using the same procedure as in Example 44, (2S)-2-[(4-{[1-(1,3-thiazol-2-ylmethyl)-1H-indazol-5-yl]amino}quinazolin-5-yl)oxy]propanoic acid (380 mg, 0.84 mmol) was reacted with morpholine to give the title compound as a white solid (158 mg, 37%); NMR Spectrum 1.58 (d, 3H), 3.40-3.75 (m, 8H), 5.88 (q, 1H), 6.04 (s, 2H), 7.29 (d, 1H), 7.36 (d, 1H), 7.66 (s, 1H), 7.73-7.78 (m, 3H), 7.88-7.90 (m, 1H), 8.20 (s, 1H), 8.52 (s, 1H), 8.55 (s, 1H), 11.15 (br s, 1H); Mass spectrum MH+ 516.

The (2S)-2-[(4-{[1-(1,3-thiazol-2-ylmethyl)-1H-indazol-5-yl]amino}quinazolin-5-yl)oxy]propanoic acid used as starting material was made from methyl (2S)-2-[(4-{[1-(1,3-thiazol-2-ylmethyl)-1H-indazol-5-yl]amino}quinazolin-5-yl)oxy]propanoate according to the procedure described in Example 44 starting material:

(2S)-2-[(4-{[1-(1,3-thiazol-2-ylmethyl)-1H-indazol-5-yl]amino}quinazolin-5-yl)oxy]propanoic acid (white solid): Yield: 389 mg, 100%; Mass spectrum MH+ 447.

The invention claimed is:
1. A compound of the Formula I:

wherein:
R$^1$ is selected from hydrogen, hydroxy, (1-4C)alkoxy and (1-4C)alkoxy(1-4C)alkoxy;
G$^1$, G$^2$, G$^3$ and G$^4$ are each, independently, selected from hydrogen and halogeno;
X$^1$ is selected from SO$_2$, CO, SO$_2$N(R$^6$) and C(R$^6$)$_2$, wherein each R$^6$ is, independently, selected from hydrogen and (1-4C)alkyl;
Q$^1$ is aryl or heteroaryl, which aryl or heteroaryl group optionally bears one or more substituents independently selected from halogeno, cyano, (1-4C)alkoxy and (1-4C)alkyl;
R$^2$ and R$^3$, which may be the same or different, are selected from hydrogen, (2-4C)alkenyl, (2-4C)alkynyl and (1-4C)alkyl, which (1-4C)alkyl optionally bears one or more hydroxy substituents, or
R$^2$ and R$^3$ together with the carbon atom to which they are attached form a cyclopropyl ring;
R$^4$ and R$^5$, which may be the same or different, are selected from hydrogen, (3-4C)alkenyl, (3-4C)alkynyl and (1-4C)alkyl, which (1-4C)alkyl optionally bears one or more substituents independently selected from halogeno, cyano, hydroxy, amino, (1-4C)alkylamino, di-[(1-4C)alkyl]amino and (1-4C)alkoxy, or
R$^4$ and R$^5$ together with the nitrogen atom to which they are attached form a saturated 4, 5, 6 or 7 membered heterocyclic ring which optionally contains one or more additional heteroatoms independently selected from oxygen, S, SO, SO$_2$ and N(R$^7$), wherein R$^7$ is selected from hydrogen and (1-4C)alkyl,
and wherein any heterocyclic ring formed by R$^4$, R$^5$ and the nitrogen atom to which they are attached optionally bears one or more substituents independently selected from halogeno, cyano, hydroxy, (1-4C)alkyl and (1-4C)alkoxy, and wherein any heterocyclic ring formed by R$^4$, R$^5$ and the nitrogen atom to which they are attached optionally bears 1 or 2 oxo or thioxo substituents;
or a pharmaceutically acceptable salt thereof.
2. The compound according to claim 1, wherein:
R$^1$ is selected from hydrogen, hydroxy, (1-4C)alkoxy and (1-4C)alkoxy(1-4C)alkoxy;
G$^1$, G$^2$, G$^3$ and G$^4$ are each, independently, selected from hydrogen and halogeno;
X$^1$ is selected from SO$_2$, CO, SO$_2$N(R$^6$) and C(R$^6$)$_2$, wherein each R$^6$ is, independently, selected from hydrogen and (1-4C)alkyl;
Q$^1$ is aryl or heteroaryl, which aryl or heteroaryl group optionally bears one or more substituents independently selected from halogeno, cyano, (1-4C)alkoxy and (1-4C)alkyl;
R$^2$ and R$^3$, which may be the same or different, are selected from hydrogen and (1-4C)alkyl, which (1-4C)alkyl optionally bears one or more hydroxy substituents, or
R$^2$ and R$^3$ together with the carbon atom to which they are attached form a cyclopropyl ring;
R$^4$ and R$^5$, which may be the same or different, are selected from hydrogen and (1-4C)alkyl, which (1-4C)alkyl optionally bears one or more substituents independently selected from hydroxy, amino, (1-4C)alkylamino, di-[(1-4C)alkyl]amino and (1-4C)alkoxy, or
R$^4$ and R$^5$ together with the nitrogen atom to which they are attached form a saturated 4, 5, 6 or 7 membered heterocyclic ring which optionally contains one or more additional heteroatoms independently selected from oxygen, S, SO, SO$_2$ and N(R$^7$), wherein R$^7$ is selected from hydrogen and (1-4C)alkyl,
and wherein any heterocyclic ring formed by R$^4$, R$^5$ and the nitrogen atom to which they are attached optionally bears one or more substituents independently selected from halogeno, cyano, hydroxy, (1-4C)alkyl and (1-4C)alkoxy,
and wherein any heterocyclic ring formed by R$^4$, R$^5$ and the nitrogen atom to which they are attached optionally bears 1 or 2 oxo or thioxo substituents;
or a pharmaceutically acceptable salt thereof.
3. The compound according to claim 1, wherein R$^1$ is selected from hydrogen and methoxy.
4. The compound according to claim 3, wherein R$^1$ is hydrogen.
5. The compound according to claim 1, wherein G$^1$, G$^2$, G$^3$ and G$^4$ are each, independently, selected from hydrogen, chloro and fluoro.
6. The compound according to claim 5, wherein G$^1$, G$^2$, G$^3$ and G$^4$ are all hydrogen.
7. The compound according to claim 1, wherein X$^1$ is C(R$^6$)$_2$, wherein each R$^6$ is, independently, selected from hydrogen and (1-4C)alkyl.
8. The compound according to claim 7, wherein X$^1$ is CH$_2$.
9. The compound according to claim 1, wherein Q$^1$ is selected from phenyl and a 5- or 6-membered monocyclic heteroaryl ring, which ring contains 1, 2 or 3 heteroatoms independently selected from oxygen, nitrogen and sulfur, which phenyl or heteroaryl group optionally bears 1, 2 or 3 substituents independently selected from halogeno, cyano, (1-4C)alkyl and (1-4C)alkoxy.
10. The compound according to claim 9, wherein Q$^1$ is selected from phenyl, pyridinyl, 1,3-thiazolyl and 1,3-oxazolyl, which optionally bears 1, 2 or 3 substituents independently selected from halogeno, cyano, (1-4C)alkyl and (1-4C)alkoxy.
11. The compound according to claim 10, wherein Q$^1$ is selected from 3-fluorophenyl, 3-methoxyphenyl, 2-cyanophenyl, 2-pyridinyl, 6-fluoro-pyridin-3-yl, 1,3-thiazol-4-yl, 1,3-thiazol-2-yl, 2-methyl-1,3-thiazol-5-yl and 1,3-oxazol-2-yl.
12. The compound according to claim 1, wherein R$^2$ and R$^3$ are each, independently, selected from hydrogen and (1-2C)alkyl.
13. The compound according to claim 12, wherein R$^2$ is hydrogen and R$^3$ is (1-2C)alkyl.
14. The compound according to claim 12, wherein R$^2$ and R$^3$ are both hydrogen.

15. The compound according to claim 1, wherein $R^4$ and $R^5$, which may be the same or different, are selected from hydrogen and (1-4C)alkyl, which (1-4C)alkyl optionally bears one or more hydroxy substituents, or $R^4$ and $R^5$ together with the nitrogen atom to which they are attached form a heterocyclic ring selected from azetidin-1-yl, pyrrolidin-1-yl, pyrazolidin-1-yl, piperidin-1-yl, morpholin-4-yl and piperazin-1-yl, wherein any heterocyclic ring optionally bears one or more substituents independently selected from halogeno, cyano, hydroxy, (1-4C)alkyl and (1-4C)alkoxy, and wherein any heterocyclic ring optionally bears 1 or 2 oxo or thioxo substituents.

16. The compound according to claim 15, wherein $R^4$ is hydrogen and $R^5$ is (1-4C)alkyl, which (1-4C)alkyl optionally bears one or more hydroxy substituents.

17. The compound according to claim 15, wherein $R^4$ and $R^5$ are both (1-4C)alkyl, which (1-4C)alkyl optionally bears one or more hydroxy substituents.

18. The compound according to claim 15, wherein $R^4$ and $R^5$ together with the nitrogen atom to which they are attached form a heterocyclic ring selected from pyrrolidin-1-yl and morpholin-4-yl, which heterocyclic ring optionally bears one or more substituents independently selected from halogeno, cyano, hydroxy, (1-4C)alkyl and (1-4C)alkoxy, and which heterocyclic ring optionally bears 1 or 2 oxo or thioxo substituents.

19. The compound of the Formula I according to claim 1 selected from one or more of the following:

(2R)—N-(2-hydroxyethyl)-N-methyl-2-[(4-{[1-(pyridin-2-ylmethyl)-1H-indazol-5-yl]amino}quinazolin-5-yl)oxy]propanamide;

5-[(1R)-1-methyl-2-morpholin-4-yl-2-oxoethoxy]-N-[1-(pyridin-2-ylmethyl)-1H-indazol-5-yl]quinazolin-4-amine;

(2R)—N,N-dimethyl-2-[(4-{[1-(pyridin-2-ylmethyl)-1H-indazol-5-yl]amino}quinazolin-5-yl)oxy]propanamide;

(2S)—N,N-dimethyl-2-[(4-{[1-(pyridin-2-ylmethyl)-1H-indazol-5-yl]amino}quinazolin-5-yl)oxy]propanamide;

(2R)-2-[(4-{[1-(pyridin-2-ylmethyl)-1H-indazol-5-yl]amino}quinazolin-5-yl)oxy]propanamide;

(2R)—N-methyl-2-[(4-{[1-(pyridin-2-ylmethyl)-1H-indazol-5-yl]amino}quinazolin-5-yl)oxy]propanamide;

(2R)—N-ethyl-2-[(4-{[1-(pyridin-2-ylmethyl)-1H-indazol-5-yl]amino}quinazolin-5-yl)oxy]propanamide;

5-[(1R)-1-methyl-2-oxo-2-pyrrolidin-1-ylethoxy]-N-[1-(pyridin-2-ylmethyl)-1H-indazol-5-yl]quinazolin-4-amine;

(2R)—N-(2-hydroxyethyl)-2-[(4-{[1-(pyridin-2-ylmethyl)-1H-indazol-5-yl]amino}quinazolin-5-yl)oxy]propanamide;

N,N-dimethyl-2-[(4-{[1-(pyridin-2-ylmethyl)-1H-indazol-5-yl]amino}quinazolin-5-yl)oxy]acetamide;

2-[(4-{[1-(pyridin-2-ylmethyl)-1H-indazol-5-yl]amino}quinazolin-5-yl)oxy]acetamide;

N-ethyl-2-[(4-{[1-(pyridin-2-ylmethyl)-1H-indazol-5-yl]amino}quinazolin-5-yl)oxy]acetamide;

N-(2-hydroxyethyl)-2-[(4-{[1-(pyridin-2-ylmethyl)-1H-indazol-5-yl]amino}quinazolin-5-yl)oxy]acetamide;

N-methyl-2-[(4-{[1-(pyridin-2-ylmethyl)-1H-indazol-5-yl]amino}quinazolin-5-yl)oxy]acetamide;

N-(2-hydroxyethyl)-N-methyl-2-[(4-{[1-(pyridin-2-ylmethyl)-1H-indazol-5-yl]amino}quinazolin-5-yl)oxy]acetamide;

5-(2-oxo-2-pyrrolidin-1-ylethoxy)-N-[1-(pyridin-2-ylmethyl)-1H-indazol-5-yl]quinazolin-4-amine;

5-(2-morpholin-4-yl-2-oxoethoxy)-N-[1-(pyridin-2-ylmethyl)-1H-indazol-5-yl]quinazolin-4-amine;

(2R)—N,N-dimethyl-2-[(4-{[1-(1,3-thiazol-4-ylmethyl)-1H-indazol-5-yl]amino}quinazolin-5-yl)oxy]propanamide;

(2R)-2-[(4-{[1-(3-fluorobenzyl)-1H-indazol-5-yl]amino}quinazolin-5-yl)oxy]-N,N-dimethylpropanamide;

(2R)—N,N-dimethyl-2-[(4-{[1-(1,3-thiazol-2-ylmethyl)-1H-indazol-5-yl]amino}quinazolin-5-yl)oxy]propanamide;

(2R)—N,N-dimethyl-2-{[4-({1-[(2-methyl-1,3-thiazol-5-yl)methyl]-1H-indazol-5-yl}amino)quinazolin-5-yl]oxy}propanamide;

(2R)-2-{[4-({1-[(6-fluoropyridin-3-yl)methyl]-1H-indazol-5-yl}amino)quinazolin-5-yl]oxy}-N,N-dimethylpropanamide;

(2R)-2-[(4-{[1-(3-methoxybenzyl)-1H-indazol-5-yl]amino}quinazolin-5-yl)oxy]-N,N-dimethylpropanamide;

(2R)-2-[(4-{[1-(2-cyanobenzyl)-1H-indazol-5-yl]amino}quinazolin-5-yl)oxy]-N,N-dimethylpropanamide;

(2R)—N,N-dimethyl-2-[(4-{[1-(1,3-oxazol-2-ylmethyl)-1H-indazol-5-yl]amino}quinazolin-5-yl)oxy]propanamide;

(2S)-2-[(4-{[1-(3-fluorobenzyl)-1H-indazol-5-yl]amino}quinazolin-5-yl)oxy]-N,N-dimethylpropanamide;

N-[1-(3-fluorobenzyl)-1H-indazol-5-yl]-5-[(1S)-1-methyl-2-oxo-2-pyrrolidin-1-ylethoxy]-quinazolin-4-amine;

(2S)-2-[(4-{[1-(3-fluorobenzyl)-1H-indazol-5-yl]amino}quinazolin-5-yl)oxy]propanamide;

N-[1-(3-fluorobenzyl)-1H-indazol-5-yl]-5-[(1R)-1-methyl-2-oxo-2-pyrrolidin-1-ylethoxy]-quinazolin-4-amine;

(2R)-2-[(4-{[1H-(3-fluorobenzyl)-1H-indazol-5-yl]amino}quinazolin-5-yl)oxy]propanamide;

5-[(1S)-1-methyl-2-oxo-2-pyrrolidin-1-ylethoxy]-N-[1-(pyridin-2-ylmethyl)-1H-indazol-5-yl]quinazolin-4-amine;

(2S)-2-[(4-{[1-(pyridin-2-ylmethyl)-1H-indazol-5-yl]amino}quinazolin-5-yl)oxy]propanamide;

5-[(1S)-1-methyl-2-oxo-2-pyrrolidin-1-ylethoxy]-N-[1-(1,3-thiazol-2-ylmethyl)-1H-indazol-5-yl]quinazolin-4-amine;

(2S)—N,N-dimethyl-2-[(4-{[1-(1,3-thiazol-2-ylmethyl)-1H-indazol-5-yl]amino}quinazolin-5-yl)oxy]propanamide;

(2S)-2-[(4-{[1-(1,3-thiazol-2-ylmethyl)-1H-indazol-5-yl]amino}quinazolin-5-yl)oxy]propanamide;

5-[(1R)-1-methyl-2-oxo-2-pyrrolidin-1-ylethoxy]-N-[1-(1,3-thiazol-2-ylmethyl)-1H-indazol-5-yl]quinazolin-4-amine;

(2R)-2-[(4-{[1-(1,3-thiazol-2-ylmethyl)-1H-indazol-5-yl]amino}quinazolin-5-yl)oxy]propanamide;

(2R)-2-[(4-{[1-(1,3-thiazol-4-ylmethyl)-1H-indazol-5-yl]amino}quinazolin-5-yl)oxy]propanamide;

(2R)—N-methyl-2-[(4-{[1-(1,3-thiazol-4-ylmethyl)-1H-indazol-5-yl]amino}quinazolin-5-yl)oxy]propanamide;

(2R)—N-ethyl-2-[(4-{[1-(1,3-thiazol-4-ylmethyl)-1H-indazol-5-yl]amino}quinazolin-5-yl)oxy]propanamide;

5-[(1R)-1-methyl-2-oxo-2-pyrrolidin-1-ylethoxy]-N-[1-(1,3-thiazol-4-ylmethyl)-1H-indazol-5-yl]quinazolin-4-amine;

(2R)—N-(2-hydroxyethyl)-N-methyl-2-[(4-{[1-(1,3-thiazol-4-ylmethyl)-1H-indazol-5-yl]amino}quinazolin-5-yl)oxy]propanamide;

(2R)—N-(2-hydroxyethyl)-2-[(4-{[1-(1,3-thiazol-4-ylmethyl)-1H-indazol-5-yl]amino}quinazolin-5-yl)oxy]propanamide;

5-[(1R)-1-methyl-2-morpholin-4-yl-2-oxoethoxy]-N-[1-(1,3-thiazol-4-ylmethyl)-1H-indazol-5-yl]quinazolin-4-amine;

(2S)—N,N-dimethyl-2-[(4-{[1-(1,3-thiazol-4-ylmethyl)-1H-indazol-5-yl]amino}quinazolin-5-yl)oxy]propanamide;

(2S)—N-methyl-2-[(4-{[1-(1,3-thiazol-4-ylmethyl)-1H-indazol-5-yl]amino}quinazolin-5-yl)oxy]propanamide;

5-[(1S)-1-methyl-2-oxo-2-pyrrolidin-1-ylethoxy]-N-[1-(1,3-thiazol-4-ylmethyl)-1H-indazol-5-yl]quinazolin-4-amine;

5-[(1S)-1-methyl-2-morpholin-4-yl-2-oxoethoxy]-N-[1-(1,3-thiazol-4-ylmethyl)-1H-indazol-5-yl]quinazolin-4-amine;

(2S)—N-methyl-2-[(4-{[1-(pyridin-2-ylmethyl)-1H-indazol-5-yl]amino}quinazolin-5-yl)oxy]propanamide;

5-[(1S)-1-methyl-2-morpholin-4-yl-2-oxoethoxy]-N-[1-(pyridin-2-ylmethyl)-1H-indazol-5-yl]quinazolin-4-amine;

(2R)-2-[(4-{[1-(3-fluorobenzyl)-1H-indazol-5-yl]amino}quinazolin-5-yl)oxy]-N-methylpropanamide;

(2R)-2-[(4-{[1-(3-fluorobenzyl)-1H-indazol-5-yl]amino}quinazolin-5-yl)oxy]-N-ethylpropanamide;

(2R)-2-[(4-{[1-(3-fluorobenzyl)-1H-indazol-5-yl]amino}quinazolin-5-yl)oxy]-N-(2-hydroxyethyl)propanamide;

(2R)-2-[(4-{[1-(3-fluorobenzyl)-1H-indazol-5-yl]amino}quinazolin-5-yl)oxy]-N-(2-hydroxyethyl)-N-methylpropanamide;

N-[1-(3-fluorobenzyl)-1H-indazol-5-yl]-5-[(1R)-1-methyl-2-morpholin-4-yl-2-oxoethoxy]quinazolin-4-amine;

(2S)-2-[(4-{[1-(3-fluorobenzyl)-1H-indazol-5-yl]amino}quinazolin-5-yl)oxy]-N-methylpropanamide;

N-[1-(3-fluorobenzyl)-1H-indazol-5-yl]-5-[(1S)-1-methyl-2-morpholin-4-yl-2-oxoethoxy]quinazolin-4-amine;

(2R)—N-(2-hydroxyethyl)-2-[(4-{[1-(1,3-thiazol-2-ylmethyl)-1H-indazol-5-yl]amino}quinazolin-5-yl)oxy]propanamide;

(2R)—N-(2-hydroxyethyl)-N-methyl-2-[(4-{[1-(1,3-thiazol-2-ylmethyl)-1H-indazol-5-yl]amino}quinazolin-5-yl)oxy]propanamide;

(2R)—N-ethyl-2-[(4-{[1-(1,3-thiazol-2-ylmethyl)-1H-indazol-5-yl]amino}quinazolin-5-yl)oxy]propanamide;

(2R)—N-methyl-2-[(4-({[1-(1,3-thiazol-2-ylmethyl)-1H-indazol-5-yl]amino}quinazolin-5-yl)oxy]propanamide;

5-[(1R)-1-methyl-2-morpholin-4-yl-2-oxoethoxy]-N-[1-(1,3-thiazol-2-ylmethyl)-1H-indazol-5-yl]quinazolin-4-amine;

(2S)—N-methyl-2-[(4-{[1-(1,3-thiazol-2-ylmethyl)-1H-indazol-5-yl]amino}quinazolin-5-yl)oxy]propanamide; and 5-[(1S)-1-methyl-2-morpholin-4-yl-2-oxoethoxy]-N-[1-(1,3-thiazol-2-ylmethyl)-1H-indazol-5-yl]quinazolin-4-amine;

or a pharmaceutically acceptable salt thereof.

20. A pharmaceutical composition which comprises a compound of the Formula I, or a pharmaceutically acceptable salt thereof, according to claim 1 in association with a pharmaceutically acceptable diluent or carrier.

\* \* \* \* \*